United States Patent [19]
Johnston et al.

[11] Patent Number: 5,057,517
[45] Date of Patent: Oct. 15, 1991

[54] PIPERAZINYL DERIVATIVES OF PURINES AND ISOSTERES THEREOF AS HYPOGLYCEMIC AGENTS

[75] Inventors: David B. R. Johnston, Warren; Malcolm MacCoss, Freehold; Stephen Marburg, Metuchen; Laura C. Meurer, North Plainfield; Richard L. Tolman, Warren, all of N.J.

[73] Assignee: Merck & Co., Inc., Rahway, N.J.

[21] Appl. No.: 393,200

[22] Filed: Aug. 14, 1989

Related U.S. Application Data

[63] Continuation-in-part of Ser. No. 217,893, Jul. 14, 1988, abandoned, which is a continuation-in-part of Ser. No. 75,362, Jul. 20, 1987, abandoned.

[51] Int. Cl.$^5$ .................. A61K 31/52; C07D 473/18; C07D 473/34; C07D 471/04
[52] U.S. Cl. .................... 514/254; 544/255; 544/276; 544/277; 544/362
[58] Field of Search .............. 544/277, 276, 362, 255; 514/254

[56] References Cited

U.S. PATENT DOCUMENTS

| | | | |
|---|---|---|---|
| 3,016,378 | 9/1962 | Roch | 544/277 X |
| 3,331,843 | 7/1967 | Tomcufcik et al. | 544/277 X |
| 3,457,263 | 7/1969 | Regnier et al. | 544/277 |
| 3,850,917 | 11/1974 | Muller et al. | 544/255 X |
| 3,996,361 | 12/1976 | Friebe et al. | 544/277 |
| 4,459,296 | 7/1984 | Ancher et al. | 544/277 X |
| 4,728,644 | 3/1988 | Yuki et al. | 544/277 X |
| 4,849,423 | 7/1989 | Ott | 514/253 |
| 4,876,257 | 10/1989 | Hajos et al. | 514/253 |

FOREIGN PATENT DOCUMENTS

| | | |
|---|---|---|
| 724745 | 5/1969 | Belgium . |
| 0168500 | 1/1984 | European Pat. Off. . |
| 1115260 | 2/1957 | Fed. Rep. of Germany . |
| 1670940 | 10/1966 | Fed. Rep. of Germany . |
| 0010085 | 1/1987 | Japan . |
| 0864145 | 3/1961 | United Kingdom ............... 544/277 |
| 2119368 | 11/1983 | United Kingdom . |

OTHER PUBLICATIONS

Derwent Abstract 71293x/38 (1976).
Derwent Abstract 40365k/17 (1983).
Lettre et al., Chemical Abstracts, vol. 56; 12893e–128–94a (1962).
Hasan et al., Chemical Abstracts, vol. 107; 115913v (1987).
Regnier et al., Chemical Abstracts, vol. 77; 139981d (1972).
Bhakuni et al., Chemical Abstracts, vol. 102; 149701m (1985).
Obe et al., Chemical Abstracts, vol. 106: 196103s (1987).

*Primary Examiner*—Diana Rivers
*Attorney, Agent, or Firm*—David L. Rose; Joseph F. DiPrima

[57] ABSTRACT

There are disclosed certain 6-piperazinopurines and heteroaromatic derivatives thereof which have oral hypoglycemic acitivity and with such ability to lower blood sugar are useful in the treatment of type II diabetes and/or obesity with associated insulin resistance. Processes for the preparation of such compounds and compositions containing such compounds as the active ingredient thereof are also disclosed.

36 Claims, No Drawings

PIPERAZINYL DERIVATIVES OF PURINES AND ISOSTERES THEREOF AS HYPOGLYCEMIC AGENTS

CROSS REFERENCE TO RELATED APPLICATIONS

This application is a continuation-in-part of our co-pending application Ser. No. 217,893 filed 14 July 1988 which is a continuation-in-part of Ser. No. 75362 filed 20 July 1987 both now abandoned.

BACKGROUND OF THE INVENTION

Certain 6H-7,8-dihydrothiapyrano[3,2-d]pyrimidines are disclosed in Belgian Patent 724745 as intermediates for the preparation of compounds with cardiovascular and coronary dilation activity, however, suggestion is made neither of any hypoglycemic activity nor of weight reducing properties for either the intermediates or the final products. Great Britain 2119368 discloses 6H-7,8-dihydrothiapyrano[3,2-d]pyrimidines (where the bicyclic system is not heteroaromatic) with a very different substitution pattern on the nucleus when compared with the instant heteroaromatic compounds.

SUMMARY OF THE INVENTION

The instant invention is concerned with novel 6-piperazinopurines and heteroaromatic derivatives thereof, which are useful as hypoglycemic and/or weight reducing agents. Thus, it is an object of this invention to describe such compounds. It is a further object of this invention to describe the hypoglycemic activity of such compounds. A still further object is to describe compositions containing such compounds as the active ingredient thereof. Further objects will become apparent from a reading of the following description.

DESCRIPTION OF THE INVENTION

The 6-piperazinopurines of this invention are novel compounds with significant hypoglycemic activity. The compounds have the following structures:

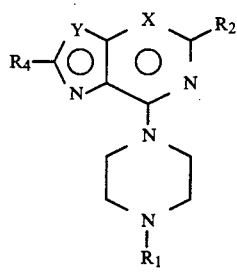

wherein X and Y have the following meanings:

| X | Y |
|---|---|
| N—(R$_3$)$_m$ | N—(R$_3$)$_n$ |
| C—R$_3$ | N—R$_3$ |
| N | S |
| N | O | and R$_1$ and R$_3$ are independently hydrogen, loweralkyl, cycloloweralkyl, loweralkenyl, loweralkoxyloweralkyl, loweralkenyl, loweralkynyl, phenylloweralkyl or substituted loweralkyl where the substituent is from 1 to 3 of halogen, loweralkylthio, loweralkylsulfinyl, loweralkylsulfonyl, loweralkylamino or diloweralkylamino, or the substituent is one of a 5- or 6-membered heteroaromatic ring system with nitrogen, oxygen or sulfur as the heteroatom, in particular where the hetero aromatic ring system is pyridyl, furyl or thienyl, and m and n are 0 or 1 such that when m is 0, n is 1 and when m is 1, n is 0;

R$_2$ and R$_4$ are independently hydrogen, loweralkyl, cycloloweralkyl, loweralkoxy, loweralkylthio, loweralkylsulfinyl, loweralkylsulfonyl, loweralkenyl, loweralkenyloxy, loweralkynyl, mono, di, or trihaloloweralkyl, phenyl or substituted phenyl where the substituent is from 1 to 3 of halo or loweralkyl, phenylloweralkyl, amino, loweralkylamino or dialkylamino where the alkyl group can be linear, branched or joined in a ring of 5- or 6-members optionally containing oxygen or nitrogen as a heteroatom and the pharmaceutically acceptable salts thereof.

The loweralkyl groups of this invention may contain from 1 to 6 carbon atoms and may be in either a linear or branched configuration. Exemplary of such groups are methyl, ethyl, propyl, isopropyl, butyl, sec-butyl, pentyl, hexyl, and the like.

The loweralkoxy groups of this invention may contain from 1 to 6 carbon atoms and may be in either a straight or branched configuration. Exemplary of such groups are methoxy, ethoxy, propoxy, butoxy, isobutoxy, pentoxy, hexoxy, and the like.

The loweralkenyl and loweralkynyl groups of this invention may contain from 2 to 6 carbon atoms and may be in either a linear or branched configuration. Exemplary of such groups are ethenyl, vinyl, butenyl, butynyl, propenyl, propargyl and the like.

The cycloloweralkyl groups of this invention may contain from 3 to 6 carbon atoms and are exemplified by cyclopropyl, cyclobutyl, cyclopentyl, and cyclohexyl.

The halogen atoms of this invention may contain any of the halogen fluorine, chlorine, bromine or iodine.

The amino and substituted amino groups are exemplified by amino, methylamino, dimethylamino, ethylamino, diethylamino, pyrrolidino, morpholino, propylamino, and the like.

The preferred compounds of this invention are those wherein R$_1$ is hydrogen, methyl, ethyl or 2-propenyl; R$_2$ is hydrogen, methyl, ethyl, methoxy, ethoxy, amino, methylamino, dimethylamino, pyrrolidino or ethylamino; each R$_3$ is independently hydrogen, methyl, ethyl, n-propyl, i-propyl, methoxymethyl, methoxyethyl, or fluoroethyl, in particular, a halogenated branched loweralkyl group, in particular a halogenated isopropyl, more preferred as a fluorinated isopropyl, and most preferred as 1,3-difluoro isopropyl; and each R$_4$ is independently hydrogen, methyl, methylamino or dimethylamino.

Further preferred compounds of this invention are realized in the following structural formula:

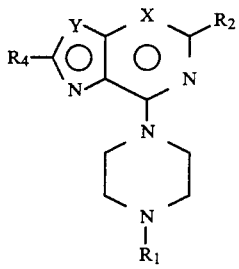

wherein $R_1$, $R_2$, $R_3$ and $R_4$ are as defined above, Y is S or $N-R_3$ and the corresponding X is N or $C-R_3$.

Further preferred compounds are realized in the purine compounds when X and Y are independently N and $N-R_3$.

In addition, those compounds where $R_1$ is hydrogen or methyl; $R_3$ is as defined above. and $R_2$ and $R_4$ are independently hydrogen, methyl, methoxy, ethoxy or dimethylamino are particularly preferred.

The most preferred compounds are those wherein $R_1$ is hydrogen. $R_2$ is methyl, methoxy or ethoxy, $R_3$ is as defined above, $R_4$ is hydrogen, X is N and Y is $N-R_3$.

Additional preferred compounds of this invention are found in the following combinations of substituents:

X=N, Y=N—$CH_3$, $R_1$=H, $R_2$=$CH_2CH_3$ $R_4$=H
X=N, Y=N—$CH_2CH_2CH_3$, $R_1$=H, $R_2$=$OCH_3$, $R_4$=H
X=N, Y=$NCH_2OCH_3$, $R_1$=H, $R_2$=$OCH_2CH_3$, $R_4$=H
X=N, Y=$NCH_2CH_2F$, $R_1$=H $R_2$=$OCH_3$, $R_4$=H
X=N, Y=$NCH_2CH_2F$, $R_1$=H, $R_2$=$CH_2CH_3$ $R_4$=H
X=N, Y-$NCH_2CH_2CH_2F$, $R_1$=H, $R_2$=$OCH_3$, $R_4$=H
X=N, Y=$NCH(CH_3)_2$, $R_1$=H, $R_2$=$OCH_3$, $R_4$=H
X=N, Y=$NCH(CH_2F)_2$, $R_1$=H, $R_2$=$OCH_3$, $R_4$=H
X=N, Y=$NCH(CH_2F)_2$, $R_1$=H, $R_2$—$OCH_2CH_3$, $R_4$=H
X=N, Y=$NCH(CH_2F)_2$, $R_1$=H, $R_2$=$CH_2CH_3$, $R_4$=H
X=N, Y=N-[1S,2R]$CH(CH_3)CHFCH_3$, $R_1$=H, $R_2$=$OCH_3$, $R_4$=H
X=N, Y=N-[1S,2R]$CH(CH_3)CHFCH_3$, $R_1$=H, $R_2$=$OCH_3$, $R_4$=$CH_3$
X=N, Y=N-[1S,2S]$CH(CH_3)CHFCH_3$, $R_1$=H, $R_2$=$OCH_3$, $R_4$=H
X=N, Y=N-[1S,2S]$CH(CH_3)CHFCH_3$, $R_1$=H, $R_2$=$OCH_3$, $R_4CH_3$
X=N, Y=N-[1R,2S]$CH(CH_3)CHFCH_3$, $R_1$=H, $R_2$=$OCH_3$, $R_4$=H
X=N, Y=N-[1R,2S]$CH(CH_3)CHFCH_3$, $R_1$=H, $R_2$=$OCH_3$, $R_4$=$CH_3$
X=N, Y=N-[1R,2S]$CH(CH_3)CHFCH_3$, $R_1$=H, $R_2$=$OCH_3$, $R_4$=H
X=N, Y=N-[1R,2R]$CH(CH_3)CHFCH_3$, $R_1$=H, $R_2$=$OCH_3$, $R_4$=H
X=N, Y=N-[S]$CH(CH_3)CH_2CH_3$, $R_1$=H, $R_2$=$OCH_3$, $R_4$=H
X=N, Y=N-[R]$CH(CH_3)CH_2CH_3$, $R_1$=H, $R_2$=$OCH_3$, $R_4$=H
X=N, Y=N-[1S,2R]$CH(CH_3)CH(OCH_3)CH_3$, $R_1$=H, $R_2$=$OCH_3$, $R_4$=H
X=N, Y=N-[1R,2S]$CH(CH_3)CH(OCH_3)CH_3$, $R_1$=H, $R_2$=$OCH_3$, $R_4$=H
X=N, Y=N-[1R,2R]$CH(CH_3)CH(OCH_3)CH_3$, $R_1$=H, $R_2$=$OCH_3$, $R_4$=H.
X=N, Y=N-[1S,2S]$CH(CH_3)CH(OCH_3)CH_3$, $R_1$=H, $R_2$=$OCH_3$ and $R_4$=H With the presence of various amino groups, it will be appreciated that the instant compounds will be basic in nature and will be capable of forming acid addition salts with acidic compounds. The pharmaceutically acceptable acid addition salts of the compounds of this invention are included within the ambit of this invention. Examples of such pharmaceutically acceptable acid addition salts are those formed from inorganic acids such as hydrochloric, hydrobromic, nitric, sulfuric, phosphoric, dialkylphosphoric, or hypophosphorous; and organic acids such as acetic, benzenesulfonic, benzoic, citric, fumaric, gluconic, lactic, malic, maleic, oxalic, pamoic, pantothenic, salicyclic, stearic, succinic, tannic, tartaric, and the like.

The instant compounds may also be used in combination with other compounds, in particular combinations with other acid hypoglycemic agents is useful. In particular, the instant compounds may be used in combination with sulfonylureas for beneficial effect.

The instant compounds are prepared according to the following reaction scheme:

SCHEME I

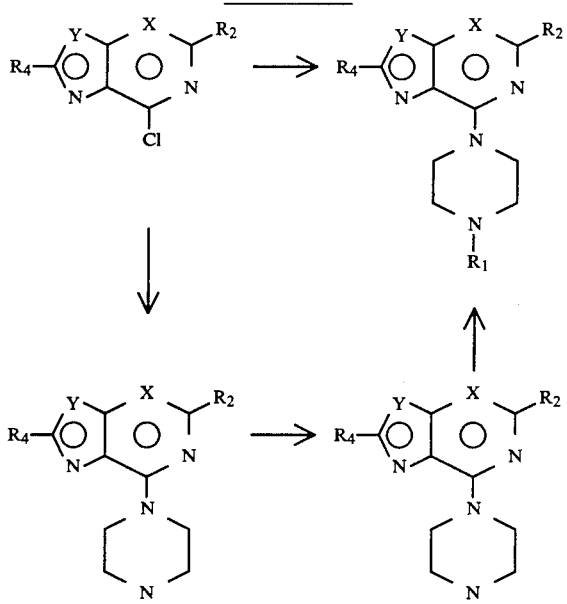

wherein X, Y, $R_1$, $R_2$, $R_3$ and $R_4$ are as defined above.

The foregoing reaction is carried out by reacting an $R_1$-substituted piperazine with the chloroheterocycle (II). When $R_1$ is hydrogen the reactant can be protected piperazine such that only one of the piperazine nitrogen atoms are available for reaction.

The preferred protecting group is the t-butoxycarbonyl (BOC) group. After the protected piperazine has been reacted with the chloroheterocyclic substrate, the protecting group is removed.

The displacement of the chloro by the $R^1$-piperazine or protected piperazine is carried out in an optional solvent at a temperature of from 100° to 150° C. such that the solvent does not boil at a temperature less than the desired reaction temperature. The preferred solvents are N,N'-dimethylformamide, ethanol, isoamyl alcohol and the like. It is preferred to carry out the reaction at from about 75° to 125° C. and the reaction is generally complete in from about 30 minutes to 16 hours. The reaction proceeds well in the absence of a solvent. The piperazine reagent is generally used in at least 1 molar excess in order to neutralize the hydrogen chloride liberated during the course of the reaction. Preferably 4 equivalents of the piperazine compound are employed. Optionally, the use of a tertiary amine such as triethylamine can be used to reduce the amount of piperazine compound employed in the reaction. The products are isolated from the reaction mixture using standard techniques.

The reactions used to prepare the instant compounds are generally carried out with the displacement of the halogen by the $R^1$-piperazine as the last step. However, the $R^1$ group can be introduced on the unsubstituted piperazine after the piperazine has been placed on the heterocycle and after the removal of the protecting group. Similarly, the reactions used to prepare the heterocycle can include the substitution of the piperazine group prior to the final synthetic steps such as the heterocyclic ring closure or the substitution of the $R_2$, $R_3$ and $R_4$ groups (See Scheme 1A).

SCHEME IA

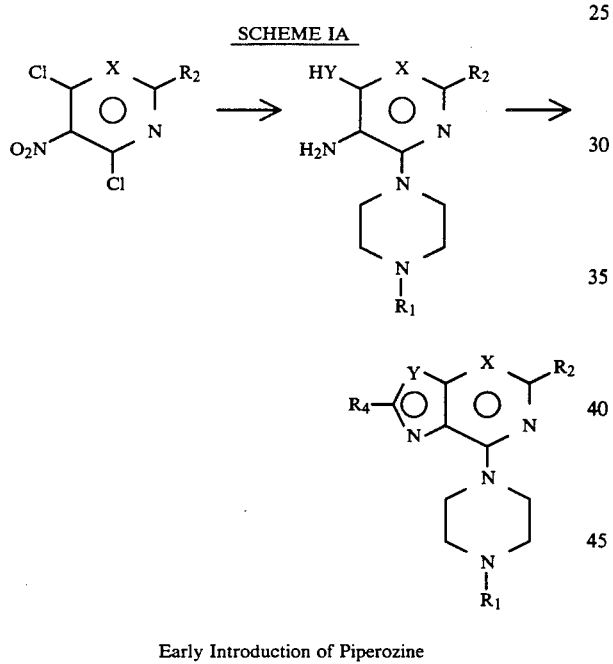

Early Introduction of Piperozine

Occasionally, the presence of more than one reaction site may result in the preparation of a mixture which will be separated in order to obtain the instant compounds. The various procedures available to those skilled in the art for the preparation of the instant compounds are outlined below and in the appended examples.

The Preparation of 6-(1-piperazinyl)-Substituted Purines

Alkylation with $R_3$—Z (Z=leaving group) of a 6-chloropurine with ensuing replacement of chlorine by a protected piperazine followed by deprotection

SCHEME II

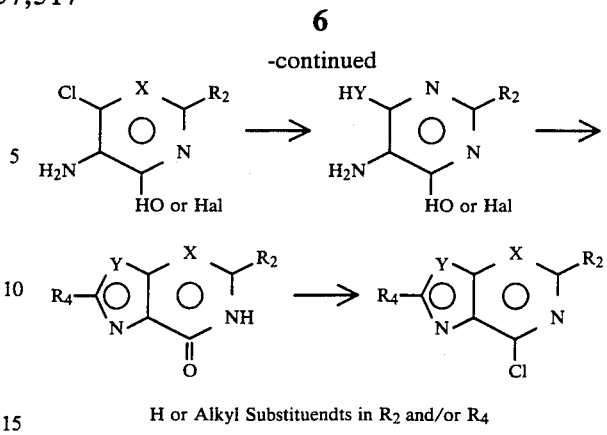

H or Alkyl Substituendts in $R_2$ and/or $R_4$

SCHEME III

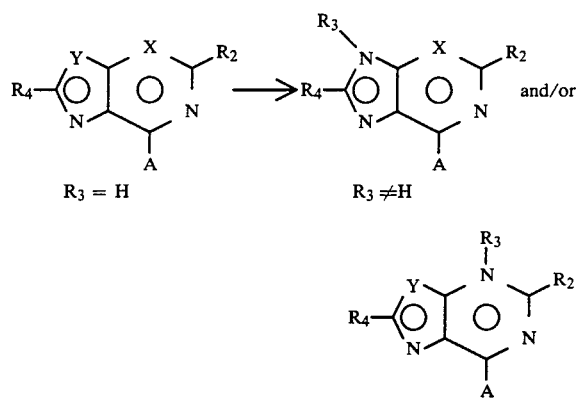

A = halogen or sub'd-piperazine

Transformation of 6-chloropurine to 6-[1-(4-protected) piperazinyl]purine followed by alkylation and deprotection.

SCHEME IV

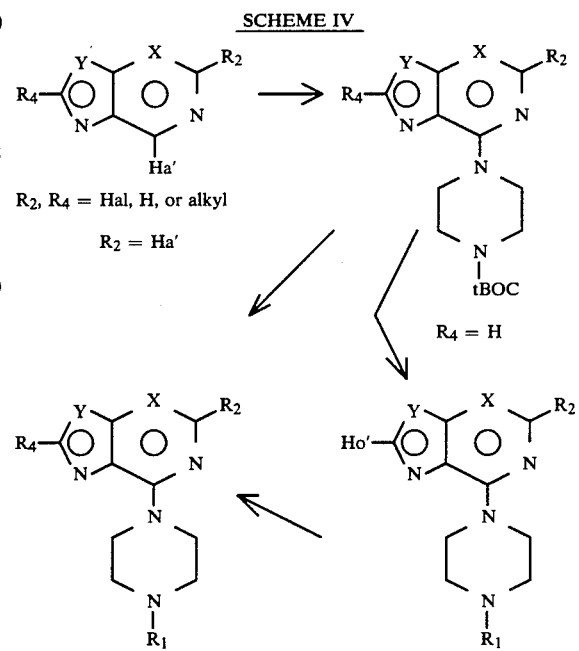

$R_2$, $R_4$ = Hal, H, or alkyl $R_2$ = Ha'

$R_4$ = H

Electronegative Elements in $R_2$ and/or $R_4$

In addition to the preparation of the compounds of the current invention by the general routes shown in Schemes I–IV, it is possible to carry out additional functionalization on the side chains after initial preparation of a piperazine-blocked purine derivative. Such an example is shown in Scheme V for the particular case where the N9-side chain is further transformed into a series of derivatives bearing a stereochemically defined substitution pattern. Other transformations using procedures and techniques known to one skilled in the art of organic synthesis are possible in order to give derivatives with the required functionality and stereochemistry.

The currently available oral hypoglycemic agents are not completely satisfactory since they may not offer complete blood glucose control or may provide a variety of undesirable side effects or they may elevate insulin concentrations to undesirable and dangerous levels. Thus, the search for improved oral hypoglycemic agents is a continuing one.

As previously indicated, the compounds of this invention are all readily adapted to therapeutic use as oral hypoglycemic agents, in view of their ability to lower the blood sugar levels of diabetic subjects to a statisti-

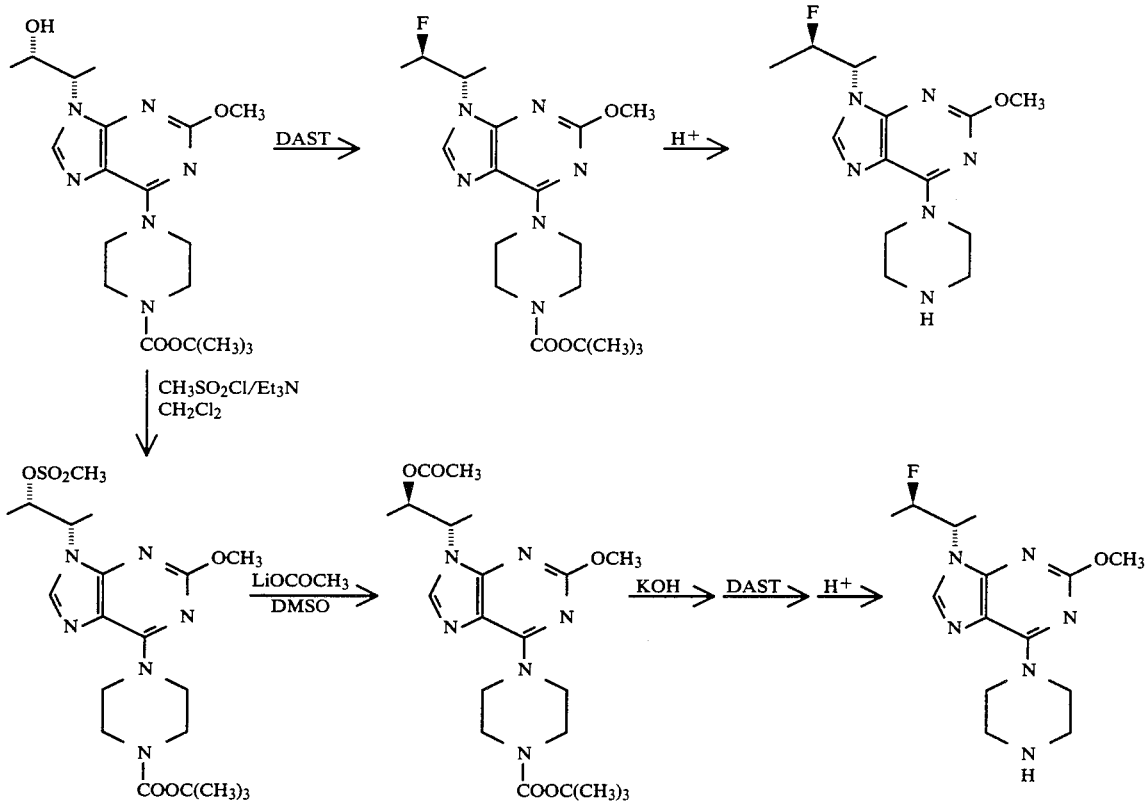

SCHEME V

Diabetes is a condition characterized by abnormal insulin secretion and a variety of metabolic and vascular manifestations reflected in a tendency toward inappropriately elevated blood glucose levels and which if left poorly treated or untreated can result in accelerated, nonspecific atherosclerosis, neuropathy and thickened capillary lamina causing renal and retinal impairment. Diabetes is characterized as being insulin dependent (Type I) and non-insulin dependent (Type II). Type I diabetes is due to damage and eventual loss of the ^-cells of the pancreatic islets of Langerhans with a resulting loss of insulin production. Type II diabetics secrete insulin, however, the insulin is somehow not properly or effectively utilized in the metabolism of blood sugars and glucose accumulates in the blood to above normal levels. This condition is termed insulin resistance.

With the certainty of serious complications resulting from high glucose levels in poorly controlled or uncontrolled diabetics, means to lower blood glucose have been research goals for a considerable period of time. With Type I diabetes glucose control can only be achieved with daily insulin injections. With Type II diabetes glucose control can be effected from a combination of diet and drugs which lower glucose levels.

cally significant degree. For instance, 6-(1-piperazinyl)-9-methylpurine, a typical and preferred agent of the present invention, has been found to consistently lower blood sugar levels and improve glucose tolerance in either fasted or fed diabetic (i.e., hyperglycemic) mice to a statistically significant degree when given by the oral route of administration at dose levels ranging from 1 mg/kg to 100 mg/kg, respectively, without showing any toxic side effects. The other compounds of this invention also produce similar results. In general, these compounds are ordinarily administered at dosage levels ranging from about 1 mg to about 100 mg per kg of body weight per day, although variations will necessarily occur depending upon the condition and individual response of the subject being treated and the particular type of oral pharmaceutical formulation chosen.

Administration over time to obese, insulin resistant mice, resulted in a significant reduction in body weight.

In connection with the use of the compounds of this invention for the treatment of diabetic subjects, it is to be noted that they may be administered either alone or in combination with other oral hypoglycemic agents in pharmaceutically acceptable carriers and that such administration can be carried out in both single and multiple dosages. More particularly, the novel compounds of the invention can be administered in awide variety of different dosage forms, i.e., they may be combined with various pharmaceutically acceptable inert carriers in the forms of tablets, capsules, lozenges, troches, hard candies, powders, aqueous suspension, elixirs, syrups and the like. Such carriers include diluents or fillers, sterile aqueous media and various non-toxic organic solvents, etc. Moreover, such oral pharmaceutical compositions can be suitably sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as hypoglycemic agents, is determined by their ability to lower blood sugar levels in the fasted or glucose loaded hyperglycemic mouse when tested therein for such purposes according to the procedures described by Saperstein et al. as submitted to the journal *Metabolism* and summarized as follows: Genetically obese mice (ob/ob) were fasted overnight.

The compounds were administered orally via a stomach tube and each mouse serially bled from the orbital sinus at various times and the blood samples were analyzed for blood glucose. When the effects of the compounds on blood glucose levels of glucose loaded mice were to be determined, glucose was administered orally at a rate of 2 g per kg. 30 minutes after administration of the test compound. Glucose in the blood was determined by the potassium ferricyanide potassium ferrocyanide oxidation reaction auto analyzer.

The latter method measures directly the amount of glucose in the blood at any given time and from this, the maximum percent decrease in blood sugar can be readily calculated and reported as hypoglycemic activity per se. In this way, the present compounds are shown to markedly improve glucose tolerance of non-anesthetized hyperglycemic mice when administered to them at dose levels as low as 10 mg/kg orally and lower fasting blood glucose levels when administered at dose levels as low as 30 mg/kg orally.

The instant invention is further described by the following examples which are intended to be merely descriptive and should not be construed as limitative of the invention.

EXAMPLE 1

6-[1-(4-tert-butoxycarbonyl)piperazinyl]purine

6-Chloropurine (4.6 g, 30 mmol) and 11.2 g (60 mmol) of N-(1-tert-butoxycarbonyl)piperazine (BOC-piperazine) were dissolved in dimethylformamide (DMF) (150 ml) and the solution was stirred overnight at 100° C. under nitrogen ($N_2$). The reaction mixture was then evaporated to dryness in vacuo and the residue crystallized from n-propanol affording 5.0 g (55% of 6-[1-(4-BOC)piperazinyl]purine, m.p. 244°-246° C.

Calc'd for $C_{14}H_{20}N_6O_2$: C, 55.26; H, 6.58; N, 27.63. Found: C, 55.23; H, 6.48; N, 27.63.

EXAMPLE 2

6-[1-(4-BOC)piperazinyl]-9-methylpurine

Method A

To 6-[1-(4-BOC)piperazinyl]purine (1.6 g, 5.58 mmol) dissolved in 60 ml of dimethylsulfoxide (DMSO) was added potassium carbonate (848 mg, 6.14 mmol) and methyliodide (0.70 ml, 11.2 mmol). The mixture was stoppered and stirred at room temperature for 24 hours at which time an additional 0.35 ml (5.6 mmol) of methyliodide was added. Stirring was continued for an additional 24 hours and then the reaction mixture was quenched in water. The aqueous mixture was extracted with ethyl acetate. The organic layer was dried with $Na_2SO_4$ and evaporated to dryness affording 1.3 g of a mixture of 9- and 7-isomers. These were separated on a 100 ml silica gel column using a 90:10 ethylacetate:ethanol mixture as eluent. The first peak after concentration afforded 1.0 g (56%) of 6-[1-(4-BOC)piperazinyl]-9-methylpurine, m.p. 129°-131° C.

Calc'd for $C_{15}H_{22}N_6O_2$: C, 56.60; H, 6.92; N, 26.42. Found: C, 56.10; H, 6.78; N, 26.11.

Method B

To 4.5 g (26.7 mmol) of 6-chloro-9-methyl purine dissolved in 70 ml of sieve dried, degassed, DMF (dimethylformamide) was added 4.966 g of BOC-piperazine (26.7 mmol) and 4.6 ml of diisopropylethylamine (26.7 mmol). The solution was stored, under $N_2$, at 100° C. for 16 hrs., after which it was evaporated to dryness in vacuo. The orange residue was triturated with warm water (100 ml). The process was repeated and neither water layer showed product (t.l.c.). The residue was dissolved in boiling methanol charcoaled (10% by weight), and after filtration through celite, evaporated to dryness. The residue was dissolved in 95:5 ethyl acetate:ethanol and adsorbed onto 15 ml of silica gel. This was added to the top of a 250 ml silica gel column (dry column) and eluted with 250 ml of 95:5 ethyl acetate:ethanol and then a 90:10 mixture. 100 ml fractions were collected and the product which is eluted in fractions 7 to 13. The t.l.c. (9:1 ethyl acetate:ethanol): a single spot shows no BOC piperazine. Recrystallization was effected with acetonitrile affording 7 g of 6-[1-(4-BOC)piperazinyl]-9-methylpurine, m.p. 129°-131° C.

Calc'd for $C_{15}H_{22}N_6O_2$: C, 56.60; H, 6,92; N, 26.42. Found: C, 55.76; H, 6.71; N, 25.98.

EXAMPLE 3

6-[1-(4-BOC)piperazinyl]-3-methylpurine

The second peak from the above chromatography in Example 2, Method A, after concentration afforded 83 mg (5%) of 6-[1-(4-BOC)piperazinyl]-3-methylpurine, m.p. 235°–238° C.

EXAMPLE 4

6-(1-piperazinyl)-9-methylpurine

6-[1-(4-BOC)piperazinyl]-9-methylpurine (2.5 g, 8.09 mmol) was dissolved in 50 ml of trifluoroacetic acid (TFA) and the solution aged for 1 hour at room temperature. The TFA was removed in a stream of $N_2$ and the residue dissolved in 2N HCl (20 ml) and the acidic solution evaporated to dryness in vacuo. This HCl treatment was repeated twice and the final residue crystallized from methanol-acetonitrile affording 1.71 g (73%) of 6-(1-piperazinyl)-9-methylpurine dihydrochloride, m.p. 300° C.

Calc'd for $C_{10}H_{16}N_6Cl_2$: C, 41.23; H, 5.5; N, 28.87; Cl, 24.4. Found: C, 41.33; H, 5.5; N, 28.7; Cl, 24.37.

U.V. $(H_2O)\lambda_{max}=274$ ($\epsilon=21,454$).

$\lambda_{min}=230$; other$\lambda_{max}=218$ ($\epsilon=19,283$).

EXAMPLE 5

N-t-Butoxycarbonyl-N'-benzyloxycarbonylpiperazine

To 15 g of BOC-piperazine (80.6 mmol) dissolved in acetone (50 ml) was added in alternating portions benzylchloroformate (11.5 ml, 80.6 mmol) and 1N NaOH (15 ml) keeping the pH at 8–8.5 and the temperature 0°–5° C. After 2 hours, starting material was still present (tlc) and an additional quantity of benzylchloroformate (5 ml) and 1N NaOH (5 ml) was added. The reaction mixture was aged at 5° C. overnight and at room temperature an additional 7 hours. Water was added and the mixture extracted with ethyl acetate (3×50 ml), dried with $Na_2SO_4$ and concentrated to 21 g of an oil. This oil was dissolved in 10 ml of ethyl acetate, passed through 40 ml of silica gel and eluted with 200 ml of ethylacetate. Crystallization was effected by trituration with petroleum ether and the crystals collected, affording 8.28 g (32%) of N-t-butoxycarbonyl-N'-benzyloxycarbonylpiperazine, m.p. 90.5°–91.5° C.

Calc'd for $C_{17}H_{24}N_2O_4$: C, 63.75; H, 7.5; N, 8.75. Found: C, 63.53; H, 7.48; N, 8.93.

NMR (CDCl$_3$, δ from TMS) δ1.45 (s, 9), δ3.45 (m, 8), δ5.12 (s, 2), δ7.3 (m, 5).

EXAMPLE 6

N-Benzyloxycarbonylpiperazine (CBZ-piperazine)

960 mg (3 mmol) of N-butoxycarbonyl-N'-benzyloxycarbonylpiperazine was dissolved in 8 ml of TFA and aged for 1 hour. The TFA was evaporated in a stream of $N_2$ and then to the residue was added water and NaOH to pH12. The basic mixture was extracted with 3×15 ml of ethyl acetate, backwashed with saturated aqueous NaCl, dried with $Na_2SO_4$ and concentrated to 566 mg of an oil whose mass spectrum had a parent peak at m/e=220. NMR ($_3$CDCl, δ from TMS) δ2.8 (m, 4), δ3.5 (t, 4), δ5.12 (s, 2), δ7.38 (m, 5).

EXAMPLE 7

9-(1--^-Ribofuranosyl)-6-[1-(4-benzyloxycarbonyl)-piperazinyl]purine

6-Chloropurine riboside (237 mg, 0.834 mmol) and 410 mg (1.86 mmol) of CBZ-piperazine were dissolved in 12 ml of DMF and heated at 100° C. for 20 hours. The mixture was then concentrated to dryness in vacuo affording 854 mg of a residue. This was chromatographed on silica gel (60 ml) eluting with equal volumes of methylene chloride, 2% ethanol in methylene chloride (v/v) and finally with 40% ethanol in methylene chloride (v/v) evaporation of appropriate fractions afforded 320 mg (82%) of 6-[1-(4-CBZ)piperazinyl]purine riboside.

EXAMPLE 8

9-(1-^-D-Ribofuranosyl)-6-(1-piperazinyl)purine 9-(1--^-D-ribofuranosyl)-6-[1-(4-CBZ)piperazinyl]purine (300 mg, 0.64 mmol) dissolved in 10 ml of ethanol was hydrogenated overnight under 40 psi of hydrogen in the presence of 50 mg 10% palladium on charcoal. The reaction mixture was filtered through diatomaceous earth and evaporated to 221 mg of crude product. This was recrystallized three times from ethanol-ether to afford 70 mg of 6-(1-piperazinyl)purine riboside.

Calc'd for $C_{14}H_{20}N_6O_4.0.5 H_2O$: C, 48.70; H, 6.09; N, 24.35 Found: C, 49.01; H, 5.76; N, 24.31

U.V.$\lambda_{max}$ ($H_2O$) 275; $\epsilon=1.81\times10^4$, $\lambda_{max}$ 215, $\epsilon=13.5\times10^4$.

FAB mass spectrum m/e=337 (M+1).

EXAMPLE 9

6-Chloro-9-methylpurine

To 5.0 g (31 mmol) of 5-amino-4-chloro-6-methylaminopyrimidine suspended in 200 ml of triethyl orthoformate was added 2.6 ml of concentrated HCl and the resultant mixture stirred overnight at room temperature (r.t.). The white precipitate was then collected, washed with ether which was then combined with the orthoformate which was concentrated to give pure 6-chloro-9-methylpurine by tlc (thin layer chromatography) (silica, 90:10 CHCl$_3$:CH$_3$OH). The filtered solid was returned to 150 ml ethyl orthoformate, treated with 1.0 ml concentrated HCl and stirred at 60° C. for 18 hours. The solution was evaporated and the solids combined to give 5 g (94%) of 6-chloro-9-methylpurine, m.p. 205°–207° C.

EXAMPLE 10

4-[1-(4-BOC)piperazinyl]-5,6-diaminopyrimidine 2.0 g (13 mmol) of 6-chloro-4,5-diamino pyrimidine (Lin et al *J. Org. Chem.* 26, 264–265 (1961)) and 10 g (54 mmol) of N-BOC-piperazine was stirred, molten, at 130° C. for 5 hours. Then an additional 2 g of BOC-piperazine were added and heating continued for an additional 2 hours. The t.l.c. (90:10 ethl acetate:ethanol) showed only small amounts of the pyrimidine reactant. A large fraction of the unreacted BOC-piperazine was removed by sublimation at 100°–130° C. and the residue was chromatographed on 800 ml of silica gel eluting with 90:10 ethyl acetate ethanol. There was obtained 1.8 g of 4-[1-(4-BOC)piperazinyl]-5,6-diaminopyrimidine.

200 MHz NMR(CDCl$_3$, δ from TMS): 1.46(s,9), 3.17(m,4), 3.55(m,4), 8.02(s,1).

EXAMPLE 11

6-[1-(4-BOC)piperazinyl]-8-methylpurine

To 500 mg (1.7 mmol) of 4-[1-(4-BOC)piperazinyl]-5,6-diaminopyrimidine dissolved in 5.2 ml of 2-methoxyethanol was added 271 mg (2.3 mmol) of acetamidine acetate and the mixture was refluxed under nitrogen for 22 hours. At this time an additional 100 mg of acetamidine acetate was added and reflux was continued for an additional 3 hours. The mixture was then partitioned between ethylacetate and water, the organic layer dried and concentrated to 630 mg of crude product. This was chromatographed on 65 ml of silica gel eluting with equal volumes of 95:5, 93:7, 88:12 and 80:20 ethylacetate:ethanol. The NMR spectrum of the fractions eluting after 150 ml (200 mg) showed mostly product [mass spectrum:(fast atom bombardment) m/e=319(M+H)]. An analytical sample of the title compound was obtained after two recrystallizations from toluene.

Calc'd for $C_{15}H_{22}N_6O_2 \cdot 2H_2O$: C, 55.58; H, 7.04; N, 25.92. Found: C, 56.03; H, 6.93; N, 25.47.

uv (methanol): λmax 273 nm.

EXAMPLE 12

8-Methyl-6-(1-piperazinyl)purine

To 1.6 ml of trifluoroacetic acid (TFA) was added 54 mg (0.17 mmol) of 6-[1-(4-BOC)piperazinyl]-8-methylpurine and the solution aged for 1 hour. The TFA was then evaporated in a stream of dry nitrogen and the residue converted to the hydrochloride by dissolving it in 2 ml of 2N HCl and evaporating in vacuo. This process was repeated twice. The hydrochloride was recrystallized from methanol-acetonitrile affording 34 mg of 8-methyl-6-(1-piperazinyl)purine (isolated as hydrated di hydrochloride:

Calc'd for $C_{10}H_{14}N_6 \cdot 2HCl \cdot 0.8H_2O \cdot 0.05$ NaCl: C, 38.91; H, 5.75; N, 27.22; Cl, 23.57. Found: C, 39.29; H, 5.55; N, 26.84; Cl, 23.95.

Mass spectrum m/e=218.

EXAMPLE 13

5-Amino-4-[1-(4-BOC)piperazinyl]-6-methylamino pyrimidine

To a stirred melt of 11 g (59 mmol) of BOC-piperazine at 130° C. was added 2.06 g (13 mmol) of 5-amino-6-chloro-4-methylaminopyrimidine (Robins et al, *JACS*, 79, 490–494 (1957)) and the mixture heated at 130° C. for 6.5 hours. Then after aging at room temperature overnight, the reaction mixture was heated for an additional 48 hours at 130° (at 24 hours an additional 2 g of BOC piperazine was added.) Excess BOC piperazine was removed by sublimation and the residue (8 g) was chromatographed on a 600 ml silica gel (dry) column eluting with ethyl acetate. The product (400 mg) elutes with 3.6 to 4.6 L of eluent. Mass spectrum: m/e=308.300 MHz NMR (CDCl$_3$, δ from TMS): 1.45 (s,9), 3.05 (m,7), 3.50 (m,4), 8.14 (s,1).

EXAMPLE 14

6-[1-(4-BOC)piperazinyl]-8,9-dimethylpurine

To 400 mg (1.29 mmol) of 5-amino-4-[1-(4-BOC)-piperazinyl]-6-methylaminopyrimidine dissolved in 2 ml of 2-methoxyethanol was added 305 mg (2.58 mmol) of acetamidine acetate and the mixture refluxed for 24 hours and then aged for an additional 16 hours at room temperature. The solution was then quenched into H$_2$O and extracted with ethylacetate. The organic layer was dried over sodium sulfate and concentrated to 474 mg of a mixture. This was chromatographed on 105 g of silica gel with a chloroform-methanol step gradient [from 100% chloroform to 92% (v/v) chloroform: 8% methanol]. The product was identified by t.l.c. and recrystallized three times from cyclohexane affording 77 mg of 6-[1-(4-BOC)piperazinyl]-8,9-dimethylpurine.

EXAMPLE 15

8,9-Dimethyl-6-(1-piperazinyl)purine

6-[1-(4-BOC)piperazinyl]-8,9-dimethyl purine (75 mg, 0.25 mmol) was dissolved in 2.0 ml of trifluoroacetic acid (TFA) and the solution aged at room temperature for 1 hour. The TFA was then evaporated in a stream of dry nitrogen and the residue converted to the hydrochloride by three times dissolving it in 2 ml of 2N HCl and concentrating to dryness. The crude hydro chloride was recrystallized from methanol-acetonitrile affording 59 mg (82%) of 8,9-dimethyl-6-(1-piperazinyl)purine.

Calc'd for: $C_{11}H_{16}N_6 \cdot 2HCl \cdot 0.3H_2O$: C, 42.31; H, 5.96; N, 26.92; Cl, 22.76. Found: C, 42.30; H, 5.88; N, 26.80; Cl, 23.03 mass spectrum (EI) m/e 232.

EXAMPLE 16

Imidazo[4,5-c]pyridine(3-deazapurine)

To 5.0 of 3,4-diaminopyridine (Aldrich, 45.82 mmol) suspended in 45 ml of 2-methoxyethanol was added 6.4 g of formamidine acetate (Aldrich, 61.5 mmol) and the mixture heated at reflux (it becomes a solution) for 16 hrs. The solution was then evaporated in vacuo to a solid residue which was recrystallized from 50 ml of acetonitrile. This afforded 4.06 g of imidazo[4,5-c]pyridine (74.5%) m.p. 166°–168° C. [lit 162°–163° C., Y. Mizuno, et al. *Chem. Phar. Bull.*, 12, 866–872 (1964)]. 200 MHz NMR (D$_2$O, δ from TSP): 7.6 (1H, d, J=6 Hz) 8.23 (1H, d, J=6 Hz) 8.30 (1H,s) 8.84 (1H,s).

EXAMPLE 17

1H-Imidazo[4,5-c]pyridine-5-oxide

1H Imidazo[4,5-c]pyridine (4.0 g, 33.6 mmol) was dissolved in 60 ml of fresh acetic acid, heated to 73° C.±1° C. and to the solution was added 8.8 ml of 30% H$_2$O$_2$ (78 mmol). After stirring and heating at 73° C. for 24 hrs, an additional 5 ml of H$_2$O$_2$ was added as well as 1 ml of trifluoroacetic acid. Heating at 73° C. was continued for an additional 3 days. After concentrating, an aliquot NMR (D$_2$O) shows a 2:1 product: starting material mixture. Concentration of the main reaction mixture was followed by trituration of the residue with 50 ml of acetonitrile. The filtered insolubles 1.6 g (35%) are pure N-oxide by TLC, (reverse phase, 9:1 H$_2$O:THF) 200 MHz NMR (D$_2$O, δ from TSP): 7.82 (1H, d, J=7 Hz) 8.21 (1H, d of d, J=7 Hz, J=1 Hz) 8.52 (1H, s) 8.84 (1H, d, J=1).

A second crop of 0.8 g is obtained by aging at 4° C.

EXAMPLE 18

4-Chloroimidazo-(4,5-c)pyridine 2.84 g (21 mmol) of imidazo(4,5-c)pyridine-5-oxide was dissolved in 200 ml of freshly distilled POCl$_3$ and refluxed for 16 hrs. The insolubles (starting material, approx. 0.8 g) were filtered and the excess POCl₃ was then removed by distillation and the residue was dissolved in 30 ml of H₂O and made basic with concentrated NH₃ to pH 8. The solution was extracted 3 times with 30 ml of isoamyl alcohol. This was backwashed with 1 ml of H₂O and concentrated to give 1 g of product. This was dissolved in 5–10 ml of 1:1 ethanol:CHCl₃ and applied to a silica gel column (56 g) packed in 7% ethanol:CHCl₃ and then eluted with 15% ethanol:CHCl₃. Chromatographically pure material (0.710 g, 22%) was obtained. Based on recovered starting material the yield is 31%. 200 MHz NMR (DMSO, $\delta$ from TMS): 7.68 (1H, d, J=6 Hz), 8.20 (1H, d, J=6 Hz) 8.50 (s, 1H).

EXAMPLE 19

4-[1-(4-BOC)piperazinyl]-1H-imidazo(4,5-c)pyridine 253 mg (1.65 mmols) of 4-chloro-1H-imidazo(4,5-c)pyridine and 1.07 g BOC-piperazine were dissolved in 2 ml of DMF and the solution was heated at 150° C. for 2 hrs, aged at room temperature for 16 hrs and then heated an additional 4 hrs at 150° C. The DMF was removed in vacuo, the residue covered with 7 ml of ethyl acetate, filtered (the solid gives a positive AgNO₃ test) and the resulting filtrate applied to a 14 g silica gel column developed with EtOAc. The first UV positive peak was concentrated to 0.72 g of a mixture. This was rechromatographed on 22 g of silica gel (packed in CHCl₃) eluting with 250 ml 20:80 EtOAc:CHCl₃, 250 ml 33:67 EtOAc:CHCl₃, 250 ml 1:1 EtoAc:CHCl₃ and then with pure EtOAc. Fractions containing the required material were concentrated to give 164 mg of pure product (32%). 300 MHz NMR (CDCl₃, $\delta$ from TMS) 1.5 (9H,s) 3.6 (4H, m), 4.15 (4H, m), 6.76 (1H, d, J=5 Hz) 7.92 (1H, s) 7.95 (1H, d, J=5 Hz).

EXAMPLE 20

4-[1-(4-BOC)piperazinyl]-1-methyl-1H-imadazo[4,5-c]pyridine

To 158 mg of 4[1-(4-BOC)piperazinyl]-1H-imidazo(4,5-c)pyridine (0.52 mmol) dissolved in 3.8 ml DMF was added 36 mg of 60% NaH/in oil and 0.064 ml of methyl iodide. The mixture was stirred for 6 hrs at room temperature and then quenched into 20 ml of CH₂Cl₂. This was washed 5 times with 12 ml of H₂O, 12 ml of saturated aqueous NaCl and then dried over Na₂SO₄. Concentration afforded 187 mg of crude product which was purified by preparative TLC 2×1000μ silica gel plates) developed in 60:50 CH₂Cl₂:EtOAc to give 84 mg of pure product.

EXAMPLE 21

1-Methyl-4-(1-piperazinyl)-1H-imidazo(4,5-c)pyridine

The above 84 mg from Example 20 were dissolved in 4 ml of trifluoroacetic acid (TFA), aged for 1 hr at room temperature and then concentrated to an oily residue by evaporation of the TFA in a stream of N₂. This residue was dissolved in concentrated HCl (2 ml) and the solution evaporated to dryness. The procedure was repeated twice. The product was slurried in 2.5 ml of ethanol:1 ml acetonitrile for 17 hrs, affording pure 4-(1-piperazinyl)-1-methyl-1H-imidazo(4,5-c)pyridine dihydrochloride.

Calcd, for $C_{11}H_{15}N_5$. 2HCl.0.4 H₂O: C, 43.79; H, 6.11; N, 23.21; Cl, 23.50 Found: C, 44.00; H, 6.02; N, 23.00; Cl, 23.40.

200 MHz NMR (D₂O, $\delta$ from TSP): 3.56 (4H, m) 4.40 (4H, m) 7.36 (1H, d, J=5 Hz) 7.82 (1H, d, J=5 Hz) 8.28 (1H, s).

EXAMPLE 22

6-[1-(4-BOC)piperazinyl]-8-bromo-9-methylpurine

To 0.3 g of 6-[1-(4-BOC)piperazinyl]-9-methylpurine (0.94 mmol) in 15 ml of dioxane was added 1.5 g Na₂HPO₄ followed by 15 ml H₂O. After stirring 15 min, 0.10 ml Br₂ (0.312 g; 1.95 mmol) was added dropwise and stirring continued for two days. The mixture was extracted five times with 5 ml portions of CHCl₃, and the combined extracts washed successively with aqueous NaHSO₃, saturated NaCl, dried over anhydrous Na₂SO₄, filtered and evaporated to a yellowish gum. Preparative chromatography on four 20×20 cm×1000μ silica GF plates, developed with EtOAc, afforded 244 mg of a solid product (0.61 mmol; 65% yield). Recrystallization from EtOH gave an analytical sample, mp 151°–152° C.

Calculated for $C_{15}H_{21}N_6OBr$: C, 45.34; H, 5.33; N, 21.16; Br, 20.12. Found: C, 45.21; H, 5.38; N, 20.86; Br, 23.46.

EXAMPLE 23

8-Bromo-9-methyl-6-(1-piperazinyl)purine dihydrochloride

A solution of 100 mg of 6-[1-(4-BOC)piperazinyl]-8-bromo-9-methylpurine (0.25 mmol) in 5 ml absolute EtOH was treated with about 1 ml of ethanolic HCl. After 15 minutes, a white precipitate began to form. After standing overnight the suspension was filtered, but the product was only partially deblocked. Solids and filtrate, after evaporation were combined in about 1 ml trifluoroacetic acid. After 15 minutes, the mixture was evaporated to a gum and partitioned between chloroform and aqueous 10% Na₂CO₃. The aqueous layer was extracted again with chloroform, the combined extracts dried with MgSO₄ and evaporated to a gum. The gum was taken up in about 1 ml of absolute EtOH and treated with about 1 ml of ethanolic HCl. After standing overnight the suspension was filtered, the solid washed successively with EtOH, EtOH/ether, and ether. After drying under a nitrogen stream, 53 mg (0.14 mmol; 56% isolated yield) of a white powder was obtained.

Calculated for $C_{10}H_{13}N_6Br.2HCl.H_2O$: C, 30.94; H, 4.42; N, 21.66; Cl, 20.59. Found: C, 31.09; H, 4.26; N, 21.54; Cl, 20.27.

EXAMPLE 24

6-[1-(4-BOC)piperazinyl]-8-bromopurine

To 5.0 g (16 mmol) of 6-[1-(4-BOC)piperazinyl]purine suspended in 250 ml of dioxane was added, with stirring, a solution of 25 g K₂HPO₄ in 250 ml water, followed after brief stirring by dropwise addition of 1.7 ml Br₂ (5.3 g; 33 mmol). After about 1 hr, the mix was extracted five times with 100 ml portions of chloroform. The combined extracts were washed successively with aqueous NaHSO₃, saturated NaCl, dried over anhydrous Na₂SO₄, filtered and evaporated to give 5.52 g (14.4 mmol) of an orange white solid (90% crude yield). Recrystallization from EtOH provided an analytical sample:

Calculated for $C_{14}H_{19}N_6O_2Br$: C, 43.87; H, 5.00; N, 21.93; Br, 20.85. Found: C, 44.13; H, 5.12; N, 21.68; Br, 20.76.

EXAMPLE 25

6-[1-(4-BOC)piperazinyl]-8-methylaminopurine

A glass bomb liner was charged with 0.5 g of 6-[1-(4-BOC)piperazinyl]-8-bromopurine (1.3 mmol), 25 ml MeOH and ca. 10 ml $H_2NCH_3$, sealed, and heated with gentle agitation for 24 hours at 150° C. The dark mixture that resulted was evaporated to a gum with a $N_2$-stream and purified by preparative tlc on four 20×20 cm×1000μ silica GF plates, developing with 1:10:90-conc. $NH_4OH$:MeOH:$CHCl_3$ to give 204 mg of a brownish gum. This was triturated several times with ether to give 100 mg of a residue which was crystallized from EtOH to give 51 mg (15% yield) of product.

Calculated for $C_{15}H_{23}N_7O_2$: C, 54.04; H, 6.95; N, 29.41. Found: C, 54.17; H, 7.21; N, 28.61.

EXAMPLE 26

8-Bromo-6-(1-piperazinyl)purine dihydrochloride

A solution of 250 mg of 6-[1-(4-BOC)piperazinyl]-8-bromopurine (0.65 mmol) in 8 ml abs. EtOH was treated with 1.5 ml ethanolic-HCl and allowed to stand overnight. The resultant suspension was filtered, and the cake washed successively with EtOH, EtOH/ether, and finally ether. The cake was dried by sucking dry under $N_2$ to give a white powder. A sample dried overnight under high vacuum was submitted for analysis:

Calculated for $C_9H_{11}N_6Br.2HCl$: C, 30.36; H, 3.68; N, 23.60; Br, 22.44; Cl, 19.91. C, 30.19; H, 3.72; N, 22.66; Br, 20.50; Cl, 19.41.

EXAMPLE 27

6-Chloro-2,9-dimethylpurine

This was prepared in a manner similar to that described in Example 9 for 6-chloro-9-methylpurine, except that 5-amino-4-chloro-2-methyl-6-methylaminopyrimidine was used as the starting material and the reaction was carried out at 60° C. for 6 hrs. The title compound was obtained in 97% yield.

EXAMPLE 28

6-[1-(4-BOC)piperazinyl]-2,9-dimethylpurine

6-Chloro-2,9-dimethylpurine (1.0 g; 5.48 mmol) was dissolved in isopentyl alcohol (90 ml) and 1-BOC-piperazine (1.54 g, 8.25 mmol) was added, followed by triethylamine (1.16 ml; 8.25 mmol). This solution was heated under reflux (bath temp 146° C.) overnight. The reaction mixture was evaporated to dryness in vacuo, followed by an additional evaporation from toluene. The residue was dissolved in $CH_2Cl_2$ and the solution was extracted with aqueous 10% $Na_2CO_3$ solution. The organic layer was dried over $MgSO_4$, filtered, and evaporated to dryness. This residue was chromatographed on a column of silica gel 60 (200 g) developed successively with EtOAc (500 ml), EtOAc:MeOH (49:1; 400 ml), EtOAc:MeOH (97:3; 400 ml) and then EtOAc:MeOH (95:5) until completion. Fractions containing the required product were pooled and evaporated to dryness to give a residue which crystallized on standing to give the title compound in quantitative yield.

Calculated for $C_{16}H_{14}N_6O_2$: C, 57.81; H, 7.28; N, 25.28. Found: C, 57.93; H, 7.30; N, 25.12.

EXAMPLE 29

6-[1-(4-BOC)piperazinyl]-8-bromo-2,9-dimethylpurine

To a solution of 1.66 g 6-[1-(4-BOC)piperazinyl]-2,9-dimethylpurine (4.97 mmol) in 90 ml dioxane was added a solution of 9 g $K_2HPO_4$ in 90 ml water, followed after brief stirring, by dropwise addition of 0.5 ml $Br_2$ (1.6 g; 10 mmol). After 5 hours, the mix was extracted five times with 50 ml portions of $CHCl_3$ and the combined extracts washed with aqueous $NaHSO_3$, saturated NaCl, dried over $Na_2SO_4$, filtered and evaporated to give 3.5 g of a pinkish gum. Chromatography on 50 g silica gel packed in $CHCl_3$, was carried out, eluting with $CHCl_3$ and then EtOAc:$CHCl_3$ (1:9). A total of 1.8 g (4.4 mmol; 88% yield) of product, after crystallization from EtOH, was obtained. Recrystallization from EtOH gave material with mp 167°-169° C.

Calculated for $C_{16}H_{23}N_6O_2Br$: C, 46.72; H, 5.64; N, 20.43; Br, 19.43. Found: C, 46.41; H, 5.63; N, 20.14; Br, 19.38.

EXAMPLE 30

6-[1-(4-BOC)piperazinyl]-2,9-dimethyl-8-methylaminopurine

A glass bomb liner was charged with 0.5 g 6-[1-(4-BOC)piperazinyl]-8-bromo-2,9-dimethylpurine (1.2 mmol), 25 ml MeOH and 10 ml $H_2NCH_3$, sealed, and heated at 130° C. for 18 hours with gentle agitation. The recovered solution was concentrated to a gum under a stream of $N_2$, and purified on four 20×20 cm×1000μ silica GF plates, eluting with 0.5:5:95/conc. $NH_4OH$:MeOH:$CHCl_3$ to give 512 mg (1.4 mmol; 94% crude yield). Recrystallization from EtOH/ether gave 191 mg of product, m.p. 209°-211°.

Calculated for $C_{17}H_{27}N_7O_2$: C, 56.49; H, 7.53; N, 27.13. Found: C, 56.64; H, 7.60; N, 27.02.

EXAMPLE 31

6-[1-(4-BOC)piperazinyl]-2,9-dimethyl-8-dimethylaminopurine

A glass bomb liner was charged with 0.4 g of 6-[1-(4-BOC)piperazinyl]-2,9-dimethyl-8-methylaminopurine (0.97 mmol), 30 ml MeOH, and ca. 10 ml $HN(CH_3)_2$, sealed and heated with gentle agitation for 15 hours. The recovered material was concentrated to an oil under a stream of $N_2$ and purified on four 20×20 cm×1000μ silica GF plates, developed with 1:10:90/conc.$NH_4OH$:MeOH:$CHCl_3$, to give 331 mg (0.98 mmol; quantitative) of crude product. Recrystallization from EtOH gave material with mp 157°-159° C.

EXAMPLE 32

2,9-Dimethyl-8-methylamino-6-(1-piperazinyl)purine dihydrochloride

To 175 mg of 6-[1-(4-BOC)piperazinyl]-2,9-dimethyl-8-methylaminopurine (0.48 mmol) was added ca. 0.5 ml of conc. HCl. The mixture foamed initially, then settled to a slightly cloudy solution. After 1 hour, the reaction mixture was concentrated to 0.3 ml under a stream of $N_2$ diluted to 2 ml with 95% EtOH and concentration resumed. When crystallization commenced the solution was stoppered and allowed to stand until complete. After filtration, washing successively with EtOH, EtOH/ether, and finally ether, followed by drying in a $N_2$ stream, 148 mg (0.44 mmol; 92% yield) of product was obtained.

Calculated for $C_{12}H_{19}N_7 \cdot 2HCl \cdot 1.9H_2O$: C, 39.10; H, 6.82; N, 26.60; Cl, 19.24. Found: C, 39.32; H, 6.74; N, 26.56; Cl, 19.03.

EXAMPLE 33

6-[1-(4-BOC)piperazinyl]-2,9-dimethyl-8-(1-pyrrolidinyl)purine

A glass bomb liner was charged with 296 mg of 6-[1-(4-BOC)piperazinyl]-8-bromo-2,9-dimethylpurine (0.72 mmol), 25 ml MeOH, and 10 ml pyrrolidine, sealed, and heated at 130° for 15 hours with gentle agitation. The recovered material was concentrated under a stream of $N_2$ and purified on four $20 \times 20$ cm $\times 1000\mu$ silica GF plates developed with 2:120:80/conc.$NH_4OH$:MeOH:$CHCl_3$ to give 0.277 g (0.69 mmol; 95% yield) of crude product. Recrystallization from EtOH gave material with mp. 197°–199° C.

EXAMPLE 34

6-[1-(4-BOC)piperazinyl]-2,9-dimethyl-8-methoxypurine

A solution of 300 mg 6-[1-(4-BOC)piperazinyl]-8-bromo-2,9-dimethylpurine (0.73 mmol) in 4 ml MeOH was treated with 1 ml of 4M NaOMe in MeOH and then refluxed for 2 hours. After concentration to a gum under a stream of $N_2$, the residue was partitioned between aqueous 10% $NaHCO_3$ and $CHCl_3$ and the aqueous phase was further extracted four more times with $CHCl_3$. The combined organic extracts were dried with $Na_2SO_4$ and evaporated to a cloudy oil which was purified on four $20 \times 20$ cm $\times 1000\mu$ silica GF plates, developed with 1:1 EtOAc:$CHCl_3$ to give 200 mg (0.55 mmol; 75% of crude product). Recrystallization from ether gave 127 mg of pure product, mp. 128°–129° C.

EXAMPLE 35

2,9-Dimethyl-8-dimethylamino-6-(1-piperazinyl)purine dihydrochloride

The procedure used in Example 32 was employed using the corresponding 8-dimethylamino analog (prepared as in Example 31). In this case, the crude product was recrystallized successfully only after excess water was removed by distilling off several portions of absolute EtOH. The final mixture was concentrated and upon standing the product crystallized.

Calculated for $C_{13}H_{21}N_7 \cdot 2HCl \cdot 1.2H_2O$: C, 42.21; H, 6.92; N, 26.51; Cl, 19.17. Found: C, 42.18; H. 6.92; N, 26.39; Cl, 18.99.

EXAMPLE 36

2,9-Dimethyl-6-(1-piperazinyl)-8-(1-pyrrolidinyl)purine dihydrochloride

The process described above in Example 32 was repeated using the 8-(1-pyrrolidinyl) analog (prepared as described in Example 33). As in Example 35, the EtOH azeotropic removal of water was used to encourage crystallization.

Calculated for $C_{15}H_{23}N_7 \cdot 2HCl \cdot 0.2 H_2O$: C, 47.66; H, 6.77; N, 25.95; Cl, 18.76. Found: C, 47.80; H, 6.67; N, 25.93; Cl, 18.65.

EXAMPLE 37

6-[1-(4-BOC)piperazinyl]-8-methoxy-9-methylpurine

A solution of 0.5 g of 6-[1-(4-BOC)piperazinyl]-8-bromo-9-methylpurine (1.26 mmol) in 5.0 ml MeOH was treated with 1.0 ml of 4M NaOMe in MeOH, stirred, and heated under reflux for 1.5 hours. After concentration to a gum under a $N_2$ stream, the residue was partitioned between 10% $NaHCO_3$ and $CHCl_3$, the aqueous phase was extracted three more times with $CHCl_3$, the combined $CHCl_3$ extracts washed with saturated NaCl and dried over $Na_2SO_4$. After filtration and concentration, the residue, 483 mg, was taken up in ether, concentrated to an oil and the process repeated. Finally, the residue was taken up in ether and concentrated by boiling to about 0.8 ml. Upon standing, the product crystallized and, after isolation, weighed 256 mg. (0.74 mmol; 58% yield).

EXAMPLE 38

6-[1-(4-BOC)piperazinyl]-8-dimethylamino-9-methylpurine

A glass bomb liner was charged with 0.4 g of 6-[1-(4-BOC)piperazinyl]-8-bromo-9-methylpurine (1.0 mmol), 30 ml MeOH, and ca. 10 ml $HN(CH_3)_2$, sealed, and heated at 130° C. with gentle agitation for 15 hours. The recovered material was concentrated to an oil under a $N_2$ stream and purified on four $20 \times 20$ cm $\times 1000\mu$ silica GF plates developed with 1:10:90/$NH_4OH$:MeOH:$CHCl_3$ to give 320 mg of a yellowish oil (1.02 mmol; quantitative). It could be crystallized from a highly concentrated solution in MeOH.

EXAMPLE 39

8-Methoxy-9-methyl-6-(1-piperazinyl)purine

To 125 mg of 6-[1-(4-BOC)piperazinyl]-8-methoxy-9-methylpurine (0.36 mmol) was added ca. 0.5 ml of trifluoroacetic acid. After the initial foaming subsided the solution was allowed to stand 15 minutes, then was evaporated under an $N_2$ stream to a thick gum. After repeated dissolution in about 1 ml of MeOH and re-evaporation, the crude product was dried under high vacuum for 15 min. The crude deblocked purine was taken up in ca. 0.5 ml of deionized water and carefully applied to a column of Dowex $1 \times 2$(OH) resin (5 ml). Collection of the eluant was begun and 20 ml of deionized water was run through. The eluate was lyophylized to give 105 mg (quantitative recovery) of a yellowish gum of the title compound as the free base.

EXAMPLE 40

6-[1-(4-BOC)piperazinyl]-9-methyl-8-(1-pyrrolidinyl)purine

A glass bomb liner was charged with 0.4 g 6-[1-(4-BOC)piperazinyl]-8-bromo-9-methylpurine (1.01 mmol), 30 ml of MeOH, and 10 ml of pyrrolidine, sealed, and heated at 130° C. with gentle agitation for 15 hours. The recovered material, after concentration to an oil under a $N_2$ stream, was purified on four $20 \times 20$ cm $\times 1000\mu$ silica GF plates developed with 3.30:70/$NH_4OH$:MeOH:$CHCl_3$ to give 327 mg (0.84 mmol; 83% crude yield) of the title compound. Recrystallization from EtOH gave 146 mg pure product.

EXAMPLE 41

6-[1-(4-BOC)piperazinyl]-9-methyl-8-methylthiopurine

A mixture of 0.4 g 6-[1-(4-BOC)piperazinyl]-8-bromo-9-methylpurine (1.01 mmol), 500 mg thiourea (6.6 mmol), and 5.0 ml MeOH was refluxed for 30 hours. The resultant suspension was cooled to ambient temperature and 1.4 ml of 4M NaOMe in MeOH (5.6 mmol) was added with stirring; a clear solution resulted.

To this was added 0.4 ml of CH₃I (0.91 g; 6.4 mmol) and stirring was continued overnight under a $N_2$ atmosphere. The clear solution obtained was evaporated to a paste under a stream of $N_2$, and the residue was taken up in a mixture of $NaHCO_3/H_2O/CHCl_3$. The aq. phase was further extracted with $CHCl_3$, the extracts combined, dried with $Na_2SO_4$, filtered and evaporated to give a thick yellowish oil. This was separated on silica gel, developed in acetone: $CH_2Cl_2$ (1:4) to give the title compound.

EXAMPLE 42

9-Methyl-6-(1-piperazinyl)-8-(1-pyrrolidinyl)purine dihydrochloride

To 130 mg of 6-[1-(4-BOC)piperazinyl]-9-methyl-8-(1-pyrrolidinyl)purine (0.33 mmol) was added ca. 0.5 ml concentrated HCl. After 15 minutes, the solution was evaporated to a solid under a stream of $N_2$. The residue was taken up in absolute EtOH with heating and the EtOH boiled off to azeotropically dry the product. The process was repeated a second time. The third time, the solution was concentrated and then diluted to 1.0 ml with absolute EtOH. After standing overnight, the crystals were isolated by filtration, washed with EtOH, EtOH/ether, and ether, then dried under $N_2$ to give 78 mg (0.29 mmol; 88% yield) of the title compound as a white powder.

Calculated for $C_{14}H_{21}N_7.2.1HCl.0.5\ H_2O$ C, 45.08; H, 6.52; N, 26.29; Cl, 19.96. Found: C, 44.95; H, 6.12; N, 26.23; Cl, 19.91.

EXAMPLE 43

8-Dimethylamino-9-methyl-6-(1-piperazinyl)purine dihydrochloride

By substituting the appropriate 8-dimethylamino analog (see Example 38) in the reaction described above, (Example 42) the corresponding (title) product was obtained.

Calculated for $C_{12}H_{19}N_7.2.15HCl.0.6H_2O$ C, 41.12; H, 6.43; N, 27.98; Cl, 21.75. Found: C, 41.23; H, 6.16; N, 27.86; Cl, 21.9.

EXAMPLE 44

5-Amino-4-[1-(4-BOC)piperazinyl]-2-methyl-6-methylaminopyrimidine

5-Amino-4-chloro-2-methyl-6-methylaminopyrimidine (1.50 g; 8.7 mmol) and BOC-piperazine (7.50 g; 40.3 mmol) were mixed and heated at 130° C. in a melt. After 24 hrs, an additional 1.0 g of BOC-piperazine was added, and after 48 hrs, a further 2.0 g were added. The reaction was worked up after 55 hrs. total reaction time. The reaction mixture was dissolved in a minimum amount of $CH_2Cl_2$ and absorbed onto a small amount of silica gel 60 by evaporation to dryness. This was placed atop a silica gel column (250 g) which was developed with EtOAc. Fractions containing the required product were pooled and evaporated to dryness to give 17 g of material contaminated with both starting materials. Further chromatography on another column of silica gel 60 (170 g), followed by preparative thick layer plates gave the title compound as a thick syrup (500 mg; 18% yield) contaminated with a trace amount of BOC-piperazine.

EXAMPLE 45

6-[1-(4-BOC)piperazinyl]-2,8,9-trimethylpurine

To the foregoing material prepared in Example 44, (490 mg; 1.6 mmol) in 2-methoxyethanol (2.5 ml) was added acetamidine acetate (378 mg; 3.2 mmol) and the mixture was heated under reflux for 20 hr. Upon cooling, 10% aq. $Na_2CO_3$ was added and the mixture was extracted with EtOAc. The pooled organic layers were dried ($Na_2SO_4$), filtered, and evaporated to dryness. This residue was chromatographed on a column of silica gel 60 (100 g) developed in EtOAc and then a step gradient of MeOH in EtOAc (upto 10% MeOH) to give 340 mg of the title compound (61%) which was slightly contaminated by NMR evaluation. Crystallization from cyclohexane gave material suitable for deblocking.

EXAMPLE 46

6-(1-Piperazinyl)-2,8,9-trimethylpurine dihydrochloride

The foregoing material prepared in Example 45, (97 mg; 0.28 mmol) was dissolved in absolute EtOH (3 ml) and ethanolic HCl (2 ml) was added. This solution was allowed to stand at room temperature for 1 hour and then was blown down to dryness under a stream of nitrogen. Trituration under $Et_2O$ containing a little EtOH gave 79 mg of crude material which contained some impurities. This was recrystallized from abs. EtOH to give 22 mg of impure material, but the mother liquors, after concentration to dryness gave 49 mg of analytically pure product.

Mass spectrum showed molecular ion m/e=246.

Calculated for $C_{12}H_{18}N_6.2HCl.1.2\ H_2O$: C, 42.28; H, 6.62; N, 24.42. Found: C, 42.11; H, 6.46; N, 24.66.

EXAMPLE 47

4-[1-(4-BOC)piperazinyl]-5,6-diamino-2-methylpyrimidine

This was prepared in a manner similar to that described in Example 10 for 4-[1-(4-BOC)piperazinyl]-5,6-diaminopyrimidine except that 6-chloro-4,5-diamino-2-methylpyrimidine was used as the starting material. The title compound was obtained in a yield of 74% after silica gel chromatography.

EXAMPLE 48

6-[1-(4-BOC)piperazinyl]-2,8-dimethylpurine

The foregoing material prepared in Example 47, (450 mg; 146 mmol) was dissolved in 2-methoxyethanol (5 ml) and acetamidine acetate (354 mg; 3 mmol) was added. This solution was heated at reflux for 24 hrs, when tlc indicated completion of the reaction. The mixture was cooled to room temperature and 10% aqu. $Na_2CO_3$ was added, followed by EtOAc. The required product was insoluble and was filtered off and washed with $H_2O$ and then EtOAc, to give 258 mg of the title compound (0.78 mmol, 53% yield).

Calculated for $C_{16}H_{24}N_6O_2.0.6H_2O$: C, 55.98; H, 7.40; N, 24.49. Found: C, 55.61; H, 7.09; N, 24.16.

EXAMPLE 49

2,8-Dimethyl-6-(1-piperazinyl)purine dihydrochloride

The foregoing material (113 mg, 0.34 mmol) was dissolved in hot EtOH (8 ml) and ethanolic HCl (4 ml) was added. After 1 hour at room temperature, the solution was blown down to dryness under a steam of nitrogen and the residue was triturated under $EtOH:Et_2O$ (1:1, 4 ml). The solid so obtained was washed with Et$_2$O and dried to give 107 mg of the title compound. This was recrystallized from EtOH to give 66 mg of product (0.21 mmol, 62%)

Calculated for C$_{11}$H$_{16}$N$_6$.2HCl.0.4 H$_2$O: C, 42.28; H, 6.06; N, 26.9. Found: C, 42.48; H, 5.45; N, 26.48.

EXAMPLE 50

6-[1-(4-BOC)piperazinyl]-2-chloropurine

A solution of 2,6-dichloropurine (10.02 g, 53.0 mmol), BOC-piperazine (11.85 g; 63.6 mmol) and triethylamine (11.08 ml; 79.5 mmol) in absolute EtOH (200 ml) was allowed to stir at room temperature for 40 min. (white precipitate formed) and then was heated at 70°-80° C. (bath-temp) under a reflux condenser, under nitrogen for 3 hours. The mixture was cooled and the precipitate which formed was collected by filtration. Yield 16.27 g (48.02 mmol, 90.6%).

Calculated for C$_{14}$H$_{19}$N$_6$ClO$_2$: C, 49.63; H, 5.65; N, 24.81. Found: C, 49.6; H, 5.69; N, 24.49.

EXAMPLE 51

6-[1-(4-BOC)piperazinyl]-2-chloro-9-methylpurine

6-[1-(4-BOC)piperazinyl]-2-chloropurine (5.76 g, 17.0 mmol) was dissolved in sieve-dried DMF (100 ml) and anhydrous K$_2$CO$_3$ (2.58 g, 18.7 mmol) and methyl iodide (2.12 ml, 340 mmol) were added. This mixture was stirred overnight at room temperature, under a Drierite guard tube. The mixture was evaporated to dryness in vacuo and the residue was partitioned between Et$_2$O and H$_2$O. Some solid remained undissolved and this was filtered off and partitioned between CH$_2$Cl$_2$ and H$_2$O. The total organic layers were pooled and evaporated to dryness to give a white solid residue which was triturated under Et$_2$O and filtered. The solid was air-dried to give 4.14 g of the title compound (69% yield).

Calculated for C$_{15}$H$_{21}$N$_6$ClO$_2$.3H$_2$O: C, 50.29; H, 6.08; N, 23.46. Found: C, 50.58; H, 5.9; N, 23.25.

EXAMPLE 52

2-Chloro-9-methyl-6-(1-piperazinyl)purine hydrochloride

The foregoing material prepared in Example 51, (247 mg, 0.70 mmol) was dissolved in absolute EtOH (8 ml) and to this solution was added EtOH saturated with HCl (3 ml). A solid precipitated immediately and was removed by centrifugation after concentration of the mixture to 4 ml under a stream of nitrogen. Thin layer chromatography of this solid indicated incomplete deblocking and it was treated again with ethanolic HCl for 3 hours. The solid was recovered by filtration, washed with EtOH, and dried to give 124 mg (0.43 mmol; 61% yield) of the title compound.

Calculated for C$_{10}$H$_{13}$N$_6$Cl.HCl.0.4H$_2$O: C, 40.53; H, 5.03 N, 28.36; Cl, 23.92. Found: C, 41.18; H, 4.88; N, 27.81; Cl, 23.78.

EXAMPLE 53

6-[1-(4-BOC)piperazinyl]-9-methyl-2-morpholinopurine

6-[1-(4-BOC)piperazinyl]-2-chloro-9-methylpurine (352.8 mg, 1.0 mmol) was dissolved in distilled morpholine (5 ml) and heated (bath-temp. 150° C.) under N$_2$ for 27 hours. The reaction mixture was cooled to room temperature and then evaporated to dryness in vacuo (several times from toluene to remove the last traces of morpholine). The residue was dissolved in a minimum amount of CH$_2$Cl$_2$ and absorbed onto silica gel 60. This was placed on top of a silica gel 60 column (40 g) packed in hexanes. The column was developed successively with EtOAc:hexanes (2:3), EtOAc:hexanes (1:1), and finally with EtOAc:hexanes (3:2). Fractions containing the required product were pooled and evaporated to dryness to give 368 mg (91% yield) of the title compound.

Calculated for C$_{19}$H$_{29}$N$_7$O$_3$.0.35H$_2$O: C, 55.64; H, 7.29; N, 23.91. Found: C, 55.92; H, 6.84; N, 23.52.

EXAMPLE 54

9-Methyl-2-morpholino-6-(1-piperazinyl)purine dihydrochloride

The foregoing material prepared in Example 63, (310 mg; 0.77 mmol) was dissolved in absolute EtOH (7 ml) and EtOAc (2 ml), with warning. To this solution was added EtOH saturated with HCl (4 ml) and the mixture was left at room temperature for 1 hour. The mixture was concentrated to 5 ml under a stream of nitrogen and Et$_2$O (5 ml) was added. The solid so formed was isolated by centrifugation and washed 3 times with Et$_2$O to give the title compound in good yield.

Calculated for C$_{14}$H$_{21}$N$_7$O.2HCl: C, 44.68; H, 6.16; N, 26.06. Found: C, 44.75; H, 6.39; N, 25.75.

EXAMPLE 55

6-[1-(4-BOC)piperazinyl]-9-methyl-2-pyrrolidinylpurine

6-[1-(4-BOC)piperazinyl]-2-chloro-9-methylpurine (0.396 g; 1.12 mmol) was dissolved in EtOH (15 ml) and pyrrolidine (10 ml) was added. This solution was heated under reflux (bath temp 120°-130° C.) for 6 hours and allowed to cool to room temperature. The mixture was evaporated to dryness and the residue was separated between CH$_2$Cl$_2$ (70 ml) and 10% aq. Na$_2$CO$_3$ (70 ml). The aq. layer was washed two more times with CH$_2$Cl$_2$ (2×70 ml) and the pooled organic layers were dried (MgSO$_4$), filtered, and evaporated to dryness in vacuo to give 0.45 g (quantitative yield) of the title compound as a white powder.

Calculated for C$_{19}$H$_{29}$N$_7$O$_2$.0.3H$_2$O: C, 58.08, H, 7.65, N, 24.96. Found: C, 58.35; H, 7.56; N, 24.69.

EXAMPLE 56

9-Methyl-6-(1-piperazinyl)-2-pyrrolidinylpurine dihydrochloride

The foregoing material prepared in Example 55, (0.41 g; 1.06 mmol) was dissolved in EtOAc (30 ml) and ethanolic HCl (15 ml) was added. After standing at room temperature for 1½ hour, the solution was blown down under a stream of nitrogen to a syrup. This was triturated under EtOH—Et$_2$O (8 ml) to give a white powder which was washed with Et$_2$O and dried in vacuo to give 315.3 mg (0.87 mmol; 83%) of the title compound.

Calculated for C$_{14}$H$_{21}$N$_7$.2HCl.0.25H$_2$O C, 46.10; H, 6.49; N, 26.88. Found: C, 46.11; H, 6.32; N, 26.55.

EXAMPLE 57

6-[1-(4-BOC)piperazinyl]-9-methyl-2-methylaminopurine

A suspension of 6-[1-(4-BOC)piperazinyl]-2-chloro-9-methylpurine (0.250 g; 0.71 mmol) in EtOH (6 ml) was cooled to 0° and added to anhydrous methylamine (3 ml) condensed in a pressure table. The tube was sealed and sealed at 110° C. for 5½ hours. After cooling to room temperature, CH₂Cl₂ and 10% aq. Na₂CO₃ were added and the layers were separated. The aqueous layer was washed two more times with CH₂Cl₂ and the pooled organic layers were dried (MgSO₄), filtered and evaporated to dryness. The residue was recrystallized from CH₂Cl₂ (5 ml)-hexanes (20 ml) to give 150 mg (0.45 mmol, 63%) of the title compound in two crops.

Calculated for $C_{16}H_{25}N_7O_2$: C, 55.31; H, 7.25; N, 28.22. Found: C, 55.46; H, 7.22; N, 28.31.

EXAMPLE 58

9-Methyl-2-methylamino-6-(1-piperazinyl)purine dihydrochloride

This was prepared from the foregoing compound prepared in Example 57 by deblocking with ethanolic HCl in the usual fashion.

Calculated for $C_{11}H_{17}N_7 \cdot HCl$: C, 41.26; H, 5.98; N, 30.62. Found: C, 41.07; H, 6.05; N, 30.29.

EXAMPLE 59

6-[1-(4-BOC)piperazinyl]-2-dimethylamino-9-methylpurine

Method A

6-[1-(4-BOC)piperazinyl]-2-chloro-9-methylpurine (0.49 g; 1.41 mmol) was dissolved in EtOH (15 ml), chilled, and added to 10 ml of anhydrous dimethylamine (condensed at −78° C.) in a Fischer-Porter tube. The tube was sealed and heated at 120°–130° for 5 hours. After cooling to room temperature, the reaction mixture was evaporated to dryness to give a white residue of 0.58 g. This was separated between CH₂Cl₂ (70 ml) and 10% aq. Na₂CO₃ (70 ml) and the aqueous layer was washed two more times with CH₂Cl₂ (2×70 ml). The pooled organic layers were dried (MgSO₄), filtered, and evaporated to dryness to give 0.50 g (1.38 mmol, 98%) of the title compound.

Calculated for: $C_{17}H_{27}N_7O_2$: C, 56.49; H, 7.53; N, 27.13. Found: C, 56.65; H, 7.58; N, 26.95.

Method B

6-[1-(4-BOC)piperazinyl]-2-chloro-9-methylpurine (0.352 g; 1.0 mmol) was dissolved in n-butanol (30 ml) and 40% aq. dimethylamine (10 ml) was added. This mixture was heated in a sealed tube at 150° C. for 24 hours, at which point tlc indicated no starting material remaining, but two products were apparent. The reaction mixture was blown down under a stream of nitrogen and then was evaporated to dryness. This residue was absorbed onto silica gel 60 from a methanolic solution, and then was fractionated on a silica gel 60 column (30 g). The column was developed first with EtOAc:-hexanes (1:1) to give 110 mg (30% yield) of the title compound identical by tlc and NMR with that prepared by Method A (above).

Calculated for: $C_{17}H_{27}N_7O_2$: C, 56.49; H, 7.53; N, 27.13. Found: C, 56.83; H, 7.65; N, 26.99.

Further development of the column with CH₂Cl₂:MeOH 9:1 gave 180 mg (69% yield) of 2-dimethylamino-9-methyl-6-(1-piperazinyl)purine as the free base.

EXAMPLE 60

2-Dimethylamino-9-methyl-6-(1-piperazinyl)purine dihydrochloride

Method A

The free base of the title compound obtained by Method B in the foregoing example (Example 59) (165 mg; 0.63 mmol) was dissolved in EtOH (4 ml) and ethanolic HCl (2 ml) was added. The solution was blown down under a stream of nitrogen and the residue was triturated under EtOH (2 ml). A solid formed which was washed with EtOH (0.5 ml) and then Et₂O before being dried in vacuo overnight at 40° C. to give 96 mg (0.27 mmol) of the title compound.

Calculated for $C_{12}H_{19}N_7 \cdot 2HCl \cdot 1.3H_2O$: C, 40.30; H, 6.64; N, 27.42. Found: C, 40.34; H, 6.30; N, 27.06.

Method B

6-[1-(4-BOC)piperazinyl]-2-dimethylamino-9-methylpurine (50 mg; 0.14 mmol) was dissolved in EtOH (4 ml) and ethanolic HCl (2 ml) was added. After 1 hour at room temperature, the solution was blown down to about 1 ml under a stream of nitrogen. Product precipitated and an additional 2 ml of Et₂O was added. The solid was washed by centrifugation with Et₂O (2×2 ml) and dried at 40° in vacuo to give 42 mg (0.13 mmol, 93%) of the title compound identical in all respects to that prepared by Method A (above).

EXAMPLE 61

6-[1-(4-BOC)piperazinyl]-8-bromo-2-dimethylamino-9-methylpurine

6-[1-(4-BOC)piperazinyl]-2-dimethylamino-9-methylpurine (0.48 g; 133 mmol) was dissolved in dioxane (25 ml), with warming, and a solution of K₂HPO₄ 2.39 g) in H₂O (25 ml) was added. To this well-stirred solution was added bromine (0.2 ml), dropwise over a period of 1–2 min. After 45 min. at room temperature, the reaction was blown under a stream of nitrogen and evaporated to dryness. The residue so obtained was separated between CH₂Cl₂ (60 ml) and 10% aq. Na₂CO₃ (60 ml), and the aqueous layer was washed two more times with 60 ml of CH₂Cl₂. The pooled organic layers were dried (MgSO₄), filtered, and evaporated to dryness to give 0.44 g. This residue was purified by chromatography on silica gel 60 using CH₂Cl₂ and a step gradient of EtOH in CH₂Cl₂ as developing solvents, and then rechromatography using EtOAc-hexanes, gave 198.2 mg of the title compound in 34% yield.

Calculated for $C_{17}H_{26}N_7O_2Br$: C, 46.37; H, 5.95; N, 22.27. Found: C, 46.57; H, 5.98; N, 22.08.

EXAMPLE 62

6-[1-(4-BOC)piperazinyl]-2,8-bis(dimethylamino)-9-methylpurine

The foregoing material prepared in Example 61, (198.2 mg; 0.45 mmol) was dissolved in n-butanol (10 ml), with warming, and added to anhydrous dimethylamine (10 ml) (condensed at −78° C.) in a pressure bottle. This solution was sealed and heated at 120°–130° C. for 4 hours. TLC indicated the reaction to be incomplete, and an additional 10 ml of condensed dimethylamine was added and the reaction continued overnight. The mixture was then cooled to room temperature, blown down to small volume under a stream of nitrogen, and evaporated to dryness. This residue was separated between CH₂Cl₂ (60 ml) and 10% aq. Na₂CO₃ (60 ml) and the aqueous layer was washed two more times (2×60 ml) with CH₂Cl₂. The pooled organic layers were dried (MgSO₄), filtered, and evaporated to dryness. This residue was chromatographed on a column (2×36 cm) of silica gel 60 developed successively with a step gradient of EtOAc in hexanes (10% increments starting with EtOAc:hexanes 1:9). Fractions containing the required product were pooled and evaporated to dryness to give a quantitative yield of the title compound as a clear glass which solidified on standing overnight.

Calculated for $C_{19}H_{32}N_8O_2.0.25H_2O$: C, 55.79; H, 8.01; N, 27.4. Found: C, 55.91; H, 7.65; N, 27.31.

EXAMPLE 63

2,8-Bis(dimethylamino)-9-methylpurine dihydrochloride

The foregoing material (180 mg; 0.44 mmol) was dissolved in EtOH (5 ml) and ethanolic HCl (5 ml) was added. After standing at room temperature for 15 minutes, the solution was slowly blown down to a syrup under a stream of nitrogen. This residue was triturated under EtOH-Et₂O (8 ml) and the solid so formed was isolated and washed with Et₂O to give 121.3 mg (0.32 mmol; 73%) of the title compound. An analytical sample was obtained by reconversion to the free base (extraction into CH₂Cl₂ from 10% aq. Na₂CO₃), followed by re-conversion to the dihydrochloride salt by treatment with ethanolic HCl.

Calculated for $C_{14}H_{24}N_8.2HCl.0.4H_2O$: C, 43.73; H, 7.03; N, 29.14. Found: C, 43.95; H, 6.95; N, 28.83.

EXAMPLE 64

6-[1-(4-BOC)piperazinyl]-2-methoxy-9-methylpurine

Sodium spheres (110 mg, 4.8 mmol) were dissolved in anhydrous methanol (10 ml) and 6-[1-(4-BOC)-piperazinyl]-2-chloro-9-methylpurine (430 mg, 1.2 mmol) was added. This mixture was heated under reflux under nitrogen for 4 days and then allowed to cool to room temperature. The reaction was neutralized with glacial acetic acid and evaporated to dryness in vacuo to give a white residue. This was adsorbed onto silica gel 60 and placed on top of a silica gel 60 column (90 ml), packed in hexanes. The column was developed successively with EtOAc:hexanes (1:4), EtOAc:hexanes (3:7), EtOAc:hexanes (1:1) and finally, EtOAc:hexanes (3:2). Fractions containing the required product were pooled and evaporated to dryness to give a residue which was triturated under hexanes to give a 64% yield of the title compound as a white solid.

Calculated for $C_{16}H_{24}N_6O_3$: C, 55.16; H, 6.94; N, 27.12. Found: C, 55.34; H, 6.84; N, 24.06.

EXAMPLE 65

2-Methoxy-9-methyl-6-(1-piperazinyl)purine dihydrochloride

The foregoing compound prepared in Example 64, (2.1 mg, 0.6 mmol) was dissolved in absolute EtOH (5 ml) with warming. To this solution was added EtOH saturated with HCl (2 ml) and after 1 hour the solution was concentrated to 4 ml under a stream of nitrogen. The white precipitate so formed was collected by centrifugation and washed with Et₂O (4×2 ml). Re-working of the supernatants gave 51 mg (0.16 mmol; 26%) in total, of the title compound, m.p. >280° C.

Calculated for $C_{11}H_{16}N_6O.2HCl.1.25H_2O$: C, 38.44; H, 6.01; N, 24.45. Found: C, 38.44; H, 5.88; N, 26.16.

EXAMPLE 66

6-[1-(4-BOC)piperazinyl]-9-methyl-2-(2-propoxy)purine

Sodium spheres (92 mg, 4 mmol) were dissolved in 2-propanol (9 ml) and 6-[1-(4-BOC)piperazinyl]-2-chloro-9-methylpurine (352.8 mg; 1 mmol) was added. This mixture was heated under reflux under nitrogen for 3 days and then was evaporated to dryness in vacuo. The residue was partitioned between CH₂Cl₂ and H₂O and the organic layer was dried (MgSO₄), filtered, and evaporated to dryness. This residue was adsorbed onto silica gel 60 and placed on top of a silica gel 60 column (50 g), packed in hexanes. The column was developed successively with EtOAc:hexanes (1:3), EtOAc:hexanes (1:1), and finally with EtOAc:hexanes (3:2). Fractions containing the required product were pooled and evaporated to dryness to give 214 mg of the title compound (57% yield).

Calculated for $C_{18}H_{18}N_6O_3.0.25\ H_2O$: C, 56.75; H, 7.54; N, 22.06. Found: C, 56.73; H, 7.35; N, 21.66.

EXAMPLE 67

9-Methyl-6-(1-piperazinyl)-2-(2-propoxy)purine dihydrochloride

The foregoing material prepared in Example 66, (204 mg, 0.54 mmol) was dissolved in absolute EtOH (5 ml) and to this solution was added ethanolic HCl (3 ml). After 1 hour at room temperature, this solution was concentrated to 4 ml under a stream of nitrogen. Ether (4 ml) was added and the white solid so formed was isolated by centrifugation and washed well (3×) with ether. Yield 132 mg (2 crops), 71% yield.

Calculated for $C_{13}H_{20}N_6O.2HCl.1.15\ H_2O$: C, 42.20; H, 6.60; N, 22.72. Found: C, 41.97; H, 6.18; N, 22.61.

EXAMPLE 68

6-[1-(4-BOC)piperazinyl]-2-dimethylaminopurine

A suspension of 6-[1-(4-BOC)piperazinyl]-2-chloropurine (0.25 g; 0.74 mmol) in EtOH (6 ml) was cooled to 0° and added to anhydrous dimethylamine (3 ml) condensed in a pressure bottle. The bottle was sealed and heated at 110° C. for 5½ hr. The mixture became homogeneous as the reaction progressed. At completion of the reaction, the tube was cooled and the mixture was blown down under a stream of nitrogen. The residue was partitioned between CH₂Cl₂ and 10% aq. Na₂CO₃ and the organic phase was dried (MgSO₄), filtered, and evaporated to dryness. Further separation between CH₂Cl₂ and 10% aq. Na₂CO₃, followed by re-working of the organic phase as described above, gave the title compound in 97% yield (250 mg; 0.71 mmol).

Calculated for $C_{16}H_{25}N_7O_2$: C, 55.31; H, 7.25; N, 28.22. Found: C, 54.95; H, 7.25; N, 28.51.

EXAMPLE 69

2-Dimethylamino-6-(1-piperazinyl)purine dihydrochloride

The foregoing material prepared in Example 68, (220 mg; 0.63 mmol) was dissolved in hot EtOH (20 ml) and cooled to room temperature. Ethanolic HCl (10 ml) was added and the mixture was allowed to stand at room temperature for 1 hour (product started to precipitate after about 30 min.). The mixture was then blown down to about 10 ml under a stream of nitrogen and then Et$_2$O (10 ml) was added. The precipitated product was filtered off and washed with Et$_2$O. Yield 0.218 g (quantitative yield)

Calculated for C$_{11}$H$_{17}$N$_7$.2HCl.2.8 H$_2$O C, 35.64; H, 6.4; N, 26.45. Found: C, 35.39; H, 6.02; N, 26.3.

EXAMPLE 70

2-Chloro-6-[1-(4-methylpiperazinyl)]purine 2,6-Dichloropurine (4.53 g; 24 mmol) was dissolved in EtOH (100 ml) and N-methylpiperazine (2.9 g, 29 mmol) was added, followed by triethylamine (5.01 ml, 36 mmol). This mixture was heated under reflux for 45 min. (tlc after 15 min showed traces of starting material). Upon cooling to room temperature, the product precipitated and was filtered off and dried. Yield 5.8 g (23 mmol, 96%)

Calculated for C$_{10}$H$_{17}$N$_6$Cl: C, 47.53; H, 5.18; N, 33.26. Found: C, 47.43; H, 5.34; N, 33.03.

EXAMPLE 71

2-Dimethylamino-6-[1-(4-methylpiperazinyl)]purine dihydrochloride

The foregoing material prepared in Example 70, (0.7 g; 2.77 mmol) was added to anhydrous dimethylamine (5 ml; condensed in a pressure tube) and chilled EtOH (8 ml) was added. The tube was sealed and heated at 110° C. for 5½ hours, during which time dissolution occurred. Upon cooling to room temperature a solid formed and the cooled mixture was blown down to dryness under a stream of nitrogen. The residue was dissolved in CH$_2$Cl$_2$ and extracted with 10% aq. Na$_2$CO$_3$ and the organic phase was dried (MgSO$_4$), filtered and evaporated to dryness to give 0.65 g (2.49 mmol; 90% yield) of the title compound as the free base. A portion, 0.1 g (0.38 mmol), of this material was dissolved in hot EtOH (8 ml) and cooled to room temperature. Ethanolic HCl (4 ml) was added and the product started to precipitate out after ca. 5 min. After 1 hour, the solution was blown down under a stream of nitrogen and the residue was triturated under EtOH-Et$_2$O. The precipitated product was filtered and washed with Et$_2$O. Yield 0.122 g (0.37 mmol; 97% from free base).

Calculated for C$_{12}$H$_{19}$N$_7$.2HCl.2.4 H$_2$O: C, 38.17; H, 6.88; N, 25.97. Found: C, 37.89; H, 6.45; N, 25.76.

EXAMPLE 72

2-Dimethylamino-9-methyl-6-[1-(4-methylpiperazinyl)-]purine dihydrochloride

The free base of the foregoing material prepared in Example 71, (150 mg; 0.58 mmol) was dissolved in sieve-dried DMF (10 ml) and NaH (60% in oil; 40 mg, 24 mg of NaH, 1 mmol) was added. This mixture was stirred at room temperature under N$_2$ until evolution of hydrogen gas had ceased (20 min). Methyl iodide (0.043 ml; 0.7 mmol) was then added and the mixture was stirred at room temperature for 3½ hr. The mixture was then evaporated to dryness in vacuo and the residue was adsorbed onto a minimum amount of silica gel 60 by evaporation of a methanolic solution. This was placed atop a silica gel 60 column (20 g) packed in CH$_2$Cl$_2$ which was developed successively with MeOH:CH$_2$Cl$_2$ 5:95 and then MeOH:CH$_2$Cl$_2$ 1:9. Fractions containing the required product were pooled and evaporated to dryness to give 163 mg (quantitative yield) of the title compound as the free base.

0.115 g (0.42 mmol) of this material was dissolved in hot EtOH (8 ml) and cooled to room temperature. Ethanolic HCl (4 ml) was added and after 30 min at room temperature the mixture was blown down to dryness under a stream of nitrogen. Trituration under EtOH-Et$_2$O gave the title compound which was filtered off and washed with Et$_2$O. After drying, 85 mg (0.24 mmol, 57%) was obtained.

Calculated for C$_{13}$H$_2$,N$_7$.2HCl.H$_2$O C, 42.62; H, 6.88; N, 26.77. Found: C, 42.39; H, 6.73; N, 26.43.

EXAMPLE 73

2-Amino-6-(1-piperazinyl)purine dihydrochloride

2-Amino-6-chloropurine (508 mg, 3.00 mmol) was suspended in sieve-dried DMF (20 ml) and piperazine (516 mg; 5.99 mmol) was added. Dissolution occurred and the mixture was heated at 100° C. overnight under nitrogen. A precipitate formed which was filtered off and washed with Et$_2$O (yield, 380 mg). A portion (50 mg) was dissolved in 2N HCl (1 ml) and centrifuged, the supernatant was removed and cooled in an ice-bath and the crystalline product (40 mg) was isolated by centrifugation and dried in vacuo at 70° C. for 12 hours over P$_2$O$_5$.

Calculated for C$_9$H$_{13}$N$_7$.2HCl.0.69 H$_2$O: C, 35.49; H, 5.42; N, 32.20; Cl, 23.28. Found: C, 35.74; H, 5.36; N, 31.97; Cl, 23.2.

EXAMPLE 74

6-[1-(4-BOC)piperazinyl]-2-chloro-9-(1-propyl)purine

The material prepared in Example 50 (3.73 g, 11.0 mmol) was dissolved in sieve dried DMF (100 ml) and 60% NaH in oil (660 mg, 16.5 mmol of NaH) was added and the mixture was stirred under nitrogen until the effervescence ceased. 1-Iodopropane (1.23 ml, 12.65 mmol) was added and the reaction was stirred at room temperature overnight. The mixture was evaporated to dryness in vacuo and the residue was dissolved in CH$_2$Cl$_2$ and this solution was washed with 10% aqu. Na$_2$CO$_3$, dried over MgSO$_4$, filtered and evaporated to a yellow oil. This was dissolved in a little CH$_2$Cl$_2$ and chromatographed on a silica gel 60 column (200 ml) packed in EtOAc:hexanes (1:2). The column was developed successively with EtOAc:hexanes (1:2) and EtOAc:hexanes (1:1) and fractions containing the required product were pooled and evaporated to dryness to give a syrup which crystallized upon trituration. These white crystals were triturated under hexane and filtered. Yield 2.85 g (74.8 mmol, 68%). Mp 105°-106.5° C.

Calculated for C$_{17}$H$_{25}$N$_6$O$_2$Cl: C, 53.61; H, 6.62; N, 22.06. Found: C, 53.39; H, 6.47; N, 22.06.

EXAMPLE 75

6-[1-(4-BOC)piperazinyl]-2-methoxy-9-(1-propyl)purine

The foregoing material prepared in Example 74 (72.52 g, 0.17 mol) was dissolved in methanol (1.06 L) and 122 ml of 4.38M methanolic sodium methoxide was added. This solution was heated under reflux under N$_2$ for 48 hrs. and then additional sodium methoxide (12 ml) was added, followed by another 6 ml after a further 24 hrs. After 96 hrs total reaction, the mixture was evaporated to dryness and the residue was partitioned between $CH_2Cl_2$ (1 L) and $H_2O$ (400 ml). The aqueous layer was washed with $CH_2Cl_2$ (2×500 ml) and the pooled organic layers were dried ($MgSO_4$), filtered and evaporated to dryness. Purification was effected on a silica gel 60 column (2.1 kg) developed with a step gradient (1:4 to 1:1) of EtOAc:hexanes. Fractions containing the required product were pooled and evaporated to dryness to give 52 g (0.138 mol, 81%) of the title compound.

Calculated for $C_{18}H_{28}N_6O_3$: C, 57.43; H, 7.50; N, 22.33. Found: C, 57.58; H, 7.66; N, 22.33.

EXAMPLE 76

2-Methoxy-6-(1-piperazinyl)-9-(1-propyl)purine dihydrochloride

The foregoing material prepared in Example 75 (51.5 g, 0.137 mmol) was dissolved in MeOH (1.5 L) and 1.5 L of methanolic HCl was added carefully. This mixture was stirred at room temperature for 1½ hr. and then was concentrated first under a stream of $N_2$ and then on an evaporator to 600 ml. Precipitation occurred and $Et_2O$ (IL) was added. The white solid was filtered off and washed well with $Et_2O$. Yield 39.4 g, and a second crop gave 3.54 g. Total yield 0.123 mol, 90%. Mp 205°–207° C.

Calculated for $C_{13}H_{20}N_6O \cdot 2HCl$: C, 44.70; H, 6.35; N, 24.06; Cl, 20.3. Found: C, 44.50; H, 6.50; N, 23.98; Cl, 20.64.

EXAMPLE 77

6-[1-(4-BOC)piperazinyl]-2-methylthio-9-(1-propyl)purine

The material prepared in Example 74 (300 mg, 0.76 mmol) was dissolved in t-butanol (10 ml) and sodium methylthiolate (213 mg, 3.04 mmol) was added. This mixture was refluxed under $N_2$ for 48 hrs. and then volatiles were removed under a stream of $N_2$. The residue was taken up in $CH_2Cl_2$ (100 ml) and 10% aqueous $Na_2CO_3$ (20 ml) and the layers were separated. The aqueous layer was washed two more times with $CH_2Cl_2$ (2×20 ml) and the pooled organic layers were dried ($MgSO_4$), filtered, and evaporated to dryness. This residue was dissolved in a little EtOAc and passed onto a silica gel 60 column (20 g), packed and developed with EtOAc. Fractions containing the required product were pooled and evaporated to dryness to give 177 mg (0.45 mmol, 59%) of chromatographically pure product.

Calculated for $C_{18}H_{28}N_6O_2S$: C, 55.08; H, 7.19; N, 21.41. Found: C, 55.31; H, 7.18; N, 21.18.

EXAMPLE 78

2-Methylthio-6-(1-piperazinyl)-9-(1-propyl)purine dihydrochloride

The foregoing material prepared in Example 77 (150 mg, 0.38 mmol) was dissolved in EtOH (7.5 ml) and ethanolic HCl (3.5 ml) was added. After standing at room temperature for 1 hr, the mixture was concentrated to 1 ml under a stream of $N_2$. Precipitation of the product was completed by the addition of $Et_2O$ (4 ml) and the title compound was filtered and washed with $Et_2O$ (2×2 ml). Yield 126 mg (0.34 mmol, 89%).

Calculated for $C_{13}H_{20}N_6S \cdot 2HCl$: C, 42.74; H, 6.07; N, 23.01. Found: C, 42.69; H, 6.06; N, 22.68.

EXAMPLE 79

6-[1-(4-BOC)piperazinyl]-2-chloro-9-(methoxymethyl)-purine

The material prepared in Example 50 (1.02 g, 3.0 mmol) was dissolved in sieve dried DMF (25 ml) and 60% NaH in oil (180 mg, 4.5 mmol of NaH) was added and the mixture was stirred under $N_2$. When a homogeneous solution was obtained, bromomethyl methyl ether (0.27 ml, 3.3 mmol) was added and the mixture was left stirring at room temperature under $N_2$ overnight. Additional bromomethyl methyl ether (0.05 ml) was added followed, at hourly intervals, by two additional 24 mg amounts of 60% NaH in oil. Cold $H_2O$ (25 ml) was added slowly, followed by 10% aqueous $Na_2CO_3$ (10 ml). After stirring for 1½ hr., the mixture was evaporated to dryness in vacuo and the residue was partitioned between 10% aqueous $Na_2CO_3$ and $CH_2Cl_2$. The organic layer was separated, filtered, and adsorbed onto a small amount of silica gel 60. This was placed atop a dry packed silica gel 60 column (80 ml) which was developed with a step gradient (from 1:4 to 1:1) of EtOAc:hexanes. Fractions containing the required product were pooled and evaporated to dryness to give 927 mg (2.42 mmol, 80%) of an oil which crystallized on standing. Mp 108°–110°.

Calculated for $C_{16}H_{23}N_6O_3Cl$: C, 50.20; H, 6.06; N, 21.95. Found: C, 50.28; H, 6.1; N, 22.05.

EXAMPLE 80

6-[1-(4-BOC)piperazinyl]-2-ethoxy-9-(methoxymethyl)-purine

Sodium spheres (83 mg, 3.6 mmol) were added to abs. EtOH (5 ml) and after hydrogen evolution had ceased, 354 mg (0.92 mmol) of material from the foregoing Example 79 in 5 ml of EtOH was added. This solution was heated under reflux overnight under $N_2$. The mixture was cooled and carefully neutralized with acetic acid before being evaporated to dryness. This residue was partitioned between $CH_2Cl_2$ and 10% aqueous $Na_2CO_3$ and a little EtOAc was then added to the $CH_2Cl_2$ layer to effect total dissolution. After drying ($MgSO_4$) and filtration, the filtrate was evaporated to an oil (310 mg, 86%) which crystallized on standing. Trituration under $Et_2O$ and then evaporation of the mixture gave 257 mg (0.65 mmol, 71%) of product, mp 115°–116.6° C.

Calculated for $C_{18}H_{28}N_6O_4$: C, 55.09; H, 7.19; N, 21.41. Found: C, 55.20; H, 7.31; N, 21.1.

EXAMPLE 81

2-Ethoxy-9-methoxymethyl-6-(1-piperazinyl)purine maleate

The foregoing material prepared in Example 80 (255 mg, 0.65 mmol) was dissolved in $CF_3COOH$ (4 ml) and stirred at room temperature for 40 min. The mixture was concentrated and to the residual oil was added a small amount of Dowex 1×2(OH) resin, followed by 1 drop of conc. NaOH (to ensure basicity). This total mixture was then poured onto a Dowex 1×2(OH) column and developed with $H_2O$. Fractions containing the required product were pooled and evaporated to give 70 mg (0.24 mmol) of the title compound as the free base. This was dissolve din EtOH (2 ml) and 56 mg (0.49 mmol) of maleic acid in EtOH (3 ml) was added. The solution was concentrated under a stream of $N_2$ until precipitation was observed. This solid was removed by centrifugation and washed with Et$_2$O (2×3 ml). Yield 81 mg (0.20 mmol), more product was apparent in the supernatants.

Calculated for $C_{13}H_{20}N_6O_2 \cdot C_4H_4O_4$: C, 50.00; H, 5.92; N, 20.58. Found: C, 49.94; H, 5.92; N, 20.55.

EXAMPLE 82

6-[1-(4-BOC)piperazinyl]-2-chloro-9-(ethoxymethyl)-purine

The material prepared in Example 50 (847 mg, 2.5 mmol) was dissolved in sieve dried DMF (25 ml) and 60% NaH in oil (105 mg, 2.62 mmol of NaH) was added. After 20 minutes stirring under N$_2$, evolution of H$_2$ had ceased and chloromethyl ethyl ether (0.255 ml, 2.75 mmol) was added. After 3 hrs at room temperature, tlc indicated complete reaction and the mixture was concentrated at 65° under a stream of N$_2$ (with NaHCO$_3$ outlet tube). The mixture was then evaporated to dryness and the residual oil was partitioned between CH$_2$Cl$_2$ and 10% aqueous Na$_2$CO$_3$. The organic layer was dried (MgSO$_4$), filtered, and evaporated to a viscous oil. This material was chromatographed on a silica gel 60 column (150 ml) packed in EtOAc:hexanes (1:4) and developed with a step gradient of EtOAc:hexanes (from 1:4 to 1:1). Fractions containing the required product were pooled and evaporated to dryness to give 620 mg (1.56 mmol, 62.5%) of the title compound, mp 102°–104° C.

Calculated for $C_{17}H_{25}N_6O_3Cl$: C, 51.45; H, 6.35; N, 21.18 Found: C, 51.28; H, 6.42; N, 20.86

EXAMPLE 83

6-[1-(4-BOC)piperazinyl]-9-ethoxymethyl-2-methoxypurine

The foregoing material prepared in Example 82 (300 mg, 0.75 mmol) was added to a solution of methanolic sodium methoxide (0.69 ml of 4.37M solution) in methanol (6 ml) and the mixture was heated under reflux under N$_2$ for 42 hrs. The solution was then cooled and carefully neutralized with acetic acid before being evaporated to dryness. This residue was partitioned between CH$_2$Cl$_2$ and 10% aqueous Na$_2$CO$_3$ and the organic layer was dried (MgSO$_4$), filtered and evaporated to dryness. This residue was purified by chromatography on a silica gel 60 column (50 ml) developed in EtOAc:hexanes (3:7) to give the title compound as a tlc pure viscous clear oil (259 mg, 0.66 mmol, 88%). Mass spec. (FAB) showed M$^+$+H at 393 m/e.

EXAMPLE 84

9-Ethoxymethyl-2-methoxy-6-(1-piperazinyl)purine maleate

The foregoing material prepared in Example 83 (170 mg, 0.43 mmol) was dissolved in CF$_3$COOH (3 ml) and stirred at room temperature for 30 min before being concentrated to dryness. To this residual liquid was added a small amount of Dowex 1×2(OH) resin in H$_2$O and the slurry was placed atop a Dowex 1×2(OH) column which was then developed with H$_2$O. Fractions containing the required product were pooled and evaporated to dryness in vacuo to give 37 mg (0.13 mmol, 29%) of the product as its free base. This was dissolved in EtOH (7 ml) containing maleic acid (29.9 mg, 0.26 mmol) and the solution was concentrated under a stream of N$_2$ to give a residual oil. Trituration under Et$_2$O gave a gummy solid which was further washed with EtOAc to give 37.8 mg of the title compound. Mass spec. (EI) showed M$^+$ (free base) at 292 m/e.

Calculated for $C_{13}H_{20}N_6O_2 \cdot C_4H_4O_4$: C, 49.99; H, 5.92; N, 20.58. Found: C, 49.97; H, 5.66; N, 20.4.

EXAMPLE 85

6-[1-(4-BOC)piperazinyl]-2-chloro-9-(cyclopropylmethyl)purine

The material prepared in Example 50 (1.02 g, 3.0 mmol) was dissolved in sieve dried DMF (25 ml) and 180 mg of 60% NaH in oil (4.5 mmol of NaH) was added. This mixture was stirred under N$_2$ until evolution of H$_2$ had ceased. Bromomethylcyclopropane (0.35 ml, 3.6 mmol) in DMF (0.5 ml) was added and the reaction was stirred at room temperature under N$_2$ overnight. The mixture was neutralized with acetic acid and evaporated to a semi-solid residue which was partitioned between EtOAc and 10% aqueous Na$_2$CO$_3$. The organic layer was dried (MgSO$_4$), filtered and evaporated to dryness. This residue was chromatographed on silica gel 60 (dry packed) developing with a step gradient of EtOAc:hexanes (1:4) to EtOAc:hexanes (2:3) to give 1.007 g (2.56 mmol, 85%) of the title compound as a white solid, mp 141°–143° C.

Calculated for $C_{18}H_{25}N_6O_2Cl \cdot 0.1H_2O$: C, 54.78; H, 6.44; N, 21.29. Found: C, 55.1; H, 6.48; N, 20.94.

EXAMPLE 86

6-[1-(4-BOC)piperazinyl]-9-cyclopropylmethyl-2-ethoxypurine

Sodium spheres (120 mg, 5.2 mmol) were added to abs. EtOH (5 ml) and after hydrogen evolution had ceased, 517 mg (1.3 mmol) of material from the foregoing Example 85 in EtOH (95 ml) was added. This solution was heated under reflux under N$_2$ for 28 hrs. The mixture was neutralized with acetic acid evaporated to a solid residue which was partitioned between EtOAc and 10% aqueous Na$_2$CO$_3$. The organic phase was dried (MgSO$_4$), filtered and evaporated to dryness to give 510 mg of a viscous oil. This was chromatographed on a dry packed silica gel 60 column (60 ml) which was developed with a step gradient of EtOAc:hexanes (1:4) to EtOAc:hexanes (2:3) in 10% increments. Fractions containing the required product were pooled and evaporated to dryness to give 389 mg (0.97 mmol, 74%) of the title compound as a white solid, mp 120°–122° C. Mass spec (EI) showed M$^+$ at 402 m/e.

Calculated for $C_{20}H_{30}N_6O_3$: C, 59.68; H, 7.51; N, 20.88. Found: C, 59.87; H, 7.65; N, 20.75.

EXAMPLE 87

9-Cyclopropylmethyl-2-ethoxy-6-(1-piperazinyl)purine dihydrochloride

The foregoing material prepared in Example 86 (260 mg, 0.65 mmol) was dissolved in abs. EtOH (6 ml) and ethanolic HCl (2 ml) was added. This solution was concentrated slowly under a stream of N$_2$. A white precipitate formed which was washed well with Et$_2$O. Yield 222 mg (0.59 mmol, 92%).

Mass spec (EI) showed M$^+$ (free base) at 302 m/e.

Calculated for $C_{15}H_{22}N_6O \cdot 2HCl$: C, 48.01; H, 6.45; N, 22.39. Found: C, 48.17; H, 6.52; N, 22.29.

EXAMPLE 88

6-[1-(4-BOC)piperazinyl]-2-chloro-9-(methoxyethyl)-purine

The material prepared in Example 50 (1.02 g, 3.0 mmol) was dissolved in sieve dried DMF (25 ml) and 60% NaH in oil (180 mg, 4.5 mmol of NaH) was added and the mixture was stirred under $N_2$. When a homogeneous solution was apparent 2-bromoethyl methyl ether (0.33 ml, 3.6 mmol) was added and the reaction was left stirring overnight. Additional 2-bromoethyl methyl ether (0.085 ml) was then added followed by sodium iodide (90 mg, 0.6 mmol). After stirring for an additional 24 hrs. the mixture was neutralized with acetic acid and evaporated to dryness in vacuo. The residue so obtained was partitioned between $CH_2Cl_2$ and 10% aqueous $Na_2CO_3$ and the organic phase was dried ($MgSO_4$), filtered and evaporated to dryness. Purification was carried out on a dry packed silica gel 60 column (70 ml) developing with a step gradient of (1:4) to (1:1) EtOAc:hexanes. Fractions containing the required product were pooled and evaporated to dryness to give (1.82 mmol, 61%) of the title compound as a tlc pure white solid. Mp 104°–107° C., mass spec (EI) showed M+ at 397 and 399 m/e.

Calculated for $C_{17}H_{25}N_6O_3Cl$: C, 51.45; H, 6.35; N, 21.18. Found: C, 51.63; H, 6.36; N, 21.03.

EXAMPLE 89

6-(1-(4-BOC)piperazinyl]-2-methoxy-9-(methoxyethyl)-purine

To a methanolic solution of sodium methoxide (0.75 ml of 4.37M solution) in methanol (8 ml) was added 325 mg (0.82 mmol) of the foregoing material prepared in Example 88. This solution was heated under reflux under $N_2$ for 4 days. After evaporation to dryness, the residue was partitioned between $CH_2Cl_2$ and 10% aqueous $Na_2CO_3$ and the organic layer was dried ($MgSO_4$), filtered and evaporated to dryness. Purification was carried out on a dry packed silica gel 60 column (40 ml) developing with a step gradient of (3:7) to (3:2) EtOAc:hexanes. Fractions containing the required product were pooled and evaporated to dryness to give 192 mg of the title compound as a clear, tlc pure oil.

EXAMPLE 90

2-Methoxy-9-methoxyethyl-6-(1-piperazinyl)purine dihydrochloride

The foregoing material prepared in Example 89 (182 mg, 0.46 mmol) was dissolved in abs. EtOH (3 ml) and ethanolic HCl (1.5 ml) was added. After 2 hrs. the solution was concentrated under a stream of $N_2$ to give a white solid which was washed with $Et_2O$ and EtOH to give 109 mg of the title compound. Mass spec (EI) showed M+ (free base) at 293 m/e.

Calculated for $C_{13}H_{20}N_6O_2 \cdot 2HCl$: C, 42.75; H, 6.07, N, 23.01. Found: C, 42.87, H, 6.09; N, 22.94.

EXAMPLE 91

6-[1-(4-BOC)piperazinyl]-2-chloro-9-(methylthiomethyl)purine

The material prepared in Example 50 (1.02 g, 3.0 mmol) was dissolved in sieve dried DMF (25 ml) under $N_2$ and 60% NaH in oil (156 mg, 3.9 mmol of NaH) was added. After the evolution of $H_2$ had ceased, chloromethyl methyl sulfide (0.3 ml, 3.6 mmol) in DMF (3 ml) was added and the reaction was stirred at room temperature for 3 days. Cold $H_2O$ (25 ml) was carefully added, followed by 10 ml of 10% aqueous $Na_2CO_3$. After stirring for 1 hr the mixture was evaporated to dryness in vacuo and the residual solid was partitioned between EtOAc and 10% aqueous $Na_2CO_3$. The organic phase was dried ($MgSO_4$), filtered and evaporated to dryness. The residue so obtained was purified by chromatography on a dry packed silica gel 60 column 960 ml) developed with a step gradient of (1:4 to 2:3) EtOAc:hexanes. Fractions containing the required product were pooled and evaporated to dryness to give 625 mg (1.72 mmol, 57%) of the title compound as a white solid. Mp 144°–145° C., mass spec (EI) showed M+ at 398 m/e.

EXAMPLE 92

6-([1-(4-BOC)piperazinyl]-2-methoxy-9-(methylthiomethyl)purine

To a methanolic solution of sodium methoxide (0.76 ml of a 4.37M solution) in methanol (8 ml) was added 301 mg (0.75 mmol) of the foregoing material prepared in Example 91. This solution was heated under reflux under $N_2$ for 2 days and then was cooled and neutralized with acetic acid before being evaporated to dryness. The solid so obtained was partitioned between EtOAc and 10% aqueous $Na_2CO_3$ and the organic phase was dried ($MgSO_4$) filtered and evaporated to dryness. Purification was carried out on a dry packed silica gel 60 column (40 ml) developed with a step gradient of EtOAc:hexanes (1:4 to 1:1). Fractions containing the required product were pooled and evaporated to dryness to give 264 mg (0.67 mmol, 89%) of the title compound. Mp 138°–139.5°, mass spec. (EI) showed M+ at 394 m/e.

Calculated for $C_{17}H_{26}N_6O_3S \cdot 0.1H_2O$: C, 51.52; H, 6.67; N, 21.21. Found: C, 51.91; H, 6.74; N, 20.88.

EXAMPLE 93

2-Methoxy-9-(methylthiomethyl)-6-(1-piperazinyl)purine maleate

The foregoing material prepared in Example 92 (253 mg, 0.64 mmol) was dissolved in $CF_3COOH$ (3 ml) and stirred at room temperature for 40 min. The mixture was concentrated under a stream of $N_2$ and a slurry of Dowex 1×2 (OH) in $H_2O$ was added to the residue. This mixture was poured onto a column (2.5×20 cm) of Dowex 1×2 (OH) and the column was developed with $H_2O$. Fractions containing the required product were pooled and evaporated to dryness to give 91 mg (0.31 mmol) of the title compound as its free base. This was dissolved in EtOH (3 ml) and maleic acid (69 mg, 0.60 mmol) in EtOH (4 ml) was added. The solution was concentrated under a stream of $N_2$ and the precipitate obtained was separated and washed with $Et_2O$. Yield 117.6 mg (0.29 mmol, 45%), mass spec. (EI) showed M+ (free base) at 294 m/e.

Calculated for $C_{12}H_{18}N_6SO \cdot 1.2 \, C_4H_4O_4$: C, 46.53; H, 5.30; N, 19.38. Found: C, 46.57; H, 5.44; N, 19.33.

EXAMPLE 94

6-[1-(4-BOC)piperazinyl]-2-chloro-9-[2-(trimethylsilyl)ethoxymethyl]purine

The material prepared in Example 50 (2.03 g, 6.0 mmol) was dissolved in sieve dried DMF (50 ml) and 60% NaH in oil (336 mg, 8.4 mmol of NaH) was added. This mixture was stirred under $N_2$ until hydrogen evolution had ceased and then 2-(trimethylsilyl)ethoxymethyl chloride (1.17 ml, 6.6 mmol) was added. The reaction was stirred under $N_2$ at room temperature for 24 hrs. and then cold $H_2O$ (50 ml) was added, followed by 10% aq. $Na_2CO_3$ (20 ml). This mixture was evaporated to dryness and the solid residue was partitioned between $CH_2Cl_2$ and 10% aq. $Na_2CO_3$. To the organic phase was added a little EtOAc (to effect complete dissolution) and then it was dried ($MgSO_4$), filtered and evaporated to dryness. Purification was carried out on a dry packed silica gel 60 column (3.5×25 cm), developed with a step gradient (1:9 to 2:3) of EtOAc:hexanes. Fractions containing the required product were pooled and evaporated to dryness to give 2.08 g (4.43 mmol, 74%) of a white gummy solid. A portion was recrystallized from EtOH to give an analytical sample. Mp 127°–128.5° C.

Calculated for $C_{20}H_{33}N_6O_3ClSi$: C, 51.21; H, 7.09; N, 17.92. Found: C, 51.30; H, 6.97; N, 17.95.

EXAMPLE 95

6-[1-(4-BOC)piperazinyl]-2-methoxy-9-[2-(trimethylsilyl)ethoxymethyl]purine

The foregoing material prepared in Example 94 (957 mg, 2.04 mmol) was added to a solution of 4.37M methanolic sodium methoxide (1.87 ml) in MeOH (20 ml) and the mixture was heated under reflux under $N_2$ for 3 days. The mixture was neutralized with acetic acid and then evaporated to dryness to give a solid residue which was partitioned between EtOAc and 10% aqueous $Na_2CO_3$. The organic phase was dried ($MgSO_4$), filtered and evaporated to dryness. This material was purified on a dry-packed silica gel 60 column (70 ml) developed with a step gradient of (1:4 to 2:3) of EtOAc:hexanes. Fractions containing the required product were pooled and evaporated to dryness to give 794 mg (1.71 mmol, 84%) of the title compound as a white solid. Mp 109°–110° C.

Calculated for $C_{21}H_{36}N_6O_4Si$: C, 54.29; H, 7.81; N, 18.09. Found: C, 54.24; H, 7.87; N, 18.12.

EXAMPLE 96

6-[1-(4-BOC)piperazinyl]-2-methoxypurine

The foregoing material prepared in Example 95 (782 mg, 1.68 mmol) was dissolved in dry THF (9 ml) and 9 ml of a 1M solution of tetrabutylammonium fluoride in THF was added. This solution was heated at 60° overnight and then an additional 2 ml of 1M tetrabutylammoniumfluoride in THF was added and the heating was continued at 70° for an additional 6 hrs. This mixture was evaporated to dryness and the orange residual oil was purified on a dry packed silica gel 60 column (80 ml) developed with a step gradient (1:4 to 2:3) of acetone:hexanes. Fractions containing the required product were pooled and evaporated to dryness to give 358 mg (1.07 mmol, 64%) of the title compound as a tlc pure white solid.

EXAMPLE 97

6-[1-(4-BOC)piperazinyl]-9-[1-(2-fluoroethyl)]-2-methoxypurine

Method A

The foregoing material prepared in Example 96 (102.8 mg, 0.31 mmol) was dissolved in sieve dried DMF (3 ml) and stirred under $N_2$. To this solution was added 60% NaH in oil (16 mg, 0.4 mmol of NaH) and when $H_2$ evolution had ceased, 1-bromo-2-fluoroethane (50 mg, 0.4 mmol) was added. After stirring overnight the mixture was neutralized with acetic acid and evaporated to dryness. This residue was partitioned between EtOAc and 10% aqueous $Na_2CO_3$ and the organic phase was dried ($MgSO_4$), filtered and evaporated to dryness. Purification was carried out on a dry-packed silica gel 60 column (30 ml) developed with a step gradient (3:7 to 3:2) of EtOAc:hexanes. Fractions containing the required product were pooled and evaporated to dryness to give 85.2 mg (0.23 mmol, 73%) of the title compound as a white solid. Mp 139.5°–104.5° C.

Calculated for $C_{17}H_{25}N_6OF \cdot 0.2H_2O$: C, 53.31; H, 6.68; N, 21.94. Found: C, 53.55; H, 6.56; N, 21.61.

Method B

A mixture of the material prepared in Example 117 (50 mg, 0.13 mmol) and methanol (0.5 ml) containing sodium methoxide (0.5 mmol) was refluxed under a nitrogen atmosphere for 18 hours. After cooling, the reaction treated with a mixture of 1M $K_2PO_4$ and $CHCl_3$, and after thorough mixing the phases were separated. The aqueous phase was reextracted with $CHCl_3$ and the organic phases dried ($MgSO_4$) and evaporated to give 60 mg of a crystalline residue. Preparative tlc on one 20×20 cm×1000μ silica gel GF plate with (1:1) EtOAc:hexanes gave, after isolation, 17.5 mg of unreacted starting material and, 23.3 mg the title compound which was identical to material prepared by Method A.

EXAMPLE 98

9-[1-(2-Fluoroethyl)]-2-methoxy-6-(1-piperazinyl)purine dihydrochloride

The foregoing material prepared in Example 97 (78 mg, 0.26 mmol) was dissolved in abs. EtOH (4 ml) and 2 ml of ethanolic HCl was added. After standing at room temperature for 30 min the solution was slowly concentrated using a stream of $N_2$. The white solid so obtained was washed with EtOH and $Et_2O$ and dried to give 58.9 mg (0.16 mmol, 62%) of the title compound.

Calculated for $C_{12}H_{17}N_6OF \cdot 2HCl \cdot 0.2\ CH_3CH_2OH$: C, 41.09; H, 5.67; N, 23.19. Found: C, 40.86; H, 5.68; N, 22.85.

The 0.2 molar equivalents of EtOH in the analytical sample were verified by NMR.

EXAMPLE 99

6-[1-(4-BOC)piperazinyl]-2-methoxy-9-[1-(2-propynyl)]purine

The material prepared in Example 96 (150 mg, 0.45 mmol) was dissolved in sieve dried DMF (3 ml) and 60% NaH in oil (27 mg, 0.67 mmol of NaH) was added. This mixture was stirred under $N_2$ until hydrogen evolution had ceased and then propargyl bromide (80% by wt in toluene; 0.06 ml, 0.54 mmol) was added. The mixture was stirred at room temperature overnight under $N_2$ and then was neutralized with acetic acid before being evaporated to dryness. This solid residue was partitioned between $CH_2Cl_2$ and 10% aq. $Na_2CO_3$ and the organic phase was dried ($MgSO_4$), filtered and evaporated to dryness. Two products were apparent by tlc and these were separated on a dry packed silica gel 60 column (50 ml) developed with a step gradient of hexanes to acetone:hexanes (1:4). Fractions containing the slower moving material were pooled and evaporated to dryness to give 48 mg (0.13 mmol, 29%) of the title compound as a clear oil. Mass spec (EI) showed

EXAMPLE 100

9-(1-Allenyl)-6-[1-(4-BOC)piperazinyl]-2-methoxypurine

Fractions containing the faster moving product from the silica gel 60 column described in the previous Example 99 were pooled and evaporated to dryness to give 66 mg (0.18 mmol, 39%) of the title compound as a white solid. Mass spec. (EI) showed M++H at 373 m/e. Further identification was by PMR (see Table).

EXAMPLE 101

2-Methoxy-6-(1-piperazinyl)-9-[1-(2-propynyl)]purine dihydrochloride

The material prepared in Example 99 (40 mg, 0.11 mmol) was deblocked in the usual way with ethanolic HCl to give 24 mg (0.07 mmol, 617.) of the title compound. Mass spec. (EI) showed M+ (free base) at 272 m/e.

Calculated for $C_{13}H_{16}N_6O.2HCl.1.1\ H_2O$: C, 42.77; H, 5.58; N, 23.02. Found: C, 42.94; H, 5.11; N, 22.65.

EXAMPLE 102

9-(1-Allenyl)-2-methoxy-6-(1-piperazinyl)purine dihydrochloride

The material prepared in Example 100 (63 mg, 0.17 mmol) was deblocked in the usual way with ethanolic HCl to give 60.2 mg (0.16 mmol, 97%) of the title compound. Mass spec. (EI) showed M++H (free base) at 273 m/e.

Calculated for $C_{13}H_{16}N_6O.2HCl.0.6\ H_2O.0.25\ CH_3CH_2OH$: C, 44.12; H, 5.68; N, 22.87. Found: C, 44.03; H, 5.55; N, 22.85.

The 0.25 molar equivalents of EtOH in the analytical sample were verified by NMR.

EXAMPLE 103

6-[1-(4-BOC)piperazinyl]-2-methoxy-9-[1-(2-propenyl)-]purine

The material prepared in Example 96 (150 mg, 0.45 mmol) was dissolved in sieve dried DMF (8 ml) and 60% NaH in oil (27 mg, 0.68 mmol of NaH) was added. This mixture was stirred under $N_2$ until evolution of hydrogen had ceased and then 3-iodopropene (0.05 ml, 0.55 mmol) was added. After stirring for 6 hrs. under $N_2$ at room temperature, the mixture was evaporated to dryness in vacuo and the residue was partitioned between $CH_2Cl_2$ (100 ml) and 10% aq. $Na_2CO_2$ (20 ml). The organic phase was dried ($MgSO_4$), filtered and evaporated to dryness. This residue was purified on a silica gel 60 column (15 g) developed with a step gradient of hexanes, EtOAc:hexanes (1:3), EtOAc:hexanes (1:1) and then EtOAc. Fractions containing the required product were pooled and evaporated to dryness to give 138 mg (0.37 mmol, 82%) of the title compound as a tlc pure syrup. Mass spec. (EI) showed M++H at 375 m/e.

EXAMPLE 104

2-Methoxy-6-(1-piperazinyl)-9-[1-(2-propenyl)]purine dihydrochloride

The foregoing material prepared in Example 103 (133 mg, 0.36 mmol) was deblocked with ethanolic HCl in the usual way to give 101 mg (0.29 mmol, 81%) of the title compound.

Calculated for $C_{13}H_{18}N_6O.2HCl$: C, 44.96; H, 5.81; N, 24.2. Found: C, 45.22; H, 6.19; N, 24.

EXAMPLE 105

5-Amino-4-chloro-6-cyclopropylamino-2-ethylpyrimidine

A mixture of 4,6-dichloro-5-nitro-2-ethylpyrimidine (0.5 g), Raney nickel (ca. 0.5 g) and MeOH (5 ml) was shaken in a hydrogen atmosphere at 1-2 p.s.i until reduction of the nitro group was complete. The mixture was filtered, evaporated to a black gum, taken up in a mixture of cyclopropylamine (5 ml, ca. 100 mmol) and isopropyl alcohol (5 ml) and heated in a bomb at 110° for 4 hours. The reaction mixture was then filtered, evaporated to dryness under reduced pressure and the pure product was isolated by preparative tlc using four $20\times20\ cm\times1000\mu$ silica gel GF plates developed with 1:1 EtOAc:hexanes; 315 mg of product was obtained. Yield: 64%. NMR ($CDCl_3$, δ from TMS): 0.47(m) and 0.76(m) cyclopropyl methylenes, 1.24 (t, $CH_3$), 2.69 (q, $\underline{CH_2}CH_3$), 2.86 (m, CH), 3.47 (br s, $NH_2$), 5.47 (br s, $\overline{NH}$).

EXAMPLE 106

6-Chloro-9-cyclopropyl-2-ethylpurine

A mixture of the material prepared in the foregoing Example 105 (315 mg, 1.47 mmol), triethylorthoformate (3 ml), and conc. HCl (0.03 ml) was heated and stirred at 60°. After two hours the mixture was evaporated under a stream of nitrogen with heating. The solid brown residue was purified by preparative tlc on four $20\times20\ cm\times1000\mu$ silica gel GF plates developed with 10% MeOH in $CH_2Cl_2$.

The main band was isolated and extracted to give 265 mg of the title compound as a crystalline solid. NMR ($CDCl_3$, δ from TMS): 1.12-1.30 (m, cyclopropyl methylenes), 1.41 (t, $CH_3$), 3.07 (q, $\underline{CH_2}CH_3$), 3.50 (m, CH), 8.03 (s, H8).

EXAMPLE 107

6-[1-(4-BOC)piperazinyl]-9-cyclopropyl-2-ethylpurine

A mixture of the foregoing material prepared in Example 106 (249 mg, 1.2 mmol) 1-BOC piperazine (232 mg, 1.3 mmol) and triethylamine (0.35 ml, 2.5 mmol) in i-amyl alcohol (5 ml) were refluxed for 3 hours. The mixture was taken to dryness under reduced pressure and purified on four $20\times20\ cm\times1000\mu$ silica gel GF plates using 1:1 EtOAc:hexane. Isolation and extraction of the main band gave the title compound.

EXAMPLE 108

9-Cyclopropyl-2-ethyl-6-(1-piperazinyl)purine

A portion of the foregoing material prepared in Example 107 was dissolved in ca. 1 ml of $CF_3CO_2H$. After 15-20 minutes, the clear solution was evaporated to a gum under a nitrogen stream, and the residue was partitioned between water and chloroform. The aqueous phase was extracted a second time with chloroform and then made basic by careful addition of solid $K_2CO_3$. The milky aqueous solution was extracted repeatedly with chloroform and the combined organic extracts were dried ($MgSO_4$) and evaporated to dryness to give the title compound, which was crystallized from ether.

Calculated for C$_{14}$H$_{20}$N$_6$.0.1 (C$_2$H$_5$)$_2$O: C, 61.82; H, 7.57; N, 30.04. Found: C, 61.45; H, 7.65; N, 29.85.

EXAMPLE 109

4-[1-(4-BOC)piperazinyl]-6-chloro-2-ethyl-5-nitropyrimidine

To a stirred solution of 4,6-dichloro-5-nitro-2-ethylpyrimidine (509 mg, 2.3 mmol) and triethylamine (0.35 ml, 2.5 mmol) in sieve dried DMF (4 ml) was added dropwise over 3 minutes a solution of BOC-piperazine (0.5 g, 2.7 mmol) in sieve dried DMF (2 ml). The mildly exothermic reaction was allowed to proceed for a few minutes longer after which time it was filtered and the filtrate evaporated to a gum under high vacuum. The residue was partitioned between CHCl$_3$ and water, the aqueous phase extracted again with CHCl$_3$, the combined organic extracts washed once with water, once with saturated NaCl solution, dried (MgSO$_4$) and evaporated to a dark foam. This residue was purified by preparative tlc on four 20×20 cm×1000μ silica gel of plates with 20% ethyl acetate in hexane. The main (high Rf) band of the four observed afforded 466 mg of the title compound as a yellow solid which was crystallized from hexane. NMR (CDCl$_3$, δ from TMS): 1.29 (t, CH$_3$), 1.47 (s, C(CH$_3$)$_3$), 2.80 (q, C$\underline{H_2}$CH$_3$), 3.58 (m, piperazine methylenes).

EXAMPLE 110

4-[1-(4-BOC)piperazinyl]-2-ethyl-5-nitro-6-[1-(2,2,2-trifluoroethylamino)]pyrimidine

To a solution of the foregoing material prepared in Example 109 (418 mg, 1.3 mmol) and triethylamine (0.2 ml, 1.4 mmol) in sieve dried DMF (5 ml) was added dropwise, with stirring, a solution of 209 mg (2.1 mmol) of 2,2,2-trifluoroethylamine in sieve dried DMF (1 ml) over two minutes. No exotherm was noted. After standing 64 hours, the reaction mixture was evaporated to dryness under reduced pressure and the residue was partitioned between water and CHCl$_3$. The aqueous phase was extracted again with CHCl$_3$, and the combined organic phases were washed once with water, once with saturated NaCl solution, dried (MgSO$_4$) and evaporated to a gum. This was purified on four 20×20 cm×1000μ silica gel GF plates using EtOAc:hexanes 1:4). Isolation and extraction of the main band gave 414 mg of the title compound suitable for further reactions. NMR (CDCl$_3$, δ from TMS): 1.24 (t, C$\underline{H_2}$CH$_3$), 1.49 (s, C(CH$_3$)$_3$), 2.65 (q, C$\underline{H_2}$CH$_3$), 3.56 (br s, piperazine methylenes), 4.36 (m, C$\underline{H_2}$CF$_3$), 8.43 (t, NH̲CH$_2$).

EXAMPLE 111

5-Amino-4-[1-(4-BOC)piperazinyl]-2-ethyl-6-[1-(2,2,2-trifluoroethylamino)]pyrimidine

A suspension of the foregoing material prepared in Example 110 (363 mg, 0.96 mmol) in MeOH (10 ml) containing 0.2–0.3 g Raney nickel, was shaken in a 1-2 p.s.i. atmosphere of hydrogen. After 24 hrs. the mixture was filtered (the organic material having now dissolved), evaporated and purified by preparative tlc on four 20×20 cm×1000μ silica gel GF plates using EtOAc:hexanes (1:4), to give ca. 0.2 g of the title compound along with some recovered unreduced starting material. NMR (CDCl$_3$, δ from TMS): 1.25 (t, CH$_2$C$\underline{H_3}$), 1.48 (s, C(CH$_3$)$_3$), 2.68 (q, C$\underline{H_2}$CH$_3$), 2.97 (br s NH̲$_2$), 3.14 (m) and 3.58 (m) (piperazine methylenes), 4.25 (m, CH$_2$CF$_3$), 4.53 (t, NH̲CH$_2$).

EXAMPLE 112

6-[1-(4-BOC)piperazinyl]-2-ethyl-9-[1-(2,2,2-trifluoroethylamino)]purine

To a solution of the foregoing material prepared in Example 111 (79 mg) in triethyl orthoformate (1.0 ml) stirred at 60° C. was added concentrated HCl (0.01 ml). After 6 hrs, heating was stopped and the reaction was left standing at ambient temperature for ca. 12 hours. The solution was shaken with 1M K$_2$HPO$_4$ (1 ml), the organic phase was removed, dried (MgSO$_4$) and evaporated to a solid. The residue was purified by preparative tlc using two 20×20 cm×1000μ silica gel GF plates, developed with MeOH:CH$_2$Cl$_2$ (5:95). Isolation and extraction of the main band gave pure title compound. Further purification was effected by crystallization from hexanes.

EXAMPLE 113

2-ethyl-9-[1-(2,2,2-trifluoroethylamino)]-6-(1-piperazinyl)purine

The foregoing material prepared in Example 112 (160 mg) was dissolved in ca. 2 ml of trifluoroacetic acid. After 30 minutes the solution was evaporated to a gum under a nitrogen stream and the residue was partitioned between water and CHCl$_3$. The aqueous phase was separated, extracted a second time with CHCl$_3$, then made basic by careful addition of solid K$_2$CO$_3$, and saturated with solid NaCl. The milky solution was extracted several times with CHCl$_3$ and the combined organic phases were washed once with saturated NaCl solution, dried (MgSO$_4$) and evaporated to give 124 mg of a gum. Recrystallization from hexanes, after removal of a slight flocculant insoluble contaminant, gave 91 mg of the title compound. Mp 104°–106° C.

Calculated for C$_{13}$H$_{17}$N$_6$F$_3$: C, 49.67; H, 5.45; N, 26.74. Found: C, 49.87; H, 5.56; N, 26.69.

EXAMPLE 114

6-[1-(4-BOC)piperazinyl]-2-chloro-9-[1-(2-oxopropyl)-]purine

The material prepared in Example 50 (1.02 g, 3.0 mmol) was dissolved in sieved-dried DMF 925 ml) and 60% NaH in oil (156 mg, 3.9 mmol of NaH) was added and the mixture was stirred under N$_2$ until evolution of H$_2$ had ceased. Chloroacetone (0.31 ml, 3.9 mmol) was then added and the mixture was stirred under N$_2$ for 3 days. The reaction was evaporated to dryness and the residue was partitioned between EtOAc and 10% aq. Na$_2$CO$_3$. The organic phase was dried (MgSO$_4$), filtered and evaporated to dryness to give 1.28 g of a pale yellow oil. Trituration under hexanes gave 1.07 g of the title compound, mp 173°–175° C.

Calculated for C$_{17}$H$_{23}$N$_6$OCl: C, 51.71; H, 5.87; N, 21.28. Found: C, 51.58; H, 5.87; N, 20.95.

EXAMPLE 115

6-[1-(4-BOC)piperazinyl]-2-chloro-9-[1-(2,2-difluoropropyl)]purine

A suspension of MgO (50 mg) in sieve dried CH$_2$Cl$_2$ (1.1 ml) containing diethylaminosulfur trifluoride (0.1 ml, 0.8 mmol) was stirred while 315 mg (0.8 mmol) of the material prepared in Example 114 was added under nitrogen over 2–3 minutes. After 20 hours an additional 0.1 ml of diethylamino sulfurtrifluoride was added, and after four more hours the reaction was worked up. The mixture was added to 1M $K_2HPO_4$ and the mix was extracted with several portions of $CHCl_3$. The pooled organic layers were dried ($MgSO_4$), filtered and evaporated to give a semicrystalline product. Preparative tlc on four 20×20 cm×1000μ silica gel GF plates developed with EtOAc:hexanes (1:1) gave 60 mg of recovered starting ketone and 184 mg of the title compound.

EXAMPLE 116

6-[1-(4-BOC)piperazinyl]-9-[1-(2,2-difluoropropyl)]-2-methoxypurine

A mixture of the foregoing material prepared in Example 115 (50 mg, 0.12 mmol) and methanol (0.2 ml) containing ca. 0.4 mmol of sodium methoxide was refluxed under a nitrogen atmosphere for 18 hours. After cooling it was treated with a mixture of 1M $KH_2PO_4$ and $CHCl_3$ and after thorough mixing, the phases were separated. The aqueous phase was extracted again with $CHCl_3$ and the combined organic extracts dried ($MgSO_4$) and evaporated to give 44 mg of a semicrystalline residue. Preparative tlc on one 20×20 cm×1000μ silica gel GF plate developed with EtOAc:hexanes (1:1) gave 6.4 mg of starting material and 29.1 mg of the title compound as a gum which crystallized upon trituration under ether.

EXAMPLE 117

6-[1-(4-BOC)piperazinyl]-2-chloro-9-[1-(2-fluoroethyl)-]purine

The material prepared in Example 50 (300 mg, 0.89 mmol) was dissolved in sieve dried DMF (5 ml) and 60% NaH in oil (1.5 mmol of NaH) was added. This mixture was stirred under $N_2$ until evolution of $H_2$ had ceased (2½ hr). The mixture was centrifuged and the supernatant was added dropwise to a stirred solution of 1-bromo-2-fluoroethane (7.9 mmol) in 1 ml of sieve dried DMF. After stirring overnight at room temperature under $N_2$, the residue was partitioned between $CH_2Cl_2$ and sat. aq. $NaHCO_3$. The aqu. layer was further washed with $CH_2Cl_2$ and the pooled organic layers were dried ($MgSO_4$), filtered and evaporated to dryness. Purification was effected on four 20×20 cm×1000μ silica gel GF preparative plates developed with EtOAc:hexanes (1:1). The title compound was obtained as a crystalline solid after standing under $Et_2O$.

EXAMPLE 118

6-Chloro-2-ethyl-9-methylpurine

This was prepared in a manner similar to that described in Example 27 for 6-chloro-2,9-dimethylpurine, except that 5-amino-4-chloro-2-ethyl-6-methylaminopyrimidine was used as the starting material, and the final product was purified by chromatography. The title compound was obtained in 65% yield. NMR ($CDCl_3$, δ from TMS): 1.4 (t, $CH_2\underline{CH_3}$), 3.06 (q, $\underline{CH_2}CH_3$), 3.88 (s, $NCH_3$), 8.00 (s, $H_8$).

EXAMPLE 119

6-[1-(4-BOC)piperazinyl]-2-ethyl-9-methylpurine

This was prepared in a manner similar to that described in Example 28 for 6-[1-(4-BOC)piperazinyl]-2,9-dimethylpurine, except that the foregoing material prepared in Example 118 (332 mg, 1.68 mmol) was used as the starting material. The title compound was obtained in good yield after purification on four 20×20 cm×1000μ silica GF plates developed with $CHCl_3$:MeOH:$NH_4OH$ (90:10:1)

EXAMPLE 120

2-Ethyl-9-methyl-6-(1-piperazinyl)purine dihydrochloride

The foregoing material prepared in Example 119 (300 mg, 0.87 mmol) was deblocked in the usual fashion using ethanolic HCl to give the title compound (197 mg, 0.62 mmol, 71%) as a white crystalline solid.

Calculated for $C_{12}H_{18}N_6\cdot 2HCl$: C, 45.15; H, 6.32; N, 26.33; Cl, 22.21. Found: C, 45.20; H, 6.24; N, 26.53; Cl, 22.41.

EXAMPLE 121

6-[1-(4-BOC)piperazinyl]-2-chloro-9-(2-propyl)purine

This was prepared in a manner similar to that described in Example 74 for 6-[1-(4-BOC)piperazinyl]-2-chloro-9-(1-propyl)purine, except that 2-iodopropane was used as the alkylating agent. The reaction utilized 678 mg (2.0 mmol) of 6-[1-(4-BOC)piperazinyl]-2-chloropurine as starting material and gave the title compound (640 mg, 1.68 mmol) in 84% yield after silica gel chromatography. Mass spec. (EI) showed $M^+$ at 380 and 382 m/e.

Calculated for $C_{17}H_{25}N_6O_2Cl$: C, 53.61; H, 6.62; N, 22.06. Found: C, 53.61; H, 6.59; N, 22.06.

EXAMPLE 122

6-[1-(4-BOC)piperazinyl]-2-methoxy-9-(2-propyl)purine

This was prepared in a manner similar to that described in Example 75 for 6-[1-(4-BOC)piperazinyl]-2-methoxy-9-(1-propyl)purine, except that the foregoing material described in Example 121 (305 mg, 0.8 mmol) was used as the starting material. The title compound was obtained as a crystalline solid (200 mg, 0.53 mmol, 66%) without recourse to chromatographic purification. Mass spec. (EI) showed $M^+$ at 376 m/e.

Calculated for $C_{18}H_{28}N_6O_3$: C, 57.43; H, 7.50; N, 22.33. Found: C, 57.30; H, 7.46; N, 22.32.

EXAMPLE 123

2-Methoxy-6-(1-piperazinyl)-9-(2-propyl)purine dihydrochloride

The foregoing material prepared in Example 122 (150 mg, 0.40 mmol) was deblocked in the usual fashion using ethanolic HCl to give the title compound (89.4 mg, 0.26 mmol; 64%) as a white solid. Mass spec. (EI) showed $M^+$ (free base) at 276 m/e.

Calculated for $C_{13}H_{20}N_6O\cdot 2HCl\cdot 0.2H_2O$: C, 44.25; H, 6.40; N, 23.82. Found: C, 44.24; H, 6.30; N, 23.59.

EXAMPLE 124

6-[1-(4-BOC)piperazinyl]-2-methoxy-9-[1-(2-oxopropyl)]purine

The material prepared in Example 96 (84 mg, 0.25 mmol) was dissolved in sieve dried DMF (2 ml) and 60% NaH in oil (15 mg, 0.38 mmol of NaH) was added. This mixture was stirred under $N_2$ under evolution of $H_2$ had ceased. Chloroacetone (0.03 ml, 0.38 mmol) was then added and the stirring was evaporated to dryness and the residue was partitioned between EtOAc and 10% aq. $Na_2CO_3$. The organic phase was dried ($MgSO_4$), filtered and evaporated to an oil. This was purified on a dry packed silica gel 60 column (25 ml)

developed with a step gradient (3:7 to 7:3) of EtOAc:-hexanes to give 80 mg (0.2 mmol, 80%) of the title compound as a chromatographically pure oil which crystallized upon trituration.

EXAMPLE 125

2-Methoxy-9-[1-(2-oxopropyl)]-6-(1-piperazinyl)purine dihydrochloride

The foregoing material prepared in Example 124 (65 mg, 0.17 mmol) was deblocked using ethanolic HCl in the usual fashion to give the title compound (25.7 mg, 0.07 mmol, 43%) as a white solid. Mass spec. (EI) showed M+ (free base) at 290 m/e.

Calculated for $C_{13}H_{18}N_6O.2HCl.H_2O$: C, 40.96; H, 5.82; N, 22.04. Found: C, 40.76; H, 5.69; N, 22.04.

EXAMPLE 126

9-[1-(2,2-Difluoropropyl)]-2-methoxy-6-(1-piperazinyl)-purine dihydrochloride

The material prepared in Example 116 (96 mg, 0.23 mmol) was deblocked in the usual fashion using ethanolic HCl (6.5 ml) to give the title compound (59.8 mg, 0.15 mmol, 65%) as a white crystalline solid.

Calculated for $C_{13}H_{18}N_6OF_2.0.7H_2O2HCl$: C, 39.24; H, 5.42; N, 21.13; Cl, 17.82. Found: C, 39.03; H, 5.34; N, 21.34; Cl, 17.92.

EXAMPLE 127

5-Amino-4,6-dichloro-2-ethylpyrimidine 4,6-Dichloro-5-nitro-2-ethylpyrimidine (185 g, 0.83 mol) was dissolved in methanol (1.5 L) and reduced under 15 p.s.i. $H_2$ in the presence of Raney nickel (30 g) for 5 hr. The mixture was filtered through Celite (washing well with MeOH) and the filtrate was evaporated to dryness to give 159.1 g (0.83 mol, quantitative yield) of the title compound as a chromatographically pure (silica gel plates, developed with EtOAc:hexanes, 3:1) dark liquid which was used directly in the next step.

EXAMPLE 128

6-Chloro-5,6-diamino-2-ethylpyrimidine

The material prepared in the foregoing Example 127 (6.19 g, 32 mmol) was dissolved in 2-propanol (75 ml) and 10 ml of anhydrous ammonia was added. This was sealed in a pressure vessel and heated at 110° for 4 hr. The mixture was vented and then evaporated to a solid residue under a stream of nitrogen. This residue was leached with $CH_2Cl_2$ (3×10 ml) and the soluble material (3 g) was shown (tlc, EtOAc:hexanes, 1:1) to be predominantly unreacted starting material, whereas the insoluble material (3.29 g, 19 mmol) was chromatographically pure title compound, suitable for the next reaction (Yield, 60%; quantitative, based on recovered starting material).

EXAMPLE 129

6-Chloro-2-ethylpurine

The material prepared in the foregoing Example 128 (1.50 g, 8.72 mmol) and triethylorthoformate (15 ml) were mixed and heated at 60° for 1 hr. Concentrated HCl (0.15 ml) was added and the heating was continued overnight. After cooling to room temperature the suspension was filtered off and the solid was washed with $Et_2O$. This solid product (1.1 g) was essentially chromatographically pure (silica gel; $CHCl_3$:MeOH:N-$H_4OH$-90:10:1). An analytical sample was prepared by recrystallization from MeOH. NMR (DMSO-d6, δ from TMS): 1.31 (t, $CH_2\underline{CH_3}$), 3.95 (q, $\underline{CH_2}CH_3$), 8.57 (s, H8).

Calculated for $C_7H_7N_4Cl$: C, 46.04; H, 3.86; N, 30.68; Cl, 19.41. Found: C, 45.45; H, 3.98; N, 30.38; Cl, 19.91.

EXAMPLE 130

6-[1-(4-BOC)piperazinyl]-2-ethylpurine

The material prepared in the foregoing Example 129 (1.75 g, 9.6 mmol), BOC-piperazine (1.97 g, 11 mmol), triethylamine (2.8 ml, 20 mmol) and i-amyl alcohol (20 ml) were mixed and heated under reflux under $N_2$ for 3 hr. The mixture was allowed to cool and the solid was filtered off and washed with a small portion of i-amyl alcohol and then with $Et_2O$. Yield 2.1 g, 66%.

EXAMPLE 131

6-[1-(4-BOC)piperazinyl]-2-ethyl-9-(2-fluoroethyl)purine

The material prepared in the foregoing Example 130 (401 mg, 1.21 mmol) was dissolved in sieve dried DMF (5 ml) and 60% NaH in oil, 73 mg, 1.8 mmol of NaH) was added. This mixture was stirred under $N_2$ until the hydrogen evolution had ceased. The mixture was centrifuged and the supernatant was added dropwise, with stirring, to a solution of 1-bromo-2-fluoroethane (1.002 g, 7.89 mmol) in sieve dried DMF (1 ml). This mixture was stirred under $N_2$ overnight and then was evaporated to dryness in vacuo. The residue was partitioned between 1M $KH_2PO_4$ and $CH_2Cl_2$, and the aqueous phase was washed once more with $CH_2Cl_2$. The pooled organic layers were washed with $H_2O$ and sat. aq. NaCl, and then dried ($MgSO_4$), filtered, and evaporated to dryness (531 mg). This was purified on four 20×20 cm×1000μ silica gel GF plates developed with EtOAc:hexanes (1:2) to give 445 mg (1.18 mmol, 97%) of the title compound.

EXAMPLE 132

2-Ethyl-9-(2-fluoroethyl)-6-(1-piperazinyl)purine dihydrochloride

The material prepared in the foregoing Example 131 (339 mg, 0.90 mmol) was deblocked in the usual fashion using ethanolic HCl (2.0 ml) to give the title compound (149 mg, 0.4 mmol, 44%) as a white crystalline solid.

Calculated for $C_{13}H_{19}N_6.2HCl$: C, 41.27; H, 6.27; N, 22.21; Cl, 20.15. Found: C, 41.02; H, 6.37; N, 22.35; Cl, 20.02.

EXAMPLE 133

2-Methoxy-6-(1-piperazinyl)-9-(2-furanylmethyl)-9H-purine

To 2-methoxy-6-[1-(4-tertbutoxycarbonyl)-piperazinyl]-9H-purine (1.05 g., 3.1 mMol) in DMF (10 ml., sieve dried) at 0° C. under $N_2$ was added sodium hydride (60% dispersion) (0.25 g., 6.3 mMol). The mixture was washed to RT, and after stirring at 25° for 2 hours, the solution was centrifuged. The brown solution was then added dropwise over 5 minutes to a solution of 2-chloromethylfuran (W. R. Kirner, J. Am. Chem. Soc., 50, 1958 (1928)) (0.44 g., 3.8 mMol) in DMF (1 ml) at 0° C. After allowing to warm to RT overnight, the DMF was removed in vacuo over a 60° bath. The mixture was acidified with a saturated solution of $KH_2PO_4$ (25 ml), and the mixture was extracted with chloroform (3×25 ml). The combined extracts were dried over $MgSO_4$ and the solvent was removed in vacuo to leave a light tan oil (2.0 g); nmr (CDCl$_3$) δ: 1.43(9H, S), 3.52(4H, m), 3.95(3H, s), 4.22 (4H, m), 5.23(2H, s), 6.32(1H, m), 6.37(1H, d), 7.37(1H, d), 7.61(1H, s), contained 1.0 eq. of DMF; mass spectrum (FAB): 415.

The crude oil (2.0 g) was dissolved in a mixture 1N-HCl (12 ml) and acetonitrile (12 ml). After 2 hours at RT the solvent was partially removed in vacuo and dried under a stream of N$_2$. The residue was dissolved in H$_2$O (50 ml), decolorized with Darco and made basic to pH 12 with 10% NaOH. The product was extracted with CHCl$_3$ (3×25 ml), dried over Na$_2$SO$_4$ and concentrated to a light oil (0.8 g) of 2-methoxy-6-(1-piperazinyl)-9-(2-furanylmethyl)-9H-purine; nmr (CDCl$_3$) δ: 2.94(4H, m), 3.94(3H, s), 4.22(4H, bd. m), 5.23(2H, s), 6.31(1H, m), 6.36(1H, d), 7.35(1H, d), 7.59(1H, s); mass spectrum (FAB): 3.15.

Anal. Calcd. for C$_{15}$H$_{18}$N$_6$O$_2$.0.56 H$_2$O: C, 55.54; H, 5.94; N, 25.91. Found: C, 55.56; H, 5.95; N, 25.82.

A portion of oil was dissolved in three fold excess of 4N ethanolic HCl. The solution was concentrated in vacuo to remove excess HCl and the product was triturated with Et$_2$O-EtOH to yield a crystalline salt; mp. 174° dec.; nmr (D$_2$O) δ: 3.52(4H, m), 4.10(3H, s), 4.53(4H, m), 5.44(2H, s), 6.54(1H, m), 6.63(1H, d), 7.59(1H, s), 8.18(1H, d).

Anal. Calcd. for C$_{15}$H$_{18}$N$_6$O$_2$.2HCl. 1.5 H$_2$O: C, 43.49, H, 5.60; N, 20.28. Found: C, 43.70; H, 5.62; N, 20.37.

EXAMPLE 134

4,6-Dihydroxy-2-methoxypyrimidine

A solution of O-methyl isourea hydrogen sulfate (309.9 g, 1.8 mol) in anhydrous MeOH (1.5 L) was stirred and cooled to −5° to −10° C. and 1.24 L of a solution of 25% NaOMe in MeOH (291.7 g NaOMe, 5.4 mol) was added slowly over the course of 1.5 hr, while maintaining the temperature between 0° and −10° C. Diethyl malonate (273.3 mL, 288.3 g, 1.8 mol) was then added over 15 min and the mixture was stirred under nitrogen at 0° C. for 3 hr, and then was allowed to rise to room temperature and stirring was continued for 3 days. The pH of the mixture was adjusted to 4-5 using conc. HCl (a cooling bath was used to prevent elevation of temperature) and the finely divided precipitate was filtered slowly to give 575 g of solid. This was triturated under H$_2$O (1 L) and the solid was filtered off overnight and dried in vacuo over P$_2$O$_5$ to give 273 g of the title compound (1.5 mol, by UV estimate) contaminated with salt; nmr (d$_6$-DMSO/D$_2$O) d: 3.80 (s); mass spectrum shows m/e 142 (M+) This material was suitable for the next step.

EXAMPLE 135

4,6-Dihydroxy-2-methoxy-5-nitropyrimidine

To glacial HOAc (860 mL) was added red fuming HNO$_3$ (300 mL) with cooling and stirring, at such a rate that the temperature was kept below 20° C. This stirred mixture was cooled in an ice bath and the foregoing material prepared in Example 134 (200 g, 78% pure, 1.1 mol) was added in portions over a period of 1 hr such that the temperature was maintained between 18°-20° C. The reaction was then stirred overnight. The precipitate which formed was filtered off and washed with HOAc (50 mL). This solid was then slurried with ice-H$_2$O (400 mL), filtered off and dried to constant weight in vacuo at 60° C. to yield 141 g (0.75 mol, 68% yield) of the title compound; nmr (d$_6$-DMSO) d: 3.95 (s); mass spectrum showed m/e 187 (M+). A separate synthesis gave an analytical sample.

Anal. Calcd. for C$_5$H$_5$N$_3$O$_5$.1.17H$_2$O: C, 28.84; H, 3.55; N, 20.19. Found: C, 28.85; H, 3.26; N, 20.19.

EXAMPLE 136

4,6-Dichloro-2-methoxy-5-nitropyrimidine

To POCl$_3$ (80 mL) in a three-necked flask equipped with a mechanical stirrer, dropping funnel and thermometer, was added the foregoing material prepared in Example 135 (18.7 g, 100 mmol) in portions. To this mixture was added dropwise a solution of N,N-diethylaniline (20 mL) in POCl$_3$ (50 mL) over a period of 40 min, during which time the temperature was 35°-45° C. The suspension was then heated to 105° C. internal temperature to give a dark brown homogeneous solution. The reaction was heated under reflux for 2 hr and then was cooled and concentrated to a smaller volume in vacuo. This material was poured slowly into ice-H$_2$O and the mixture was extracted 3× with Et$_2$O. The combined ether layers were dried over MgSO$_4$, filtered through charcoal and evaporated to dryness to give 12.64 g (56.4 mmol, 56% yield) of the title compound as a chromatographically pure yellow colored solid (m.p. 50°-60° C.) which was suitable for the next step; nmr (CDCl$_3$) d: 4.14 (s).

EXAMPLE 137

6-[1-(4-BOC)piperazinyl]-4-chloro-2-methoxy-5-nitropyrimidine

A solution of the foregoing material prepared in Example 136 (49.35 g, 0.22 mol) in CH$_2$Cl$_2$ (495 mL) was cooled in an ice-H$_2$O bath and was well stirred while a solution of BOC-piperazine (42.29 g, 0.23 mol) and Et$_3$N (24.70 g, 0.24 mol) in CH$_2$Cl$_2$ (466 mL) was added dropwise over a period of 2 hr. The reaction mixture was then extracted with 10% aqueous Na$_2$CO$_3$ and the organic layer was dried over MgSO$_4$, filtered and evaporated to dryness to give a pale yellow solid which was dried in vacuo to give 87.47 g (quantitative yield) of the title compound. This material was of sufficient purity for use in the next step, but an analytical sample was obtained in a separate preparation by chromatography on silica gel, developing with a step gradient of EtOAc in hexanes (5%, 10%, 12%, 15%, and 18%, by volume); nmr (CDCl$_3$) d: 1.48 (s, 9H, C(CH$_3$)$_3$), 3.57 (br s, 8H, piperazine CH$_2$'s), 4.00 (s, 3H, CH$_3$O); mass spectrum showed m/e 373 (M+).

Anal. Calcd. for C$_{14}$H$_{20}$N$_5$O$_5$Cl: C, 44.98; H, 5.39; N, 18.74. Found: C, 45.16; H, 5.44; N, 18.77.

EXAMPLE 138

6-[1-(4-BOC)piperazinyl]-4-[(1S,2S)-2-hydroxy-1-methylpropylamino]-2-methoxy-5-nitropyrimidine A mixture of the foregoing material prepared in Example 137 (7.81 g, 20.94 mmol), Et$_3$N (6.55 g, 9.0 mL, 64.7 mmol), and (1S,2S)-2-hydroxy-1-methylpropylammonium hydrogen D(−)-tartrate [5.15 g, 21.56 mmol, prepared as described in J. Amer. Chem. Soc, 74, 944 (1952) with slight modifications] was stirred together in sieve dried DMF (120 mL) overnight at room temperature. A precipitate formed and the mixture was evaporated to dryness in vacuo. The residue so obtained was partitioned between EtOAc and 10% aqueous Na$_2$CO$_3$ and the aqueous layer was washed several times with EtOAc. The pooled organic layers were washed with H₂O and evaporated to a yellow foam. This was chromatographed on a silica gel column (8×20 cm) developed with a step gradient of EtOAc in hexanes (20%, 25%, and 30% by volume). Fractions containing the required product were pooled and evaporated to dryness to give 7.02 g (16.48 mmol, 79% yield) of the title compound; nmr (CDCl₃) d: 1.23 (d, 3H, J=6.0 Hz, side chain CH₃), 1.29 (d, 3H, J=6.0 Hz, side chain CH₃), 1.47 (s, 9H, C(CH₃)₃), 2.39 (d, 1H, J=4.5 Hz, OH), 3.54 (br s, 8H, piperazine CH₂'s), 3.8–3.94 (m, 1H, side chain CH), 3.92 (s, 3H, CH₃O), 4.30 (m, 1H, side chain CH), 8.75 (br d, 1H, J=8.0 Hz, NH); mass spectrum (FAB) showed m/e 427 (M+1).

Anal. Calcd. for $C_{18}H_{30}N_6O_6$: C, 50.69; H, 7.09; N, 19.71. Found: C, 50.84; H, 7.14; N, 19.34.

EXAMPLE 139

5-Amino-6-[1-(4-BOC)piperazinyl]-4-[(1S,2S)-2-hydroxy-1-methylpropylamino]-2-methoxypyrimidine A solution of the foregoing material prepared in Example 138 (5.7 g, 13.38 mmol) in warm MeOH (150 mL) was allowed to cool to room temperature and the solution was then added to a suspension of 10% Pd on carbon (1.50 g) in MeOH (50 mL). This mixture was hydrogenated in a Parr apparatus at 42 p.s.i. overnight. An additional 1.27 g (2.98 mmol) of the starting material and 0.5 g of catalyst in MeOH (30 mL) was then added and the hydrogenation continued for an additional 4 hr. The reaction was then filtered through a Celite pad which was washed well with MeOH. The filtrate was evaporated to dryness to give 6.21 g (15.66 mmol, 96% yield) of the title compound as a tan solid; nmr (CDCl₃) d: 1.22 (d, 3H, J=6 Hz, side chain CH₃), 1.25 (d, 3H, J=6 Hz, side chain CH₃), 1.48 (s, 9H, C(CH₃)₃), 2.65 (br s, 2H, NH₂), 3.07 (br d, 1H, J=3.5 Hz, OH), 3.11–3.24 (m, 4H, piperazine CH₂'s), 3.48–3.6 (m, 4H, piperazine CH₂'s), 3.74–3.92 (m, 1H, side chain CH), 3.85 (s, 3H, CH₃O), 4.11 (m, 1H, side chain CH), 5.03 (d, 1H, J=8 Hz, NH); mass spectrum (FAB) showed m/e 397 (M+1).

Anal. Calcd. for $C_{18}H_{32}N_6O_4 \cdot 0.5H_2O$: C, 53.32; H, 8.08; N, 20.73. Found: C, 53.27; H, 8.08; N, 20.5.

EXAMPLE 140

6-[1-(4-BOC)piperazinyl]-9-[(1S,2S)-2-hydroxy-1-methylpropyl]-2-methoxypurine

To a solution of the foregoing material prepared in Example 139 (5.75 g, 14.5 mmol) and ethanol (70 mL) was added triethyl orthoformate (4.3 g, 4.82 mL, 29 mmol) and ethanolic HCl (1 mL of approx. 2.5M) and the solution was heated at 60° C. for 2.5 hr and then stirred overnight at room temperature. A small amount of 10% aqueous Na₂CO₃ was then added to neutraize the acid and the mixture was then concentrated to small volume and the liquid residue was partitioned between EtOAc and 10% aqueous Na₂CO₃. The organic layer was dried (MgSO₄), filtered and evaporated to dryness to give 5.73 g of a tan solid. This was purified by chromatography on a silica gel column (7×27 cm) developed with a step gradient of EtOAc in hexanes (20%, 30%, 40%, and 50% by volume). Fractions containing the required product were pooled and evaporated to dryness to give 4.79 g (11.78 mmol, 81% yield) of the title compound.

Anal. Calcd. for $C_{19}H_{30}N_4O_4$: C, 56.14; H, 7.44; N, 20.67. Found: C, 55.94; H, 7.37; N, 20.43.

EXAMPLE 141

6-[1-(4-BOC)piperazinyl]-9-[(1S,2R)-2-fluoro-1-methylpropyl]-2-methoxypurine

To a solution of the foregoing material prepared in Example 140 (4.69 g, 11.54 mmol) in dry CH₂Cl₂ (100 mL) was added MgO (2.3 g, 57.7 mmol) and the stirred suspension was cooled to −70° C. under a nitrogen blanket. Diethylaminosulfur trifluoride (DAST, 3.72 g, 3.0 mL, 23.08 mmol) was then added dropwise and upon completion of the addition, the reaction was allowed to rise to room temperature and was stirred overnight. The reaction was diluted with a large volume of Et₂O and then was poured into ice-cold 1M K₂HPO₄ (1 L). The layers were filtered to remove MgO and then separated, and the ethereal layer was further washed with 1M K₂HPO₄, dried (MgSO₄), filtered and evaporated to dryness to give 4.19 g of the crude product. This was purified by chromatography on a silica gel column (7×30 cm) developed with a step gradient of EtOAc in hexanes (5%, 10%, 15%, and 20% by volume). Fractions containing the required product were pooled and evaporated to dryness to give 2.76 g (6.76 mmol, 58% yield) of the title compound.

Anal. Calcd. for $C_{19}H_{29}N_6O_3F$: C, 55.87; H, 7.16; N, 20.57. Found: C, 55.84; H, 7.1; N, 20.46.

EXAMPLE 142

9-[(1S,2R)-2-Fluoro-1-methylpropyl]-2-methoxy-6-(1-piperazinyl)purine

The foregoing material prepared in Example 141 (2.74 g, 6.7 mmol) was deblocked using methanolic HCl (25 mL) in the usual fashion to give the title compound as a dihydrochloride salt (2.24 g, 5.89 mmol, 88% yield); mass spectrum (FAB) showed m/e 309 (M+1 for free base); [a]$_D$= −29.0° (H₂O).

Anal. Calcd. for $C_{14}H_{21}N_6OF \cdot 2HCl$: C, 44.1; H, 6.08; N, 22.04. Found: C, 44.15; H, 5.84; N, 21.78.

Conversion to free base: 1.1 g (2.89 mmol) of the 2HCl salt was dissolved in 1M K₂HPO₄ and this solution was extracted with CH₂Cl₂. The organic layers were pooled and evaporated to dryness and the residue was dissolved in MeOH and then evaporated to an oil. Damp crystals of the free base were obtained after blowing a nitrogen stream over this residue for some time. Yield 0.5591 g (1.81 mmol, 63%). Conversion to monohydrochloride: 50.6 mg (0.13 mmol) of the dihydrochloride salt and 40.24 mg (0.13 mmol) of the free base were mixed and EtOH (9 mL) was added. Dissolution was effected by warming on a steam bath and the volume was reduced to 1 mL by warming. White crystals were formed after cooling slowly overnight and these were filtered off, washed with a little EtOH and dried in vacuo. Yield 81.5 mg (0.24 mmol, 92%); m.p. 249°-250° C. (dec.)

Anal. Calcd. for $C_{14}H_{21}N_6OF \cdot HCl$: C, 48.77; H, 6.43; N, 24.37; Cl, 10.28. Found: C, 48.57; H, 6.36; N, 23.99; Cl, 10.5.

EXAMPLE 143

6-[1-(4-BOC)piperazinyl]-4-[(1R,2R)-2-hydroxy-1-methylpropylamino]-2-methoxy-5-nitropyrimidine This was prepared as described in Example 138 except that (1R,2R)-2-hydroxy-1-methylpropylammonium hydrogen L(−)-tartrate, prepared as described in J. Amer. Chem. Soc, 74, 944 (1952), was used in place of (1S,2S)-2-hydroxy-1-methylpropylammonium hydrogen D(−)-tartrate; nmr (CDCl$_3$)..d: 1.24 (d, 3H, J=6.0 Hz, side chain CH$_3$), 1.30 (d, 3H, J=6.0 Hz, side chain CH$_3$), 1.48 (s, 9H, C(CH$_3$)$_3$), 3.56 (br, s, 8H, piperazine CH$_2$'s), 3.90 (m, 1H, side chain CH), 3.93 (s, 3H, CH$_3$O), 4.36 (m, 1H, side chain CH).

EXAMPLE 144

5-Amino-6-[1-(4-BOC)piperazinyl]-4-[(1R,2R)-2-hydroxy-1-methylpropylamino]-2-methoxypyrimidine The foregoing material prepared in Example 143 was reduced as described in Example 139 for the enantiomer, to give the title compound; nmr (CDCl$_3$) d: 1.22 (d, 3H, J=6 Hz, side chain CH$_3$), 1.27 (d, 3H, J=6 Hz, side chain CH$_3$), 1.48 (s, 9H, C(CH$_3$)$_3$), 3.18 (m, 4H, piperazine CH$_2$'s), 3.56 (m, 4H, piperazine CH$_2$'s), 3.81 (m, 1H, side chain CH), 3.86 (s, 3H, CH$_3$O), 4.12 (m, 1H, side chain CH).

EXAMPLE 145

6-[1-(4-BOC)piperazinyl]-9-[(1R,2R)-2-hydroxy-1-methylpropyl]-2-methoxypurine

The foregoing material prepared in Example 144 was reacted with triethyl orthoformate as described in Example 140 for the enantiomer, to give the title compound.

EXAMPLE 146

6-[1-(4-BOC)piperazinyl]-9-[(1R,2S)-2-fluoro-1-methylpropyl]-2-methoxypurine

The foregoing material prepared in Example 145 was reacted with DAST as described in Example 141 for the enantiomer, to give the title compound.

EXAMPLE 147

9-[(1R,2S)-2-Fluoro-1-methylpropyl]-2-methoxy-6-(1-piperazinyl)purine

The foregoing material prepared in Example 146 was deblocked with methanolic HCl as described in Example 142 for the enantiomer, to give the title compound as the hydrochloride salt; mass spectrum (FAB) shows m/e 309 (M+1 for free base); [a]$_D$=+31.66° (H$_2$O).

Anal. Calcd. for C$_{14}$H$_{21}$N$_6$OF.HCl.0.25H$_2$O: C, 48.14; H, 6.49; N, 24.06; Cl, 10.15. Found: C, 48.04; H, 6.42; N, 23.84; Cl, 10.4.

EXAMPLE 148

6-[1-(4-BOC)piperazinyl]-9-[(1S,2S)-2-mesyloxy-1-methylpropyl]-2-methoxypurine

To a solution of the material prepared in Example 140 (0.8 g, 1.97 mmol) in sieve dried CH$_2$Cl$_2$ (25 mL) at 0° C. was added Et$_3$N (0.35 mL, 0.254 g, 2.51 mmol) followed by mesyl chloride (0.2 mL, 0.296 g, 2.58 mmol). This mixture was stirred at 0° C., under nitrogen for 1.5 hr. To the reaction was added 1M K$_2$HPO$_4$ and the mixture was extracted 3× with CH$_2$Cl$_2$. The pooled organic layers were dried (MgSO$_4$), filtered and evaporated to dryness to give 820 mg of crude product. This was purified by preparative TLC chromatography on silica gel plates developed with EtOAc:hexanes (3:1) to give 780 mg (1.60 mmol, 81% yield) of the title compound.

EXAMPLE 149

9-[(1S,2R)-2-Acetoxy-1-methylpropyl]-6-[1-(4-BOC)-piperazinyl]-2-methoxypurine

The foregoing material prepared in Example 148 (0.310 g, 0.63 mmol) was dissolved in DMSO (4 mL) and lithium acetate dihydrate (0.380 g, 3.72 mmol) was added. This mixture was stirred and heated under nitrogen at 100° C. for 15 hr. The reaction was then evaporated to dryness in vacuo and the residue was partitioned between 1M K$_2$HPO$_4$ and CH$_2$Cl$_2$. The pooled organic layers were dried (MgSO$_4$), filtered and evaporated to dryness to give 280 mg of crude product. This was purified by preparative TLC chromatography on silica gel plates developed with EtOAc:hexanes (3:1) to give 190 mg (0.42 mmol, 67% yield) of the title compound.

EXAMPLE 150

6-[1-(4-BOC)piperazinyl]-9-[(1S,2R)-2-hydroxy-1-methylpropyl]-2-methoxypurine

The foregoing material prepared in Example 149 was saponified by using a solution of 10% KOH in MeOH at room temperature for 1.5 hr. The reaction mixture was then poured into 1M K$_2$HPO$_4$ and the pH was adjusted further to <7 using 2.5M HCl. The mixture was extracted 4× with CHCl$_3$ and the pooled organic layers were dried (MgSO$_4$), filtered, and evaporated to dryness to give the title compound in 90% yield.

EXAMPLE 151

6-[1-(4-BOC)piperazinyl]-9-[(1S,2S)-2-fluoro-1-methylpropyl]-2-methoxypurine

The foregoing material prepared in Example 150 was reacted with DAST as described in Example 141 for the diastereomer, to give the title compound.

EXAMPLE 152

9-[(1S,2S)-2-Fluoro-1-methylpropyl]-2-methoxy-6-(1-piperazinyl)purine

The foregoing material prepared in Example 151 was deblocked with methanolic HCl as described in Example 142 for the diastereomer, to give the title compound as the dihydrochloride salt; [a]$_D$=−19.27° (H$_2$O).

Anal. Calcd. for C$_{14}$H$_{21}$N$_6$OF.2HCl: C, 44.10; H, 6.08; N, 22.04; Cl, 18.6. Found: C, 44.16; H, 6.1; N, 21.84; Cl, 18.85.

EXAMPLE 153

6-[1-(4-BOC)piperazinyl]-9-[(1R,2R)-2-mesyloxy-1-methylpropyl]-2-methoxypurine

The material prepared in Example 143 was mesylated with mesyl chloride in CH$_2$Cl$_2$/Et$_3$N as described in Example 148 for the enantiomer, to give the title compound.

EXAMPLE 154

9-[(1R,2S)-2-Acetoxy-1-methylpropyl]-6-[1-(4-BOC)-piperazinyl]-2-methoxypurine

The foregoing material prepared in Example 153 was treated with lithium acetate in DMSO at 100° C. as described in Example 149 for the enantiomer, to give the title compound.

EXAMPLE 155

6-[1-(4-BOC)piperazinyl]-9-[(1R,2S)-2-hydroxy-1-methylpropyl]-2-methoxypurine

The foregoing material prepared in Example 154 was saponified with KOH in MeOH as described in Example 150 for the enantiomer, to give the title compound.

EXAMPLE 156

6-[1-(4-BOC)piperazinyl]-9-[(1R,2R)-2-fluoro-1-methylpropyl]-2-methoxypurine

The foregoing material prepared in Example 155 was reacted with DAST as described in Example 141 for the diastereomer, to give the title compound.

EXAMPLE 157

9-[(1R,2R)-2-Fluoro-1-methylpropyl]-2-methoxy-6-(1-piperazinyl)purine

The foregoing material prepared in Example 156 was deblocked with methanolic HCl as described in Example 142 for the diastereomer, to give the title compound as a dihydrochloride salt; mass spectrum (FAB) shows m/e 309 (M+1 for free base); $[a]_D = +16.68°$ ($H_2O$).

Anal. Calcd. for $C_{14}H_{21}N_6OF \cdot 2.12HCl \cdot 0.3C_2H_5OH$: C, 43.90; H, 6.29; N, 21.04; Cl, 18.82. Found: C, 43.90; H, 6.13; N, 21.00; Cl, 18.83 (presence of $0.3C_2H_5OH$ verified by $^1H$ nmr).

TABLE 1

PROTON NMR SHIFT DATA FOR 6-(1-PIPERAZINYL)PURINES

| Example | Piperazine Methylene Resonances | Heterocyclic Protons | Others |
|---|---|---|---|
| 1[a] | 3.60(m), 4.25(m) | 7.95(s), 8.39(s) | 1.50(s)-C(CH$_3$)$_3$ |
| 2[a] | 3.50(m), 4.30(m) 3.82(s)-N9—CH$_3$ | 7.70(s), 8.38(s) | 1.50(s)-C(CH$_3$)$_3$ |
| 3[a] | 3.60(m), 4.00(m) 2.50(m)-N3—CH$_3$ | 7.85(s), 8.0(s) | 1.50(s)-C(CH$_3$)$_3$ |
| 4[b] | 3.55(m), 4.55(m) | 8.25(s), 8.43(s) | 3.90(s)-N9—CH$_3$ |
| 7[a] | 3.60(m), 4.30(m) 3.65–4.00(m) 4.35(s) 4.40(d) 5.00(s) 5.15(s) 5.70(d) 6.50(d) 7.40(m) | 7.70(s), 8.10(s) | 2.95(s) |
| 8[b] | 3.60(m), 3.90(m) 4.10(m) 4.12(m) 4.40(m) 6.00(d) 7.40(m) | 8.20(s), 8.30(s) | 2.90(m) |
| 11[a] | 3.58(m), 4.29(m) 2.60(s)-C8—CH$_3$ | 8.29(s) | 1.46(s)-C(CH$_3$)$_3$ |
| 12[b] | 3.59(m), 4.29(m) | 8.30(s) | 2.67(s)-C8—CH$_3$ |
| 14[a] | 3.55(m), 4.70(m) 2.50(s)-C8—CH$_3$ 3.68(s)-C9—CH$_3$ | 8.25(s) | 1.42(s)-C(CH$_3$)$_3$ |
| 15[b] | 3.55(m), 4.42(m) 3.78(s)-C9—CH$_3$ | 8.36(s) | 2.62(s)-C8—CH$_3$ |
| 22[a] | 3.47(m), 4.13(m) | 8.22(s) | 1.41(s)-C(CH$_3$)$_3$ 3.47(s)-N9—CH$_3$ |
| 23[b] | 3.44(m), 4.40(m) | 8.32(s) | 3.74(s)-N9—CH$_3$ |
| 24[a] | 3.59(m), 4.29(m) | 8.32(s) | 1.49(s)-C(CH$_3$)$_3$ |
| 25[a] | 3.42(m), 4.06(m) | 7.99(s) | 1.44(s)-C(CH$_3$)$_3$ 2.34(d)-C8—NHC$\underline{H}_3$ |
| 26[b] | 3.55(m), 4.54(m) | 8.44(s) | |
| 28[a] | 3.56(m), 4.26(m) | 7.64(s) | 1.49(s)-C(CH$_3$)$_3$ 2.58(s)-C2—CH$_3$ 3.78(s)-N9—CH$_3$ |
| 29[a] | 3.56(m), 4.20(m) | | 1.49(s)-C(CH$_3$)$_3$ 2.54(s)-C2—CH$_3$ 3.72(s)-N9—CH$_3$ |
| 30[a] | 3.54(m), 4.16(m) | | 1.48(s)-C(CH$_3$)$_3$ 2.52(s)-C2—CH$_3$ 3.09(d)-C8—NHC$\underline{H}_3$ 3.46(s)-N9—CH$_3$ |
| 31[a] | 3.44(m), 4.08(m) | | 1.38(s)-C(CH$_3$)$_3$ 2.42(s)-C2—CH$_3$ 2.83(s)-C8—N(CH$_3$)$_2$ 3.50(s)-N9—CH$_3$ |
| 32[b] | 3.53(m), 4.36(m) | | 2.50(s)-C2—CH$_3$ 3.15(s)-C8—NHC$\underline{H}_3$ 3.62(s)-N9—CH$_3$ |
| 33[a] | 3.36–3.50(m), 4.06(m) | | 1.38(s)-C(CH$_3$)$_3$ 1.85(m)-(CH$_2$)$_2$— 2.42(s)-C2—CH$_3$ 3.36–3.50(m)-CH$_2$NCH$_2$— 3.54(s)-N9—CH$_3$ |
| 34[a] | 3.44(m), 4.04(m) | | 1.40(s)-C(CH$_3$)$_3$ |

TABLE 1-continued

PROTON NMR SHIFT DATA FOR 6-(1-PIPERAZINYL)PURINES

| Example | Piperazine Methylene Resonances | Heterocyclic Protons | Others |
|---|---|---|---|
| | | | 2.43(s)-C2—CH$_3$ |
| | | | 3.20(s)-C8—OCH$_3$ |
| | | | 4.00(s)-N9—CH$_3$ |
| 35[b] | 3.50(m), 4.46(m) | | 2.68(s)-C2—CH$_3$ |
| | | | 3.13(s)-C8—N(CH$_3$)$_2$ |
| | | | 3.76(s)-N9—CH$_3$ |
| 36[b] | 3.50(m), 4.28(m) | | 2.08(m)-(CH$_2$)$_2$— |
| | | | 2.67(s)-C2—CH$_3$ |
| | | | 3.78–3.98(m)- |
| | | | CH$_2$NCH$_2$—, N9—CH$_3$ |
| 37[a] | 3.42–3.54(m), 4.02–4.16(m) | 8.20(s) | 1.42(s)-C(CH$_3$)$_3$ |
| | | | 3.48(s)-C8—OCH$_3$ |
| | | | 4.08(s)-N9—CH$_3$ |
| 38[a] | 3.53(m), 4.18(m) | 8.24(s) | 1.47(s)-C(CH$_3$)$_3$ |
| | | | 1.95(s)-C8—N(CH$_3$)$_2$ |
| | | | 3.62(s)-N9—CH$_3$ |
| 39[b] | 2.89(m), 3.88–4.14(m) | 8.15(s) | 3.43(s)-C8—OCH$_3$ |
| | | | 3.88–4.14(s)-N9—CH$_3$ |
| 40[a] | 3.40–3.60(m), 4.51(m) | 8.14(s) | 1.42(s)-C(CH$_3$)$_3$ |
| | | | 1.92(m)-(CH$_2$)$_2$— |
| | | | 3.40–3.60(m)-CH$_2$NCH$_2$— |
| | | | 4.62(s)-N9—CH$_3$ |
| 41[a] | 3.56(m), 4.25(m) | 8.28(s) | 1.48(s)-C(CH$_3$)$_3$ |
| | | | 2.72(s)-C8—SCH$_3$ |
| | | | 3.65(s)-N9—CH$_3$ |
| 42[b] | 3.56(m), 4.20(m) | 8.48(s) | 2.17(m)-(CH$_2$)$_2$— |
| | | | 3.97(m)-N9—CH$_3$, —CH$_2$NCH$_2$— |
| 43[b] | 3.56(m), 4.38(m) | 8.46(s) | 3.27(s)-C8—N(CH$_3$)$_2$ |
| | | | 3.86(s)-N9—CH$_3$ |
| 45[a] | 3.56(m), 4.24(m) | | 1.49(s)-C(CH$_3$)$_3$ |
| | | | 2.52(s)-C2 or C8—CH$_3$ |
| | | | 2.56(s)-C2 or C8—CH$_3$ |
| | | | 3.68(s)-N9—CH$_3$ |
| 46[b] | 3.46(m), 4.55(m) | | 2.60(s)-C2 or C8—CH$_3$ |
| | | | 2.65(s)-C2 or C8—CH$_3$ |
| | | | 3.74(s)-N9—CH$_3$ |
| 48[a] | 3.57(m), 4.28(m) | | 1.50(s)-C(CH$_3$)$_3$ |
| | | | 2.62(s)-C2/C8—CH$_3$'s |
| 49[b] | 3.49(m), 4.45(m) | | 2.61(s)-C2 or C8—CH$_3$ |
| | | | 2.64(s)-C2 or C8—CH$_3$ |
| 50[a] | 3.58(m), 3.80–4.80(br) | 7.88(s) | 1.50(s)-C(CH$_3$)$_3$ |
| 51[a] | 3.46(m), 3.80–4.80(br) | 8.17(s) | 1.43(s)-C(CH$_3$)$_3$ |
| | | | 3.69(s)-N9—CH$_3$ |
| 52[b] | 3.44(m), 4.42(m) | 8.03(s) | 3.72(s)-N9—CH$_3$ |
| 53[a] | 3.53(m), 4.17(m) | 7.45(s) | 1.47(s)-C(CH$_3$)$_3$ |
| | | | 3.64(s)-N9—CH$_3$ |
| | | | 3.75(s)-morpholine CH$_2$'s |
| 54[b] | 3.40(m), 4.38(m) | 8.00(s) | 3.74(s)-N9—CH$_3$ |
| | | | 3.80(m)-morpholine CH$_2$'s |
| 55[a] | 3.48–3.62(m), 4.19(m) | 7.40(s) | 1.48(s)-C(CH$_3$)$_3$ |
| | | | 1.94(m)-(CH$_2$)$_2$— |
| | | | 3.66(s)-N9—CH$_3$ |
| | | | 3.48–3.62(m)-CH$_2$NCH$_2$— |
| 56[b] | 3.46(m), 4.53 | 7.82(s) | 2.06(m)-(CH$_2$)$_2$— |
| | | | 3.62(m)-CH$_2$NCH$_2$— |
| | | | 3.81(s)-N9—CH$_3$ |
| 57[a] | 3.54(m), 4.20(m) | 7.42(s) | 1.48(s)-C(CH$_3$)$_3$ |
| | | | 3.00(d)-C2—NHC̲H$_3$ |
| | | | 3.66(s)-N9—CH$_3$ |
| 58[b] | 3.48(m), 4.57(m) | 7.84(s) | 3.02(s)-C2—NHC̲H$_3$ |
| | | | 3.78(s)-N9—CH$_3$ |
| 59[a] | 3.54(m), 4.19(m) | 7.41(s) | 1.48(s)-C(CH$_3$)$_3$ |
| | | | 3.17(s)-C2—N(CH$_3$)$_2$ |
| | | | 3.66(s)-N9—CH$_3$ |
| 60[b] | 3.46(m), 4.52(m) | 7.88(s) | 3.26(s)-C2—N(CH$_3$)$_2$ |
| | | | 3.84(s)-N9—CH$_3$ |
| 61[a] | 3.54(m), 4.13(m) | | 1.48(s)-C(CH$_3$)$_3$ |
| | | | 3.16(s)-C2—N(CH$_3$)$_2$ |
| | | | 3.60(s)-N9—CH$_3$ |
| 62[a] | 3.48–3.60(m) 4.14(m) | | 1.49(s)-C(CH$_3$)$_3$ |
| | | | 2.88(s)-C2—N(CH$_3$)$_2$ |
| | | | 3.16(s)-C8—N(CH$_3$)$_2$ |
| | | | 3.53(s)-N9—CH$_3$ |
| 62[b] | 2.84–2.96(m), | | 2.90(m)-C2—N(CH$_3$)$_2$ |

TABLE 1-continued

| | PROTON NMR SHIFT DATA FOR 6-(1-PIPERAZINYL)PURINES | | |
|---|---|---|---|
| Example | Piperazine Methylene Resonances | Heterocyclic Protons | Others |
| | 4.03(m) | | 3.10(s)-C8—N(CH$_3$)$_2$ |
| 64[a] | 3.54(m), 4.24(m) | 7.56(s) | 1.48(s)-C(CH$_3$)$_3$ |
| | | | 3.73(s)-N9—CH$_3$ |
| | | | 3.96(s)-C2—OCH$_3$ |
| 65[b] | 3.42(m), 4.44(m) | 8.00(s) | 3.72(s)-N9—CH$_3$ |
| | | | 4.00(s)-C2—OCH$_3$ |
| 66[a] | 3.54(m), 4.23(m) | 7.54(s) | 1.38(d)-OCH(C$\underline{H}$$_3$)$_2$ |
| | | | 1.48(s)-C(CH$_3$)$_3$ |
| | | | 3.70(s)-N9—CH$_3$ |
| | | | 5.26(m)-C2—OCH— |
| 67[b] | 3.48(m), 4.52(m) | 8.10(s) | 1.40(d)-OCH(C$\underline{H}$$_3$)$_2$ |
| | | | 3.80(s)-N9—CH$_3$ |
| | | | 5.42(m)-C2—OCH— |
| 68[a] | 3.56(m), 4.24(m) | 7.55(s) | 3.52(s)-N9—CH$_3$ |
| | | | 1.48(s)-C(CH$_3$)$_3$ |
| | | | 3.21(s)-C2—N(CH$_3$)$_2$ |
| 69[b] | 3.46(m), 4.48(m) | 7.97(s) | 3.24(s)-C2—N(CH$_3$)$_2$ |
| 71[b] | 3.28–3.38(m), | 7.98(s) | 3.01(s)-NCH$_3$ |
| | 3.60–3.80(m), | | 3.25(s)-C2—N(CH$_3$)$_2$ |
| | 5.28–5.42(m) | | |
| 72[b] | 2.80(m), 4.43(m) | 7.42(s) | 2.50(s)-NCH$_3$ |
| | | | 3.17(s)-C2—N(CH$_3$)$_2$ |
| | | | 3.66(s)-N9—CH$_3$ |
| 73[b] | 3.46(m), 4.46(m) | 8.00(s) | |
| 74[a] | 3.58(m), 4.28(m) | 7.69(s) | 0.95(t)-CH$_2$CH$_2$CH$_3$ |
| | | | 1.48(s)-C(CH$_3$)$_3$ |
| | | | 1.90(m)-CH$_2$C$\underline{H}$$_2$CH$_3$ |
| | | | 4.12(t)-NC$\underline{H}$$_2$CH$_2$CH$_3$ |
| 75[a] | 3.58(m), 4.27(m) | 7.59(s) | 0.96(t)-CH$_2$CH$_2$C$\underline{H}$$_3$ |
| | | | 1.48(s)-C(CH$_3$)$_3$ |
| | | | 1.89(m)-CH$_2$CH$_2$CH$_3$ |
| | | | 3.97(s)-OCH$_3$ |
| | | | 4.08(t)-NC$\underline{H}$$_2$CH$_2$CH$_3$ |
| 76[b] | 3.46(m), 4.48(m) | 8.12(s) | 0.88(t)-CH$_2$CH$_2$C$\underline{H}$$_3$ |
| | | | 1.86(m)-CH$_2$C$\underline{H}$$_2$CH$_3$ |
| | | | 4.03(s)-OCH$_3$ |
| | | | 4.14(t)-NC$\underline{H}$$_2$CH$_2$CH$_3$ |
| 77[a] | 3.57(m), 4.26(m) | 7.61(s) | 0.94(t)-CH$_2$CH$_2$C$\underline{H}$$_3$ |
| | | | 1.49(s)-C(CH$_3$)$_3$ |
| | | | 1.89(m)-CH$_2$C$\underline{H}$$_2$CH$_3$ |
| | | | 2.57(s)-SCH$_3$ |
| | | | 4.10(t)-NC$\underline{H}$$_2$CH$_2$CH$_3$ |
| 78[b] | 3.44(m), 4.46(m) | 8.05(s) | 0.86(t)-CH$_2$CH$_2$C$\underline{H}$$_3$ |
| | | | 1.84(m)-CH$_2$C$\underline{H}$$_2$CH$_3$ |
| | | | 2.59(s)-SCH$_3$ |
| | | | 4.12(t)-NC$\underline{H}$$_2$CH$_2$CH$_3$ |
| 79[a] | 3.60(m), 4.30(m) | 7.86(s) | 1.50(s)-C(CH$_3$)$_3$ |
| | | | 3.38(s)-OCH$_3$ |
| | | | 5.51(s)-NCH$_2$O |
| 80[a] | 3.58(m), 4.17(m) | 8.72(s) | 1.49(s)-C(CH$_3$)$_3$ |
| | | | 2.43(t)-CH$_2$C$\underline{H}$$_3$ |
| | | | 3.37(s)-OCH$_3$ |
| | | | 4.49(q)-C$\underline{H}$$_2$CH$_3$ |
| | | | 5.46(s)-NCH$_2$O |
| 81[b] | 3.36–3.50(m), | 8.09(s) | 1.38(t)-CH$_2$C$\underline{H}$$_3$ |
| | 4.32–4.49(m) | | 3.39(s)-OCH$_3$ |
| | | | 5.52(s)-NCH$_2$O |
| | | | 6.27(s)-CHCOO |
| 82[a] | 3.52–3.64(m), | 7.87(s) | 1.19(t)-OCH$_2$C$\underline{H}$$_3$ |
| | 4.29(br m) | | 1.50(s)-C(CH$_3$)$_3$ |
| | | | 3.52-3.64-OC$\underline{H}$$_2$CH$_3$ |
| | | | (overlap with piperazine) |
| | | | 5.55(s)-NCH$_2$O |
| 83[a] | 3.50–3.66(m), | 7.76(s) | 1.18(s)-OC$\underline{H}$$_2$CH$_3$ |
| | 4.16–4.40(br m) | | 1.50(s)-C(CH$_3$)$_3$ |
| | | | 3.50-3.66-OC$\underline{H}$$_2$CH$_3$ |
| | | | (overlap with piperazine) |
| | | | 3.98(s)-OCH$_3$ |
| | | | 5.52(s)-NCH$_2$O |
| 84[b] | 3.45(m), 4.46(m) | 8.12(s) | 1.17(t)-OCH$_2$C$\underline{H}$$_3$ |
| | | | 3.68(q)-OC$\underline{H}$$_2$CH$_3$ |
| | | | 4.00(s)-OCH$_3$ |

TABLE 1-continued

PROTON NMR SHIFT DATA FOR 6-(1-PIPERAZINYL)PURINES

| Example | Piperazine Methylene Resonances | Heterocyclic Protons | Others |
|---|---|---|---|
| 85[a] | 3.58(m), 4.19(br m) | 7.82(s) | 5.59(s)-NCH$_2$O<br>6.26(s)-OHCOO<br>0.44(m) and 0.68(m), cyclopropyl methylenes<br>1.44-1.22(m)-CH<br>1.49(s)-C(CH$_3$)$_3$<br>4.01(d)-NCH$_2$ |
| 86[a] | 3.58(m), 4.27(br m) | 7.70(s) | 0.43(m) and 0.64(m) cyclopropyl methylenes<br>1.22-1.38(m)-CH<br>1.42(t)-OCH$_2$C̲H̲$_3$<br>1.49(s)-C(CH$_3$)$_3$<br>3.96(d)-NCH$_2$<br>4.40(q)-OC̲H̲$_2$CH$_3$ |
| 87[b] | 3.48(m), 4.40-4.58(m) | 8.24(s) | 0.46(m) and 0.67(m), cyclopropyl methylenes<br>1.26-1.44(m)-CH<br>1.40(t)-OCH$_2$C̲H̲$_3$<br>4.04(d)-NCH$_2$<br>4.48(q)-OC̲H̲$_2$CH$_3$ |
| 88[a] | 3.58(m), 4.18-4.40(m) | 7.82(s) | (overlap with piperazine)<br>1.49(s)-C(CH$_3$)$_3$<br>3.34(s)-OCH$_3$<br>3.70(t)-NCH$_2$C̲H̲$_2$O<br>4.18-4.40-NC̲H̲$_2$CH$_2$O |
| 89[a] | 3.57(m), 4.16-4.38(m) | 7.70(s) | (overlap with piperazine)<br>1.49(s)-C(CH$_3$)$_3$<br>3.33(s)-OCH$_3$<br>3.70(t)-NCH$_2$C̲H̲$_2$O<br>3.96(s)-C$_2$—OCH$_3$<br>4.16-4.38-NC̲H̲$_2$CH$_2$O |
| 90[b] | 3.48(m), 4.49(m) | 8.10(s) | (overlap with piperazine)<br>3.36(s)-OCH$_3$<br>3.86(t)-NCH$_2$C̲H̲$_2$O<br>4.04(s)-C$_2$—OCH$_3$<br>4.40(t)-NC̲H̲$_2$CH$_2$O |
| 91[a] | 3.59(m), 4.28(br m) | 7.91(s) | 1.49(s)-C(CH$_3$)$_3$<br>2.14(s)-SCH$_3$<br>5.17(s)-NCH$_2$S |
| 92[a] | 3.58(m), 4.27(br m) | 7.77(s) | 1.50(s)-C(CH$_3$)$_3$<br>2.15(s)-SCH$_3$<br>3.97(s)-OCH$_3$<br>5.15(s)-NCH$_2$S |
| 93[b] | 3.46(m), 4.45(m) | 8.09(s) | 2.14(s)-SCH$_3$<br>3.98(s)-OCH$_3$<br>5.22(s)-NCH$_2$S |
| 94[a] | 3.56-3.70(m), 4.30(br m) | 7.87(s) | 6.27(s)-CHCOO<br>−0.02(s)-Si(CH$_3$)$_3$<br>0.85(d of d)-CH$_2$Si<br>1.50(s)-C(CH$_3$)$_3$<br>3.56-3.70-OC̲H̲$_2$CH$_2$<br>(overlap with piperazine)<br>5.55(s)-NCH$_2$O |
| 95[a] | 3.52-3.68(m), 4.27 (br m) | 7.73(s) | −0.04(s)-Si(CH$_3$)$_3$<br>0.92(d of d)-CH$_2$Si<br>1.48(s)-C(CH$_3$)$_3$<br>3.52-3.68-OC̲H̲$_2$CH$_2$<br>(overlap with piperazine)<br>3.97(s)-OCH$_3$<br>5.51(s)-NCH$_2$O |
| 96[a] | 3.60(m), 4.31(br m) | 7.77(s) | 1.49(s)-C(CH$_3$)$_3$<br>4.00(s)-OCH$_3$ |
| 97[a] | 3.58(m), 4.18-4.52(br m) | 7.66(s) | 1.49(s)-C(CH$_3$)$_3$<br>3.95(s)-OCH$_3$<br>4.18-4.52(d of t)-NCH$_2$<br>(overlap with piperazine)<br>4.74(d of t)-CH$_2$F |
| 98[b] | 3.48(m), 4.42-4.64(m) | 8.10(s) | 4.02(s)-OCH$_3$<br>4.42-4.64(d of t)-NCH$_2$<br>(overlap with piperazine)<br>4.84(d of t)-CH$_2$F |
| 99[a] | 3.58(m), 4.28(br m) | 7.82(s) | 1.49(s)-C(CH$_3$)$_3$<br>2.49(t)-CH<br>3.98(s)-OCH$_3$<br>4.90(d)-NCH$_2$ |
| 100[a] | 3.58(m), 4.26(br m) | 7.73(s) | 1.49(s)-C(CH$_3$)$_3$ |

TABLE 1-continued

PROTON NMR SHIFT DATA FOR 6-(1-PIPERAZINYL)PURINES

| Example | Piperazine Methylene Resonances | Heterocyclic Protons | Others |
|---|---|---|---|
| 101[b] | 3.43(m), 4.44(m) | 8.08(s) | 3.98(s)-OCH$_3$<br>5.66(d)-CH$_2$<br>7.31(t)-NCH<br>2.90(t)-CH<br>3.98(s)-OCH$_3$<br>4.90(br s)-NCH$_2$ |
| 102[b] | 3.44(m), 4.42(m) | 8.00(s) | 3.98(s)-OCH$_3$<br>5.78(d)-CH$_2$<br>7.10(t)-NCH |
| 103[a] | 3.58(m), 4.28(br m) | 7.59(s) | 1.48(s)-C(CH$_3$)$_3$<br>3.86(s)-OCH$_3$<br>4.72(d of t)-NCH$_2$<br>5.13-5.33(m)-CH=$\underline{CH_2}$<br>6.03(m)-CH |
| 104[b] | 3.46(m), 4.49(m) | 8.06(s) | 4.01(s)-OCH$_3$<br>4.72-4.84-NCH$_2$<br>(overlap with H$_2$O)<br>4.96-5.34(m)-CH=$\underline{CH_2}$<br>6.06(m)-CH |
| 107[a] | 3.57(m), 4.28(m) | 7.65(s) | 1.0-1.23(m)-cyclopropyl methylenes<br>1.35(t)-CH$_3$<br>1.49(s)-C(CH$_3$)$_3$<br>2.86(q)-$\underline{CH_2}$CH$_3$<br>3.38-3.50(m)-NCH |
| 108[a] | 3.00(m), 4.27(m) | 7.64(s) | 0.99-1.22(m)-cyclopropyl methylenes<br>1.34(t)-CH$_3$<br>2.84(q)-$\underline{CH_2}$CH$_3$<br>3.42(m)-NCH |
| 112[a] | 3.59(m), 4.30(m) | 7.77(s) | 1.34(t)-CH$_2$$\underline{CH_3}$<br>1.51(s)-C(CH$_3$)$_3$<br>2.83(q)-$\underline{CH_2}$CH$_3$<br>4.80(q)-$\underline{CH_2}$CF$_3$ |
| 113[a] | 3.03(m), 4.30(m) | 7.75(s) | 1.33(t)-CH$_2$$\underline{CH_3}$<br>2.82(q)-$\underline{CH_2}$CH$_3$<br>4.79(q)-$\underline{CH_2}$CF$_3$ |
| 114[a] | 3.59(m), 4.29(br m) | 7.70(s) | 1.49(s)-C(CH$_3$)$_3$<br>2.31(s)-COCH$_3$<br>5.00(s)-NCH$_2$CO |
| 115[a] | 3.59(m), 4.29(br m) | 7.79(s) | 1.48(s)-C(CH$_3$)$_3$<br>1.63(t)-CF$_2$$\underline{CH_3}$<br>4.51(t)-N$\underline{CH_2}$CF$_2$ |
| 116[a] | 3.57(m), 4.26(br m) | 7.66(s) | 1.48(s)-C(CH$_3$)$_3$<br>1.58(t)-CF$_2$$\underline{CH_3}$<br>3.96(s)-OCH$_3$<br>4.46(t)N$\underline{CH_2}$CF$_2$ |
| 117 | 3.55(m), 4.26(br m) | 7.76(s) | 1.88(s)-C(CH$_3$)$_3$<br>4.44(d of t)-N$\underline{CH_2}$CH$_2$F<br>4.72(d of t)-NCH$_2$$\underline{CH_2}$F |
| 119[a] | 3.57(m), 4.28(m) | 7.65(s) | 1.33(t)-CH$_2$$\underline{CH_3}$<br>1.48(s)-C(CH$_3$)$_3$<br>2.84(q)-$\underline{CH_2}$CH$_3$<br>3.79(s)-NCH$_3$ |
| 120[b] | 3.59(m), 4.72(m) | 8.22(s) | 1.43(t)-CH$_2$$\underline{CH_3}$<br>3.05(q)-$\underline{CH_2}$CH$_3$<br>3.97(s)-NCH$_3$ |
| 121[a] | 3.58(m), 4.26(br m) | 7.77(s) | 1.50(s)-C(CH$_3$)$_3$<br>1.56(d)-CH($\underline{CH_3}$)$_2$<br>4.84(m)-$\underline{CH}$(CH$_3$)$_2$ |
| 122[a] | 3.54(m), 4.04(br m) | 7.63(s) | 1.48(s)-C(CH$_3$)$_3$<br>1.55(d)-CH($\underline{CH_3}$)$_2$<br>3.94(s)-OCH$_3$<br>4.74(m)-$\underline{CH}$(CH$_3$)$_2$ |
| 123[b] | 3.43(m), 4.44(m) | 8.06(s) | 1.54(d)-CH($\underline{CH_3}$)$_2$<br>3.97(s)-OCH$_3$<br>4.68(m)-$\underline{CH}$(CH$_3$)$_2$ |
| 124[a] | 3.59(m), 4.28(br m) | 7.59(s) | 1.50(s)-C(CH$_3$)$_3$<br>2.28(s)-COCH$_3$<br>3.95(s)-OCH$_3$<br>4.94(s)-NCH$_2$O |
| 125[b] | 3.42(m), 4.45(m) | 7.88(s) | 2.37(s)-COCH$_3$<br>3.94(s)-OCH$_3$ |

TABLE 1-continued

| PROTON NMR SHIFT DATA FOR 6-(1-PIPERAZINYL)PURINES | | | |
|---|---|---|---|
| Example | Piperazine Methylene Resonances | Heterocyclic Protons | Others |
| 126[b] | 3.53(m), 4.56(m) | 8.15(s) | 5.22(s)-NCH$_2$CO<br>1.82(t)-CF$_2$C$\underline{H}_3$<br>4.09(s)-OCH$_2$<br>4.62(t)-NC$\underline{H}_2$CF$_2$ |
| 130[a] | 3.60(m), 4.35(m) | 7.85(s) | 1.41(t)-CH$_2$C$\underline{H}_3$<br>1.49(s)-C(CH$_3$)$_3$<br>2.92(q)-C$\underline{H}_2$CH$_3$ |
| 131[a] | 3.59(m), 4.31(m) | 7.77(s) | 1.33(t)-CH$_2$C$\underline{H}_3$<br>1.50(s)-C(CH$_3$)$_3$<br>2.82(q)-C$\underline{H}_2$CH$_3$<br>4.48(d of t)-NC$\underline{H}_2$CH$_2$F<br>6.77(d of t)-NCH$_2$C$\underline{H}_2$F |
| 132[b] | 3.58(m), 4.60–5.14(m) | 8.31(s) | 1.42(t)-CH$_2$C$\underline{H}_3$<br>3.03(q)-C$\underline{H}_2$CH$_3$<br>4.60–5.14(m)-NC$\underline{H}_2$C$\underline{H}_2$F (overlap with piperazine and HDO). |
| 145[a] | 3.58(m), 4.31(br m) | 7.65(s) | 1.10(d)-CH$_3$<br>1.50(s)-C(CH$_3$)$_3$<br>1.61(d)-CH$_3$<br>3.96(s)-OCH$_3$<br>4.17(m)-CH(N)<br>4.48(m)-CH(O) |
| 146[a] | 3.50(m), 4.32(br m) | 7.67(s) | 1.27(s)-CH$_3$<br>1.39(dd)-C(CH$_3$)<br>1.41(s)-C(CH$_3$)<br>1.52(d)-CH$_3$<br>4.55, 4.67(d, m)-CH<br>4.75, 4.99(d, m)-CH |
| 147[b] | 3.47(m), 4.46(m) | 8.14(s) | 1.35, 1.48(dd)-CH$_3$<br>1.65(d)-CH$_3$<br>3.99(s)-CH$_3$O<br>4.61(m)-CH<br>5.17(m)-CH |
| 148[a] | 3.57(m), 4.30(b, m) | 7.71(s) | 1.34(d)-CH$_3$<br>1.49(s)-C(CH$_3$)$_3$<br>1.66(d)-CH$_3$<br>2.86(s)-CH$_3$SO$_3$<br>3.96(s)-CH$_3$O<br>4.81(m)CH<br>5.22(m)CH |
| 149[a] | 3.57(m), 4.29(bm) | 7.64(s) | 1.24(d)-CH$_3$<br>1.50(s)-C(CH$_3$)$_3$<br>1.60(d)-CH$_3$<br>2.04(s)-CH$_3$CO$_2$<br>3.97(s)-CH$_3$O<br>4.83(m)-CH<br>5.21(m)CH |
| 150[a] | 3.56(m), 4.29(bm) | 7.62(s) | 1.24(d)-CH$_3$<br>1.48(s)-C(CH$_3$)$_3$<br>1.54(d)-CH$_3$<br>3.94(s)-CH$_3$O<br>4.25(m)-CH<br>4.45(m)-CH |
| 151[a] | 3.56(m), 4.29(bm) | 7.72(d) | 1.11, 1.23(dd)-CH$_3$<br>1.44(s)-C(CH$_3$)$_3$<br>1.62(s)-CH$_3$<br>3.95(s)-CH$_3$O<br>4.65, 4.80(dm)-CH<br>4.84, 5.09(dm)-CH |
| 152[b] | 3.26(m), 4.49(m) | 8.82(s) | 1.19, 1.33(dd)-CH$_3$<br>1.64(d)-CH$_3$<br>5.17, 4.93(dm)-CH<br>4.67(m)-CH |
| 153[a] | 3.55(m), 4.25(bm) | 7.68(s) | 1.31(d)-CH$_3$<br>1.45(s)-C(CH$_3$)$_3$<br>1.63(d)-CH$_3$<br>2.82(s)-CH$_3$SO$_3$<br>3.93(s)-CH$_3$O<br>4.76(m)-CH<br>5.15(m)CH |
| 154[a] | 3.59(m), 4.28(bm) | 7.60(s) | 1.25(d)-CH$_3$<br>1.50(s)-C(CH$_3$)$_3$<br>1.61(d)-CH$_3$<br>2.05(s)-CH$_3$CO$_2$<br>3.97(s)-CH$_3$O |

TABLE 1-continued
PROTON NMR SHIFT DATA FOR 6-(1-PIPERAZINYL)PURINES

| Example | Piperazine Methylene Resonances | Heterocyclic Protons | Others |
|---|---|---|---|
| 155[a] | 3.59(m), 4.32(bm) | 7.63(s) | 4.82(m)-CH<br>5.20(m)-CH<br>1.26(d)-CH$_3$<br>1.50(s)-C(CH$_3$)$_3$<br>1.56(d)-CH$_3$<br>3.96(s)-CH$_3$O<br>4.27(m)-CH<br>4.46(m)-CH |
| 156[a] | 3.58(m), 4.28(bm) | 7.73(s) | 1.12, 1.24(dd)-CH$_3$<br>1.49(s)-C(CH$_3$)$_3$<br>1.62(d)-CH$_3$<br>3.95(s)-CH$_3$O<br>4.66, 4.80(dm)-CH<br>5.10, 4.85(dm)-CH |
| 157[b] | 3.44(m), 4.47(bm) | 8.12(d) | 1.17, 1.30(dd)-CH$_3$<br>1.62(d)-CH$_3$<br>3.98(s)-CH$_3$O<br>4.7, 4.8(dm)-CH<br>4.93, 5.22(dm)-CH |
| 140[a] | 3.58(m), 4.30(bm) | 7.64(s) | 1.09(d)-CH$_3$<br>1.49(s)-C(CH$_3$)$_3$<br>1.60(d)-CH$_3$<br>3.95(s)-CH$_3$O<br>4.17(m)-CH<br>4.47(m)-CH |
| 141[a] | 3.55(m), 4.26(bm) | 7.71(s) | 1.34, 1.46(dd)-CH$_3$<br>1.47(s)-C(CH$_3$)$_3$<br>1.58(d)-CH$_3$<br>3.93(s)-CH$_3$O<br>4.63, 4.76(m)-CH<br>4.80, 5.06(dm)-CH |
| 142[b] | 3.46(m), 4.48(m) | 8.21(d) | 1.32, 1.45(dd)-CH$_3$<br>1.64(d)-CH$_3$<br>4.02(s)-CH$_3$O<br>N4.8(m)-CH<br>4.90, 5.18(dm)-CH |

All measured at 200 MHz in [a]CDCl$_3$ or [b]D$_2$O
Chemical shifts in w ppm from TMS (CDCl$_3$) or TSP (D$_2$O)

TABLE 2
PROPERTIES OF OTHER ALKYL 6-(1-PIPERAZINYL)PURINES

| Substituent | Salt Form | 200 MHz Proton NMR-(D$_2$O, w from TSP) |
|---|---|---|
| 2-methyl | diHCl | 2.66 (s, 3), 3.51 (m, 4), 4.54 (m, 4), 8.22 (s, 1) |
| 2,9-dimethyl | diHCl | 2.70 (s, 3), 3.52 (m, 4), 3.90 (s, 3), 4.62 (m, 4), 8.16 (s, 1) |
| 3-methyl | diHCl"0.33 H$_2$O | 3.52 (m, 4), 4.10 (s, 3), 4.52 (m, 4), 9.40 (s, 1), 8.56 (s, 1) |
| 3-ethyl | diHCl"0.5 H$_2$O | 1.58 (t, 3), 3.56 (m, 4), 4.58 (m, 6), 8.41 (s, 1), 8.61 (s, 1) |
| 4',9-dimethyl | diHCl"0.5 H$_2$O | 3.02 (s, 3), 3.32 (t, 2), 3.78 (m, 4), 3.90 (s, 3), 5.38 (d, 2), 8.24 (s, 1), 8.46 (s, 1) |
| 9-ethyl | diHCl | 1.49 (t, 3), 3.58 (m, 4), 4.34 (q, 2), 4.58 (m, 4), 8.38 (s, 1), 8.48 (s, 1) |
| 9-isopropyl | diHCl"0.33 H$_2$O | 1.60 (d, 6), 3.55 (m, 4), 4.80 (hept, 1), 8.39 (s, 1), 8.41 (s, 1) |
| 9-benzyl | diHCl | 3.52 (m, 4), 4.52 (m, 40), 5.50 (s, 2), 7.35 (m, 5), 8.30 (s, 1) 8.40 (s, 1) |

What is claimed is:

1. A compound having the formula:

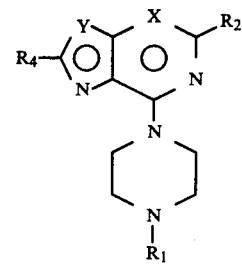

wherein
X is N-(R$_3$)m and Y is N(R$_3$)n; and
R$_1$ and R$_3$ are independently hydrogen, loweralkyl, cycloloweralkyl, loweralkenyl, loweralkoxyloweralkyl, loweralkenyl, loweralkynyl, or substituted loweralkyl where the substituent is from 1 to 3 of halogen, loweralkylthio, loweralkylsulfinyl, loweralkylsulfonyl, loweralkylamino or diloweralkylamino, or the substituent is one of a 5- or 6-membered heteroaromatic ring system with sulfur as the heteroatom, and m and n are 0 or 1 such that when m is 0, n is 1 and when m is 1, n is 0;
R$_2$ and R$_4$ are independently hydrogen, loweralkyl, cycloloweralkyl, loweralkoxy, loweralkylthio, loweralkylsulfinyl, loweralkylsulfonyl, loweralkenyl, loweralkenyloxy, loweralkynyl, substituted phenyl where the substituent is from 1 to 3 of halo or loweralkyl; or phenylloweralkyl; provided R$_1$, R$_2$, R$_3$ and R$_4$ are not simultaneously hydrogen; or X is CR$_3$ and Y is N—R$_3$ and R$_1$ and R$_3$ are independently hydrogen, loweralkyl, cycloloweralkyl, loweralkenyl, loweralkoxyloweralkyl, loweralkenyl, loweralkynyl, or phenylloweralkyl or substituted loweralkyl where the substituent is from 1 to 3 of halogen, loweralkylthio, loweralkylsulfinyl, loweralkylsulfonyl, loweralkylamino or diloweralkylamino, or the substituent is one of a 5- or 6-membered heteroaromatic ring system with nitrogen, oxygen or sulfur as the heteroatom;

R$_2$ and R$_4$ are independently hydrogen, loweralkyl, cycloloweralkyl, loweralkoxy, loweralkylthio, loweralkylsulfinyl, loweralkylsulfonyl, loweralkenyl, loweralkenyloxy, loweralkynyl, mono, di, or trihaloloweralkyl, phenyl or substituted phenyl where the substituent is from 1 to 3 of halo or lowerlalkyl, phenylloweralkyl, amino, loweralkylamino or dialkylamino where the alkyl groups can be linear, branched or joined in a ring of 5- or 6-members optionally containing oxygen or nitrogen as a heteroatom; or X is N and Y is O; and R$_1$ is hydrogen, loweralkyl, cycloloweralkyl, loweralkenyl, loweralkoxyloweralkyl, loweralkenyl, loweralkyl where the substituent is from 1 to 3 of halogen, loweralkylthio, loweralkylsulfinyl, loweralkylsulfonyl, loweralkylamino or diloweralkylamino, or the substituent is one of a 5- or 6-membered heteroaromatic ring system with nitrogen, oxygen or sulfur as the heteroatom;

R$_2$ and R$_4$ are independently hydrogen, loweralkyl, cycloloweralkyl, loweralkoxy, loweralkylthio, loweralkylsulfinyl, loweralkylsulfonyl, loweralkenyl, loweralkenyloxy, loweralkynyl, mono, di, or trihaloloweralkyl, phenyl or substituted phenyl where the substituent is from 1 to 3 of halo or loweralkyl, phenylloweralkyl, amino, loweralkylamino or dialkylamino where the alkyl groups can be linear branched; or joined in a ring of 5 or 6-members optionally containing oxygen or nitrogen as a heteroatom; or X is N and Y is S and R$_1$ is hydrogen, loweralkyl, cycloloweralkyl, loweralkenyl, loweralkoxyloweralkyl, loweralkenyl, loweralkynyl, or phenylloweralkyl or substituted loweralkyl where the substituent is from 1 to 3 of halogen, loweralkylthio, loweralkylsulfinyl, loweralkylsulfonyl, loweralkylamino or diloweralkylamino, or the substituent is one of a 5- or 6-membered heteroaromatic ring system with nitrogen, oxygen or sulfur as the heteroatom;

R$_2$ and R$_4$ are independently hydrogen, loweralkyl, cycloloweralkyl, loweralkoxy, loweralkylthio, loweralkylsulfinyl, loweralkylsulfonyl, loweralkenyl, loweralkenyloxy, loweralkynyl, mono, di, or trihaloloweralkyl, phenyl or substituted phenyl where the substituent is from 1 to 3 of halo or loweralkyl; phenylloweralkyl, or amino;

and the pharmaceutically acceptable salts thereof.

2. The compound of claim 1 wherein R$_1$ is hydrogen, loweralkyl, or loweralkenyl; R$_2$ is loweralkyl, loweralkoxy, amino, loweralkylamino, diloweralkylamino or pyrrolidino; each R$_3$ is independently hydrogen, loweralkyl, loweralkoxyloweralkyl, or halogenated loweralkyl.

3. The compound of claim 2 wherein R$_1$ is hydrogen, methyl, ethyl or 2-propenyl; R$_2$ is methyl, ethyl, methoxy, ethoxy, amino, methylamino, dimethylamino, pyrrolidino or ethylamino; each R$_3$ is independently hydrogen, methyl, ethyl, n-propyl, isopropyl, methoxymethyl, methoxyethyl or fluoroethyl; and each R$_4$ is independently hydrogen, methyl, methylamino, or dimethylamino.

4. The compound of claim 1 wherein X is N-(R$_3$)m and Y is N(R$_3$)n and R$_3$, m and n are as defined in claim 1.

5. The compound of claim 4 wherein X is N and Y is N—R$_3$.

6. The compound of claim 5 wherein R$_3$ is a halogenated branched loweralkyl.

7. The compound of claim 6 wherein R$_3$ is a halogenated isopropyl group.

8. The compound of claim 7 wherein R$_3$ is fluorinated isopropyl group.

9. The compound of claim 8 wherein R$_3$ is 1,3-difluoro isopropyl.

10. The compound of claim 4 wherein R$_1$ is hydrogen or methyl, and R$_2$ and R$_4$ are independently hydrogen, methyl, methoxy, ethoxy or dimethylamino.

11. The compound of claim 1 which is X=N, Y=-N—CH$_3$, R$_1$=H, R$_2$=CH$_2$CH$_3$ and R$_4$=H.

12. The compound of claim 1 which is X=N, Y=-N—CH$_2$CH$_2$CH$_3$, R$_1$=H, R$_2$=OCH$_3$ and R$_4$=H.

13. The compound of claim 1 which is X=N, Y=-N—CH$_2$OCH$_3$, R$_1$=H, R$_2$=OCH$_2$CH$_3$ and R$_4$=H.

14. The compound of claim 1 which is X=N, Y=-N—CH$_2$CH$_2$F, R$_1$=H, R$_2$=OCH$_3$ and R$_4$=H.

15. The compound of claim 1 which is X=N, Y=-N—CH$_2$CH$_2$F, R$_1$=H, R$_2$=CH$_2$CH$_3$ and R$_4$=H.

16. The compound of claim 1 which is X=N, Y=NCH$_2$CH$_2$CH$_2$F, R$_1$=H, R$_2$=OCH$_3$ and R$_4$=H.

17. The compound of claim 1 which is X=N, Y=NCH(CH$_3$)$_2$, R$_1$=H, R$_2$=OCH$_3$ and R$_4$=H.

18. The compound of claim 1 which is X=N, Y=NCH(CH$_2$F)$_2$ R$_1$=H R$_2$=OCH$_3$ and R$_4$=H.

19. The compound of claim 1 which is X=N, Y=NCH(CH$_2$F)$_2$ R$_1$=H, R$_2$=OCH$_2$CH$_3$ and R$_4$=H.

20. The compound of claim 1 which is X=N, Y=NCH(CH$_2$F)$_2$ R$_1$=H, R$_2$=CH$_2$CH$_3$ and R$_4$=H.

21. The compound of claim 1 which is X=N, Y=N-[1S,2R]CH(CH$_3$)CHFCH$_3$, R$_1$=H, R$_2$=OCH$_3$ and R$_4$=H.

22. The compound of claim 1 which is X=N, Y=N-[1S,2R]CH(CH$_3$)CHFCH$_3$, R$_1$=H, R$_2$=OCH$_3$ and R$_4$=CH$_3$.

23. The compound of claim 1 which is X=N, Y=N-[1S,2S]CH(CH$_3$)CHFCH$_3$, R$_1$=H, R$_2$=OCH$_3$ and R$_4$=H.

24. The compound of claim 1 which is X=N, Y=N-[1S,2S]CH(CH$_3$)CHFCH$_3$, R$_1$=H, R$_2$=OCH$_3$ and R$_4$=CH$_3$.

25. The compound of claim 1 which is X=N, Y=N-[1R,2S]CH(CH$_3$)CHFCH$_3$, R$_1$=H, R$_2$=OCH$_3$ and R$_4$=H.

26. The compound of claim 1 which is X=N, Y=N-[1R,2S]CH(CH$_3$)CHFCH$_3$, R$_1$=H, R$_2$=OCH$_3$ and R$_4$=CH$_3$.

27. The compound of claim 1 which is X=N, Y=N-[1R,2R]CH(CH$_3$)CHFCH$_3$, R$_1$=H, R$_2$=OCH$_3$ and R$_4$=H.

28. The compound of claim 1 which is X=N, Y=N-[1R,2R]CH(CH$_3$)CHFCH$_3$, R$_1$=H, R$_2$=OCH$_3$ and R$_4$=CH$_3$.

29. The compound of claim 1 which is X=N, Y=N-[S]CH(CH$_3$)CH$_2$CH$_3$, R$_1$=H, R$_2$=OCH$_3$ and R$_4$=H.

30. The compound of claim 1 which is X=N, Y=N-[R]CH(CH$_3$)CH$_2$CH$_3$, R$_1$=H, R$_2$=OCH$_3$ and R$_4$=H.

31. The compound of claim 1 which is X=N, Y=N-[1S,2R]CH(CH$_3$)CH(OCH$_3$)CH$_3$, R$_1$=H, R$_2$=OCH$_3$ and R$_4$=H.

32. The compound of claim 1 which is X=N, Y=N-[1S,2S]CH(CH$_3$)CH(OCH$_3$)CH$_3$, R$_1$=H, R$_2$=OCH$_3$ and R$_4$=H.

33. The compound of claim 1 which is X=N, Y=N-[1R,2S]CH(CH$_3$)CH(OCH$_3$)CH$_3$, R$_1$=H, R$_2$=OCH$_3$ and R$_4$=H.

34. The compound of claim 1 which is X=N, Y=N-[1R,2R]CH(CH$_3$)CH(OCH$_3$)CH$_3$, R$_1$=H, R$_2$=OCH$_3$ and R$_4$=H.

35. A method for the treatment of diabetes or obesity with associated insulin resistance which comprises administering to a patient in need of such treatment an effective amount of a compound of claim 1.

36. A composition useful for the treatment of diabetes or obesity with associated insulin resistance which comprises an inert carrier and an effective amount of a compound of claim 1.

* * * * *